US012703679B2

(12) United States Patent
Dewji et al.

(10) Patent No.: US 12,703,679 B2
(45) Date of Patent: Aug. 11, 2026

(54) SULFONE COMPOUNDS AND PHARMACEUTICAL COMPOSITIONS THEREOF, AND THEIR THERAPEUTIC APPLICATIONS

(71) Applicant: Cura Therapeutics, LLC, La Jolla, CA (US)

(72) Inventors: Nazneen Dewji, San Diego, CA (US); Darryl Rideout, Milford, PA (US); Gerard Rosse, Poway, CA (US)

(73) Assignee: Cura Therapeutics, LLC, La Jolla, CA (US)

( * ) Notice: Subject to any disclaimer, the term of this patent is extended or adjusted under 35 U.S.C. 154(b) by 855 days.

(21) Appl. No.: 17/625,704

(22) PCT Filed: Jul. 10, 2020

(86) PCT No.: PCT/US2020/041507

§ 371 (c)(1),
(2) Date: Jan. 7, 2022

(87) PCT Pub. No.: WO2021/007478

PCT Pub. Date: Jan. 14, 2021

(65) Prior Publication Data

US 2022/0274922 A1 Sep. 1, 2022

Related U.S. Application Data

(60) Provisional application No. 62/873,117, filed on Jul. 11, 2019.

(51) Int. Cl.
*C07C 311/21* (2006.01)
*C07C 317/44* (2006.01)

(52) U.S. Cl.
CPC .......... *C07C 311/21* (2013.01); *C07C 317/44* (2013.01)

(58) Field of Classification Search
CPC .................................................... C07C 311/21
See application file for complete search history.

(56) References Cited

U.S. PATENT DOCUMENTS

| | | | |
|---|---|---|---|
| 2,608,506 | A | 8/1952 | Sprague et al. |
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 3,954,994 | A | 5/1976 | Holland et al. |
| 4,006,007 | A | 2/1977 | Bollinger et al. |
| 4,008,719 | A | 2/1977 | Theeuwes et al. |
| 4,328,245 | A | 5/1982 | Yu et al. |
| 4,409,239 | A | 10/1983 | Yu |
| 4,410,545 | A | 10/1983 | Yu et al. |
| 5,033,252 | A | 7/1991 | Carter |
| 5,052,558 | A | 10/1991 | Carter |
| 5,059,595 | A | 10/1991 | LeGrazie |
| 5,073,543 | A | 12/1991 | Marshall et al. |
| 5,120,548 | A | 6/1992 | McClelland et al. |
| 5,130,119 | A | 7/1992 | Blaszkiewicz et al. |
| 5,323,907 | A | 6/1994 | Kalvelage |
| 5,354,556 | A | 10/1994 | Sparks et al. |
| 5,591,767 | A | 1/1997 | Mohr et al. |
| 5,612,059 | A | 3/1997 | Cardinal et al. |
| 5,639,476 | A | 6/1997 | Oshlack et al. |
| 5,639,480 | A | 6/1997 | Bodmer et al. |
| 5,674,533 | A | 10/1997 | Santus et al. |
| 5,698,220 | A | 12/1997 | Cardinal et al. |
| 5,709,874 | A | 1/1998 | Hanson et al. |
| 5,733,566 | A | 3/1998 | Lewis |
| 5,739,108 | A | 4/1998 | Mitchell |
| 5,759,542 | A | 6/1998 | Gurewich |
| 5,798,119 | A | 8/1998 | Herbig et al. |
| 5,840,674 | A | 11/1998 | Yatin et al. |

(Continued)

FOREIGN PATENT DOCUMENTS

| | | | |
|---|---|---|---|
| CN | 105985265 | A | 10/2016 |
| CN | 109293537 | A | 2/2019 |

(Continued)

OTHER PUBLICATIONS

International Search Report and Written Opinion, dated Nov. 17, 2020 for PCT Application No. PCT/US2020/041507 filed Jul. 10, 2020 (11 pages).
Purohit et al., "Synthesis of 5-arylaminosulpho-N-acetylanthranilic acid, 6-arylaminosulpho-2-methyl-3-amino/3-N-chloroacetamido/3-N-arylamino acetamido-4-(3H)-quinazolones as potential anti-HIV, anticancer and antimicrobial agents", XP002800676, retrieved from Chemical Abstracts Service, STN Database accession No. 2004:165997.
Sinhababu, et al., "Prodrugs of Anticancer Agents," Adv. Drug Delivery Rev., vol. 19, pp. 241-273 (1996).
Sokolova, et al., "Synthesis and Analgesic Activity of New [alpha]-truxillic acid Derivatives with Monoterpenoid Fragments," Medicinal Chemistry Research, vol. 25, Issue 8, pp. 1608-1615 (2016).
"Solubility Product Constants, Ksp," Purdue Chemistry, 4 pages, (Jan. 31, 2002).

(Continued)

*Primary Examiner* — Golam M Shameem
(74) *Attorney, Agent, or Firm* — The Marbury Law Group, PLLC

(57) ABSTRACT

Provided herein are sulfone compounds, for example, a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and pharmaceutical compositions thereof. Also provided herein are methods of their use for treating, preventing, or ameliorating one or more symptoms of a disorder, disease, or condition.

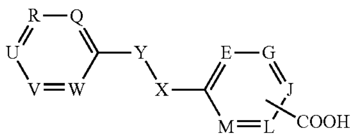

(A)

23 Claims, 3 Drawing Sheets

(56) References Cited

U.S. PATENT DOCUMENTS

| | | | |
|---|---|---|---|
| 5,891,474 | A | 4/1999 | Busetti et al. |
| 5,900,252 | A | 5/1999 | Calanchi et al. |
| 5,922,356 | A | 7/1999 | Koseki et al. |
| 5,929,097 | A | 7/1999 | Levin et al. |
| 5,972,366 | A | 10/1999 | Haynes et al. |
| 5,972,891 | A | 10/1999 | Kamei et al. |
| 5,980,945 | A | 11/1999 | Ruiz |
| 5,985,307 | A | 11/1999 | Hanson et al. |
| 5,993,855 | A | 11/1999 | Yoshimoto et al. |
| 6,004,534 | A | 12/1999 | Langer et al. |
| 6,039,975 | A | 3/2000 | Shah et al. |
| 6,045,830 | A | 4/2000 | Igari |
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,350,458 | B1 | 2/2002 | Modi |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 8,362,000 | B2 | 1/2013 | Bian et al. |
| 9,416,101 | B2 | 8/2016 | Orton |
| 9,630,957 | B2 | 4/2017 | Li et al. |
| 9,890,117 | B2 | 2/2018 | Silverman et al. |
| 11,701,334 | B2 * | 7/2023 | Dewji .................... A61K 31/18 514/604 |
| 2010/0152121 | A1 | 6/2010 | Priebe et al. |
| 2010/0152125 | A1 | 6/2010 | Agar et al. |
| 2012/0094964 | A1 | 4/2012 | Inoue et al. |
| 2017/0081278 | A1 | 3/2017 | Birault et al. |
| 2021/0052525 | A1 | 2/2021 | Dewji |
| 2021/0052529 | A1 | 2/2021 | Dewji |
| 2022/0274921 | A1 | 9/2022 | Dewji |
| 2022/0274922 | A1 | 9/2022 | Dewji et al. |
| 2023/0165823 | A1 | 6/2023 | Dewji |
| 2024/0016768 | A1 | 1/2024 | Dewji |
| 2025/0177334 | A1 | 6/2025 | Dewji |

FOREIGN PATENT DOCUMENTS

| | | | |
|---|---|---|---|
| CN | 109651208 | A | 4/2019 |
| EP | 3006432 | A1 | 4/2016 |
| JP | 2006160752 | A | 6/2006 |
| JP | 2008308493 | A | 12/2008 |
| WO | 1999/36398 | A1 | 7/1999 |
| WO | 2000/50391 | A1 | 8/2000 |
| WO | 2002/17918 | A2 | 3/2002 |
| WO | 2003/028044 | A2 | 4/2003 |
| WO | 2004005278 | A1 | 1/2004 |
| WO | 2004033418 | A2 | 4/2004 |
| WO | 2005026134 | A1 | 3/2005 |
| WO | 2005085189 | A2 | 9/2005 |
| WO | 2005092845 | A1 | 10/2005 |
| WO | 2006007864 | A1 | 1/2006 |
| WO | 2006017836 | A2 | 2/2006 |
| WO | 2007071443 | A1 | 6/2007 |
| WO | 2008079906 | A1 | 7/2008 |
| WO | 2008116092 | A1 | 9/2008 |
| WO | 2008129288 | A2 | 10/2008 |
| WO | 2010083264 | A1 | 7/2010 |
| WO | 2010129567 | A1 | 11/2010 |
| WO | 2010129570 | A1 | 11/2010 |
| WO | 2012031196 | A1 | 3/2012 |
| WO | 2013054108 | A1 | 4/2013 |
| WO | 2014096140 | A1 | 6/2014 |
| WO | 2014190899 | A1 | 12/2014 |
| WO | 2015186056 | A1 | 12/2015 |
| WO | 2016090317 | A1 | 6/2016 |
| WO | 2016122317 | A1 | 8/2016 |
| WO | 2016164685 | A1 | 10/2016 |
| WO | 2017011323 | A1 | 1/2017 |
| WO | 2017160069 | A1 | 9/2017 |
| WO | 2018156297 | A1 | 8/2018 |
| WO | 2018227886 | A1 | 12/2018 |
| WO | 2019139869 | A1 | 7/2019 |
| WO | 2019139871 | A1 | 7/2019 |
| WO | 2021007474 | A1 | 1/2021 |
| WO | 2021007478 | A1 | 1/2021 |

OTHER PUBLICATIONS

Stella, et al., "Prodrugs Do They Have Advantages in Clinical Practice?" Drugs, vol. 29, pp. 455-473 (1985).

Ehara Takeru, et al., "Structure-Based Design of Substituted Piperdines as a New Class of Highly Efficacious Oral Direct Renin Inhibitors", ACS Medicinal Chemistry Letters, vol. 5, No. 7, pp. 787-792, (May 8, 2014).

Tan, et al., "Development and Optimization of Anti-HIV Nucleoside Analogs and Prodrugs: A Review of Their Celluar Pharmacology, Structure-Activity Relationships and Pharmacokinetics," Adv. Drug Delivery Rev. Vol. 39, pp. 117-151 (1999).

Taylor, "Improved Passive Oral Drug Delivery Via Prodrugs," Adv. Drug Delivery Rev., vol. 19, pp. 131-148 (1996).

Testa, "Prodrug research: futile or fertile?" Biochemical Pharmacology, vol. 68, Issue 11, pp. 2097-2106 (2004).

Valentino, et al., "Prodrug Strategies to Enhance the Intestinal Absorption of Peptides," Drug Discovery Today, vol. 2, No. 4, pp. 148-155 (1997).

Verma, et al., "Osmotically Controlled Oral Drug Delivery," Drug Development and Industrial Pharmacy, vol. 26, No. 7, pp. 695-708, DOI: 10.1081/DDC-100101287, (2000).

Verma, et al., "Formulation Aspects in the Development of Osmotically Controlled Oral Drug Delivery Systems," J. Controlled Release, vol. 79, pp. 7-27 (2002).

Waller, et al., "Prodrugs," Br. J. Clin. Pharmac., vol. 28, pp. 497-507 (1989).

Wang, et al., "Prodrug approaches to the improved delivery of peptide drugs", Curr. Pharm. Design, 5, 265-287, (1999).

"What is Tris(hydroxymethyl)aminomethane)(TrisBuffer)?", DC Fine Chemicals, (Apr. 5, 2023).

Wiebe, et al., "Concepts for the Design of Anti-HIV Nucleoside Prodrugs for Treating Cephalic HIV Infection," Adv. Drug Delivery Rev., vol. 39, pp. 63-80 (1999).

Yang, et al., "Discovery of a VHL and HIFa interaction inhibitor with in vivo angiogenic activity via structure-based virtual screening," Chemical Communications, vol. 52, pp. 12837-12840 (2016).

Yang, et al., Supporting Information, " Discovery of a VHL and HIFa interaction inhibitor with in vivo angiogenic activity via structure-based virtual screening," Electronic Supplementary Material (ESI) for ChemComm, This journal is @The Royal Society of Chemistry (2016).

Zhou, et al., "Synthesis and biological evaluation of novel (E)-N'-(2,3-dihydro-1H-inden-1-ylidene) benzohydrazides as potent LSDI inhibitors," Bioorganic & Medicinal Chemistry Letters, vol. 26, pp. 4552-4557 (2016).

Bundgaard, "XIII. Improved drug delivery by the prodrug approach", Controlled Drug Delivery, 17, pp. 179-196 (1987).

English Translation of Taiwan Office Action for counterpart Application No. 108100742, dated Jan. 16, 2025.

First Examination Report issued in Australian Patent Application 2019207491 dated Nov. 10, 2023.

First Examination Report issued in Australian Patent Application 2024259810 dated Dec. 1, 2025.

(56) References Cited

OTHER PUBLICATIONS

JP OA—Final Notification of Reasons for Refusal issued in related Japanese Patent Application No. 2023-144990 dated Apr. 1, 2025, including English Abstract (3 pages).
Abdel-Halim, et al., "Discovery and Optimization of 1,3,5-Trisubstituted Pyrazolines as Potent and Highly Selective Allosteric Inhibitors of Protein Kinase C-ζ", J. Med. Chem. 2014, 57, pp. 6513-6530, (2014).
Amidon, et al., "Transport Processes in Pharmaceutical Systems," Ed. Marchell Dekker, 185-218, (2000).
Balant et al., "Prodrugs for the improvement of drug absorption via different routes of administration", Eur. J. Drug Metab. Pharmacokinet, vol. 15, No. 2, pp. 143-153 (1990).
Balimane, et al., "Involvement of multiple transporters in the oral absorption of nucleoside analogues", Adv. Drug Delivery Rev. 39, pp. 183-209, (1999).
Ballard et al., "Alzheimer's Disease", Lancet 377, pp. 1019-1031, (2011).
Berge, et al., J. Pharm. Sci., 66, 1-19: Handbook of Pharmaceutical Salts: Properties, Selection, and Use, 2nd ed. (1977).
Blondet, et al., "A Convenient Synthesis of 3,4-Dihydro-2,2-Dioxide 5-Hydroxy-2, 1-Benzothiazine", Tetrahedron Letters, vol. 35, No. 18, pp. 2911-2912, (1994).
Browne, "Review Fosphenytoin (Cerebyx)", Clinical Neuropharmacology, vol. 20, No. 1, pp. 1-12, (1997).
Bungaard, "Means to Enhance Penetration, Prodrugs as a means to improve the delivery of peptide drugs", Advanced Drug Delivery Review, 8, pp. 1-38, (1992).
Chemical Abstracts STN Registry Database, Record for 313523-51-2, entered into STN (Jan. 11, 2001).
Ehara, et al., "Structure-Based Design of Substituted Piperidines as a New Class of Highly Efficacious Oral Direct Renin Inhibitors," ACS Medicinal Chemistry Letters, 5(7), pp. 787-792, (2014).
Ettmayer et al., 2004, "Lessons Learned from Marketed and Investigational Prodrugs," Journal of Medicinal Chemistry, 47(10), pp. 2393-2404, (2004).
Farquhar, et al., "Biologically Reversible Phosphate-Protective Groups," J Pharm. Sci., vol. 72, No. 3, pp. 324-325 (Mar. 1983).
Fleisher, et al., "Improved oral drug delivery: solubility limitations overcome by the use of prodrugs," Adv. Drug Delivery Rev., vol. 19, pp. 115-130 (1996).
Fleisher, et al., "Design of Prodrugs for Improved Gastrointestinal Absorption by Intestinal Enzyme Targeting," Methods Enzymol., vol. 112, pp. 360-381 (1996).
Freeman, et al., "Bioreversible Protection for the Phospho Group: Chemical Stabiity and Bioactivation of Di(4-acetoxybenzyl) Methylphosphonate with Carboxyesterase," J. Chem. Soc., Chem. Commun., 875-877 (1991).
Frigerio, et al., "Alzheimer's Disease Mechanisms and Emerging Roads to Novel Therapeutics," Annu. Rev. Neurosci. vol. 39, pp. 57-59 (2016).
Friis, et al., "Prodrugs of phosphates and phosphonates: Novel lipophilic a-acyloxyalkyl ester derivatives of phosphate- or phosphonate containing drugs masking the negative charges of these groups," Eur. J. Pharm. Sci., vol. 4, pp. 49-59 (1996).
Furutachi, et al., "Novel Trivalent C3-Symmetrical Phenylboronic Acid Pinacol Esters and Their Biological Evaluation," Heterocycles, vol. 96(1), pp. 144-151 (2018).
Gein, et al., "Synthesis and Antimicrobial Activity of N,N', 2-Trlaryl-6-Hydroxy-6-Methyl-4-Oxocyclohexane-1,3-Dicarboxamides," Pharmaceutical Chemistry Journal, vol. 49(4), pp. 246-249 (2015).
Gibson, M. (Ed.). "Pharmaceutical Preformulation and Formulation: A Practical Guide from Candidate Drug Selection to Commercial Dosage Form," (2nd ed.). CRC Press. https://doi.org/10.3109/9781420073188.
Han, et al., "Targeted Prodrug Design to Optimize Drug Delivery," AAPS PharmSci, vol. 2(1), pp. 1-11 (2000).
Hanke, et al., "Synthesis and pharmacological characterization of benzenesulfonamides as dual species inhibitors of human and mrine mPGES-1," Bioorganic & Med. Chem., vol. 21, pp. 7874-7883 (2013).
International Search Report dated Apr. 4, 2019 for PCT/US2019/012612 (4 pages).
International Preliminary Report on Patentability and Written Opinion of the International Searching Authority issued in counterpart Application No. PCT/US2019/012612, mailed Jul. 14, 2020, 7 pages.
International Search Report issued in counterpart Application No. PCT/US2019/012608, mailed Jun. 26, 2019, 6 pages.
International Preliminary Report on Patentability and Written Opinion of the International Searching Authority issued in counterpart Application No. PCT/US2019/012608, mailed Jul. 14, 2020, 15 pages.
International Search Report issued in counterpart Application No. PCT/US2020/041497, dated Oct. 30, 2020, 8 pages.
International Search Report for counterpart Application No. PCT/US2020/041507, dated Nov. 17, 2020 (5 pages).
International Preliminary Report on Patentability and Written Opinion of the International Searching Authority issued in International Application No. PCT/US2020/041507 dated Jan. 11, 2022 (8 pages).
Israel, et al., "Proving Sporadic and Familial Alzheimer's Disease Using Induced Pluripotent Stem Cells," Nature, vol. 482, pp. 216-220 (2012).
Kaczocha, et al., " Inhibition of Fatty Acid Binding Proteins Elevates Brain Anandamide Levels and Produces Analgesia," PloS One, vol. 9, Issue 4, e94200 (2014).
Kozaki, "Special Feature: Diagnosis and Treatment of Alzheimer's Disease, 1. Clinical diagnosis of Alzheimer's disease," Japanese Journal of Geriatrics, vol. 49, Issue 4, pp. 419-424, (ISSN: 0300-9173), (2012).
Kumar, et al., "Phosphorylation of amyloid beta (Aβ) peptides—A trigger for formation of toxic aggregates in Alzheimer's disease," Aging, vol. 3., No. 8, pp. 803-812, 10 pages, (Aug. 2011).
Masters, et al., "Alzheimer's Disease," Nat. Rev. Dis. Primers vol. 1, Article 15056, doi:10.1038/nrdp.2015.56 (Oct. 15, 2015).
Nathwani, et al., "Penicillins A Current Review of Their Clinical Pharmacology and Therapeutic Use," Drugs, vol. 45, Issue 6, pp. 866-894 (1993).
Non-Final Office Action for U.S. Appl. No. 17/989,981, dated Apr. 9, 2025.
Non-Final Office Action for U.S. Appl. No. 17/989,981, dated Jun. 5, 2024.
Final Office Action for U.S. Appl. No. 17/989,981, dated Feb. 18, 2026.
Non-Final Office Action for copending U.S. Appl. No. 17/625,704, dated May 8, 2025.
Non-Final Office Action for copending U.S. Appl. No. 17/625,698, dated Nov. 12, 2024.
Final Office Action for copending U.S. Appl. No. 17/625,698, dated Apr. 14, 2025.
Non-Final Office Action for copending U.S. Appl. No. 18/205,283, dated Feb. 29, 2024.
Non-Final Office Action for copending U.S. Appl. No. 16/961,191, dated Apr. 1, 2022.
Non-Final Office Action for copending U.S. Appl. No. 16/961,191, dated Jun. 24, 2022.
Pahadi, et al., "Catalytic intermolecular hydroamination of vinyl etherts," NIH Public Access Author Manuscript, Synlett., vol. 19, pp. 3135-3138, doi:10.1055/2-0029-1218293, (Dec. 1, 2009).
Pauletti, et al., "Improvement of oral peptide bioavailability: Peptidomimetic and prodrug strategies," Advanced Drug Delivery Reviews, vol. 27, pp. 235-256 (1997).
Pulici, et al., "Optimization of Diarylthiazole B-Raf Inhibitors: Identification of a Compound Endowed with High Oral Antitumor Activity, Mitigated hERG Inhibition, and Low Paradoxical Effect," ChemMedChem, vol. 10, pp. 276-295 (2015).
Purohit, et al. "Synthesis of 5-arylaminosulpho-N-acetylanthranilic acid, 6-arylaminosulpho-2-methyl-3-amino/3-N-chloroacetamido/3-Narylamino acetamido-4-(3H)-quinazolones as potential anti-HIV,

(56) References Cited

OTHER PUBLICATIONS anticancer and antimicrobial agents," Chemical Abstracts Service, retrieved from STN, Database accession No. 2004: 165997 abstract, (Oct. 14, 2020).

Santus, et al., "Osmotic Drug Delivery: a Review of the Patent Literature," J. Controlled Release, vol. 35, pp. 1-21 (1995).

Isshiki et al., "Syntheses of p. Guanylphenylsulfonamide Derivatives and Their Related Compounds", Yakugaku Zasshi, vol. 70, pp. 531-534, (1950).

Jablonska-Pikus et al., "Effect of molecular structure on optical properties of sulfoxide systems. 2-(3'-X Methylbenzylsulfinyl)benzoic acids and some of their derivatives", II, Annales Universitatis Mariae Curie-Sklodowska, Sectio AA: Chemia, vol. 42-3, pp. 111-127, (1992).

Jablonska-Pikus et al., "Effect of molecular structure on optical properties of sulfoxide systems. 2-(3'-U Methylbenzylsulfinyl)benzoic acids and some of their derivatives" II, Annales Universitatis Mariae Curie-Sklodowska, Sectio AA: Chemia, vol. 42-3, pp. 129-144, (1992).

Janczewski et al., "Effect of molecular structure on optical properties of acids and some of their derivatives". Part II, Polish Journal of Chemistry, vol. 57, No. 10-12, pp. 1205-1218 (1983).

Janczewski et al., "Effect of molecular structure on optical properties of sulfoxide systems. 2-(4- bromobenzylsulfinyl) benzoic acids and some of their derivatives", Part II, Annales Universitatis Mariae Curie-Sklodowska, Sectio AA: Physica et Chemia, vol. 38, pp. 67-93, (1983).

Janczewski et al., "Effect of molecular structure on optical properties of sulfoxide systems. 2-(2-Bromobenzylsulfinyl) benzoic acids and some of their derivatives", Part V, Polish Journal of Chemistry, vol. 60, No. 7-12, pp. 775-789 (1986).

Majewski et al., "Synthesis of isomeric 3-(2'-, 3'-and 4'-bromobenzylmercapto)benzoic acids and their sulfinyl and sulfonyl derivatives", Polish Journal of Chemistry, vol. 64, No. 7-12, pp. 827-828 (1990).

Woolley et al., "Synthesis of Derivatives of 1,2-Dichloro-4-Benzenesulfonamido-5-Nitrobenzene and Their Use in the Chemotherapy of Spontaneous Cancers", Canadian Journal of Chemistry, vol. 43, No. 5, pp. 1454-1459 , (1965).

Lombardino et al., "PreparationandAntiinflammatoryActivityof Some 2-Arylbenzo[b]thiophen-3(2H)-one 1, 1-Dioxides, Journal of Medicinal Chemistry", vol. 13, No. 2, pp. 206-210, (1970).

Final Office Action for copending U.S. Appl. No. 17/625,698, dated Jun. 16, 2026.

CAS Printout of JP 06247047, 1994.

* cited by examiner

SULFONE COMPOUNDS AND PHARMACEUTICAL COMPOSITIONS THEREOF, AND THEIR THERAPEUTIC APPLICATIONS

CROSS REFERENCE TO RELATED APPLICATION

This application is a U.S. National Stage Application under 35 U.S.C. § 371 of International Patent Application No. PCT/US2020/041507, filed Jul. 10, 2020, which claims the benefit of the priority of U.S. Provisional Application No. 62/873,117, filed Jul. 11, 2019. Each of the foregoing related applications, in its entirety, is incorporated herein by reference.

STATEMENT REGARDING FEDERALLY SPONSORED RESEARCH OR DEVELOPMENT

This invention was made with government support under R44AG055182 awarded by National Institutes of Health. The government has certain rights in the invention.

FIELD

Provided herein are sulfone compounds and pharmaceutical compositions thereof. Also provided herein are methods of their use for treating, preventing, or ameliorating one or more symptoms of a disorder, disease, or condition.

BACKGROUND

Alzheimer's disease (AD), a chronic neurodegenerative disease, is the most common cause of dementia. Ballard et al., *Lancet* 2011, 377, 1019-1031; Kumar and Walter, *Aging* 2011, 3, 803-812; Masters et al., *Nat. Rev. Dis. Primers* 2015, 1, 15056; Frigerio and Strooper, *Annu. Rev. Neurosci.* 2016, 39, 57-79. AD is caused by abnormal deposits of proteins in the brain that destroy cells in the areas of the brain that control memory and mental functions. Ballard et al., *Lancet* 2011, 377, 1019-1031; Masters et al., *Nat. Rev. Dis. Primers* 2015, 1, 15056. The accumulation of amyloid β-peptides (Aβ) is the primary underlying disease mechanism driving its progression. Id. Aβ peptides create plaque-like deposits in the brain, and accumulate gradually and progressively as a result of an imbalance between their production and clearance. Only when neuronal loss progresses and a certain threshold is reached do the clinical symptoms of AD start to appear. Because Aβ build-up happens gradually over time, it can take between 10 and 20 years before a patient begins showing any obvious signs of the disease.

The most common early symptom of AD is difficulty in remembering recent events. As the disease advances, symptoms can include problems with language, disorientation, mood swings, and behavioral issues. People with the disease may even forget important people in their lives and undergo dramatic personality changes. Gradually, bodily functions are lost, ultimately leading to death. Although the speed of progression can vary, the average life expectancy following diagnosis is 3 to 9 years. Masters et al., *Nat. Rev. Dis. Primers* 2015, 1, 15056.

Current AD medications may ameliorate some of the symptoms of the disease. Id. However, as of today, there is no cure for AD. Id. Therefore, there is an unmet need to develop effective therapeutics for treating AD.

SUMMARY OF THE DISCLOSURE

Provided herein is a compound of Formula A:

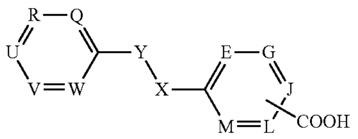

(A)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof;

wherein:

E and Q are each independently a bond, —O—, —S—, —N═, —N($R^A$)—, or —C($R^A$)—;

G, J, L, M, R, U, V, and W are each independently —O—, —S—, —N═, —N($R^A$)—, or —C($R^A$)—;

X is —$SO_2$— and Y is —$CR^XR^Y$— or —N($R^A$)—; or X is —$CR^XR^Y$— and Y is —$SO_2$—;

each $R^A$, $R^X$, and $R^Y$ is independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(═N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS$(O)_2R^{1a}$, —OS(O)N$R^{1b}R^{1c}$, —OS$(O)_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(═N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S$(O)_2R^{1d}$, —N$R^{1a}$S(O)N$R^{1b}R^{1c}$, —N$R^{1a}$S$(O)_2$N$R^{1b}R^{1c}$, —S(O)$R^{1a}$, —S$(O)_2R^{1a}$, —S(O)N$R^{1b}R^{1c}$ or —S$(O)_2$N$R^{1b}R^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(═N$R^a$)N$R^bR^c$, —OC(S)$R^a$, —OC(S)O$R^a$, —OC(S)N$R^bR^c$, —OS(O)$R^a$, —OS$(O)_2R^a$, —OS(O)N$R^bR^c$, —OS$(O)_2$N$R^bR^c$, —N$R^bR^c$, —N$R^a$C(O)

$R^d$, $-NR^aC(O)OR^d$, $-NR^aC(O)NR^bR^c$, $-NR^aC(O)SR^d$, $-NR^aC(=NR^d)NR^bR^c$, $-NR^aC(S)R^d$, $-NR^aC(S)OR^d$, $-NR^aC(S)NR^bR^c$, $-NR^aS(O)R^d$, $-NR^aS(O)_2R^d$, $-NR^aS(O)NR^bR^c$, $-NR^aS(O)_2NR^bR^c$, $-SR^a$, $-S(O)R^a$, $-S(O)_2R^a$, $-S(O)NR^bR^c$, and $-S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $-C(O)R^e$, $-C(O)OR^e$, $-C(O)NR^fR^g$, $-C(O)SR^e$, $-C(NR^e)NR^fR^g$, $-C(S)R^e$, $-C(S)OR^e$, $-C(S)NR^fR^g$, $-OR^e$, $-OC(O)R^e$, $-OC(O)OR^e$, $-OC(O)NR^fR^g$, $-OC(O)SR^e$, $-OC(=NR^e)NR^fR^g$, $-OC(S)R^e$, $-OC(S)OR^e$, $-OC(S)NR^fR^g$, $-OS(O)R^e$, $-OS(O)_2R^e$, $-OS(O)NR^fR^g$, $-OS(O)_2NR^fR^g$, $-NR^fR^g$, $-NR^eC(O)R^h$, $-NR^eC(O)OR^f$, $-NR^eC(O)NR^fR^g$, $-NR^eC(O)SR^f$, $-NR^eC(=NR^h)NR^fR^g$, $-NR^eC(S)R^h$, $-NR^eC(S)OR^f$, $-NR^eC(S)NR^fR^g$, $-NR^eS(O)R^h$, $-NR^eS(O)_2R^h$, $-NR^eS(O)NR^fR^g$, $-NR^eS(O)_2NR^fR^g$, $-SR^e$, $-S(O)R^e$, $-S(O)_2R^e$, $-S(O)NR^fR^g$, and $-S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a pharmaceutical composition comprising a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

Furthermore, provided herein is a method of treating a disorder, disease, or condition, in one embodiment, a neurodegenerative disease, in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

Provided herein is a method of inhibiting the production of amyloid β in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of attenuating the amyloid β level in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the production of amyloid β in a cell, comprising contacting the cell with an effective amount of a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

Provided herein is a method of attenuating the amyloid β-induced signaling pathway activity in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the production of a tau protein in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In one embodiment, the tau protein is a phosphorylated tau protein. In another embodiment, the tau protein is a hyperphosphorylated tau protein.

Provided herein is a method of attenuating the tau protein level in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In one embodiment, the tau protein level is a phosphorylated tau protein level. In another embodiment, the tau protein level is a hyperphosphorylated tau protein level.

Provided herein is a method of inhibiting the production of a tau protein in a cell, comprising contacting the cell with an effective amount of a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof. In one embodiment, the tau protein is a phosphorylated tau protein. In another embodiment, the tau protein is a hyperphosphorylated tau protein.

Provided herein is a method of attenuating thea tau protein-induced signaling pathway activity in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

DETAILED DESCRIPTION

Figure 1:
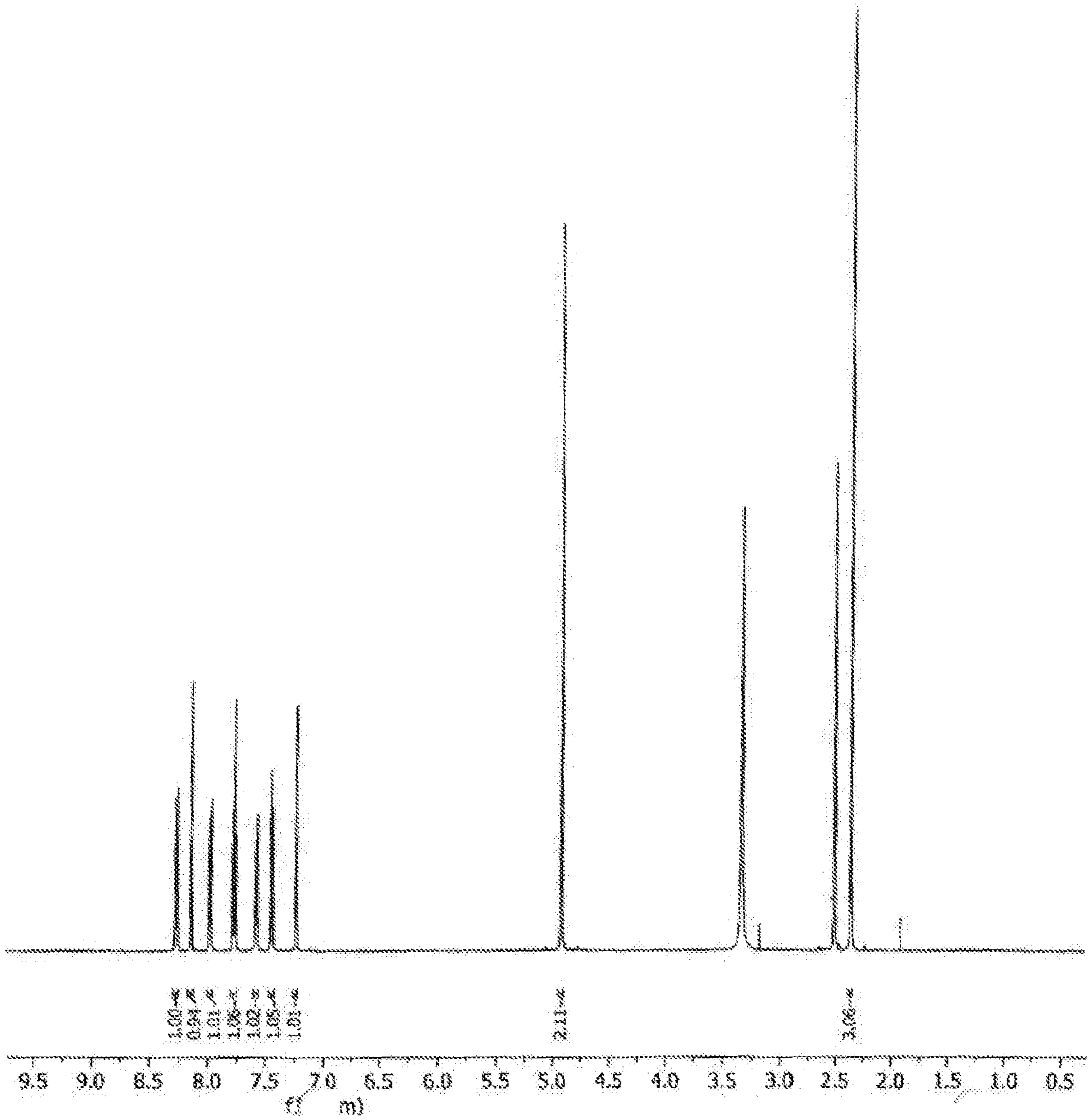
FIG. 1 shows a $^1H$ NMR spectrum of compound A1.

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.: Philadelphia, Pa., 2012; *Handbook of Pharmaceutical Excipients,* 8th ed.; Sheskey et al., Eds.; The Pharmaceutical Press: 2017; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound or a pharmaceutical composition thereof, which is administered to a subject for treating, preventing, or ameliorating one or more symptoms of a disorder, disease, or condition.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one, two, three, four, or five, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one, two, three, four, or five, in another embodiment, one, carbon-carbon triple bond(s). The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl ($—C≡CH$), propynyl (including all isomeric forms, e.g., 1-propynyl ($—C≡CCH_3$) and propargyl ($—CH_2C≡CH$)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is polycyclic. In yet another embodiment, the aryl is bicyclic. In still another embodiment, the aryl is tricyclic. In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, O-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen", "halide," or "halo" refers to fluorine, chlorine, bromine, and/or iodine.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more, one, two, three, or four, substituents Q, each of which is independently selected from, e.g., (a) deuterium (-D), cyano (—CN), halo, and nitro (—$NO_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(═N$R^a$)N$R^bR^c$, —OC(S)$R^a$, —OC(S)O$R^a$, —OC(S)N$R^bR^c$, —OS(O)$R^a$, —OS$(O)_2R^a$, —OS(O)N$R^bR^c$, —OS$(O)_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(═N$R^d$)$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S$(O)_2R^d$, —N$R^a$S(O)N$R^bR^c$, —N$R^a$S$(O)_2$N$R^bR^c$, —S$R^a$, —S(O)$R^a$, —S$(O)_2R^a$, —S(O)N$R^bR^c$, and —S$(O)_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(═N$R^e$)N$R^fR^g$, —OC(S)$R^e$, —OC(S)O$R^e$, —OC(S)N$R^fR^g$, —OS(O)$R^e$, —OS$(O)_2R^e$, —OS(O)N$R^fR^g$, —OS$(O)_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$C(═N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S$(O)_2R^h$, —N$R^e$S(O)N$R^fR^g$, —N$R^e$S$(O)_2$N$R^fR^g$, —S$R^e$, —S(O)$R^e$, —S$(O)_2R^e$, —S(O)N$R^fR^g$, and —S$(O)_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an isotopically enriched compound is in a stable form, that is, non-radioactive. In certain embodiments, an isotopically enriched compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an isotopically enriched compound is in an unstable form, that is, radioactive. In certain embodiments, an isotopically enriched compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, as example, or any carbon can be $^{13}C$, as example, or any nitrogen can be $^{15}N$, as example, or any oxygen can be $^{18}O$, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^{1}H$ for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium (H), deuterium ($^{2}H$ or D), and tritium ($^{3}H$), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) an enantiomer, a mixture of enantiomers, a mixture of two or more diastereomers, a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of an enantiomer, a mixture of enantiomers, a mixture of two or more diastereomers, a tautomer, a mixture of two or more tautomers, or an isotopic variant of the compound referenced therein."

Compounds

In one embodiment, provided herein is a compound of Formula A:

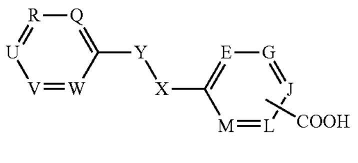

(A)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof;

wherein:

E and Q are each independently a bond, —O—, —S—, —N═, —N($R^A$)—, or —C($R^A$)—;

G, J, L, M, R, U, V, and W are each independently —O—, —S—, —N═, —N($R^A$)—, or —C($R^A$)═;

X is —$SO_2$— and Y is —$CR^XR^Y$— or —N($R^A$)—; or X is —$CR^XR^Y$— and Y is —$SO_2$—;

each $R^A$, $R^X$, and $R^Y$ is independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(═N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(═N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(═N$R^a$)N$R^bR^c$, —OC(S)$R^a$, —OC(S)O$R^a$, —OC(S)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(═N$R^d$)$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(═N$R^e$)N$R^fR^g$, —OC(S)$R^e$, —OC(S)O$R^e$, —OC(S)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$C(═N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R and $R^g$ together with the N atom to which they are attached form heterocyclyl.

In another embodiment, provided herein is a compound of Formula I:

(I)

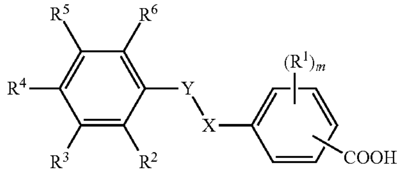

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof;

wherein:

each $R^1$ is independently (a) cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(═N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(═N$R^{1d}$)$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^2$, $R^3$, $R^4$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(═N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)

$NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(O)SR^{1d}$, $-NR^{1a}C(=NR^{1d})NR^{1b}R^{1c}$, $-NR^{1a}C(S)R^{1d}$, $-NR^{1a}C(S)OR^{1d}$, $-NR^{1a}C(S)NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$, or $-S(O)_2NR^{1b}R^{1c}$;

m is an integer of 0, 1, 2, 3, or 4; and $R^{1a}$, $R^{1b}$, $R^{1c}$, $R^{1d}$, X, Y, and Q are each as defined herein.

In yet another embodiment, provided herein is a compound of Formula II:

(II)

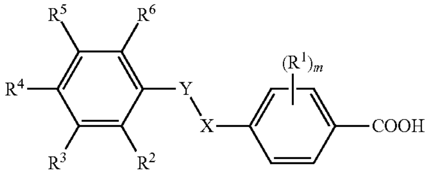

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, X, Y, and m are each as defined herein.

In yet another embodiment, provided herein is a compound of Formula III:

(III)

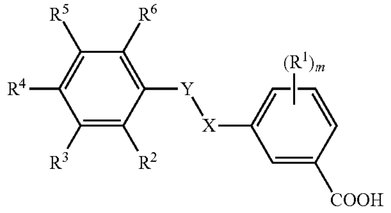

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, X, Y, and m are each as defined herein.

In yet another embodiment, provided herein is a compound of Formula IV:

(IV)

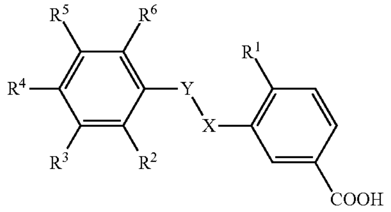

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, X, and Y are each as defined herein.

In yet another embodiment, provided herein is a compound of Formula V:

(V)

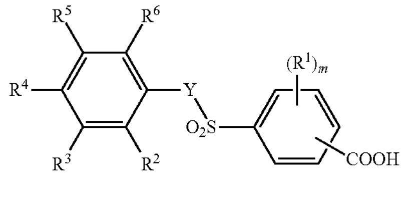

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, Y, and m are each as defined herein.

In yet another embodiment, provided herein is a compound of Formula VI:

(VI)

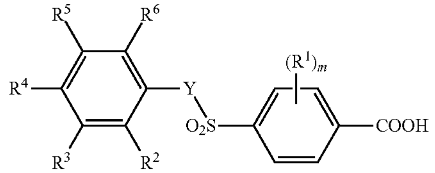

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, Y, and m are each as defined herein.

In yet another embodiment, provided herein is a compound of Formula VII:

(VII)

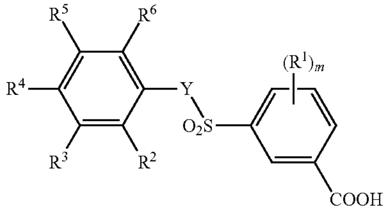

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, Y, and m are each as defined herein.

In yet another embodiment, provided herein is a compound of Formula VIII:

(VIII)

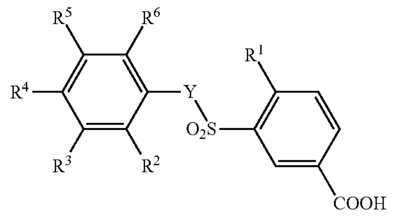

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, and Y are each as defined herein.

In yet another embodiment, provided herein is a compound of Formula IX:

(IX)

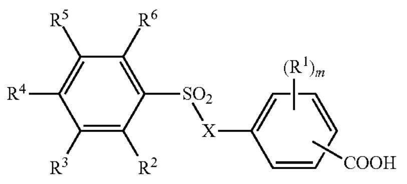

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, X, and m are each as defined herein.

In yet another embodiment, provided herein is a compound of Formula X:

(X)

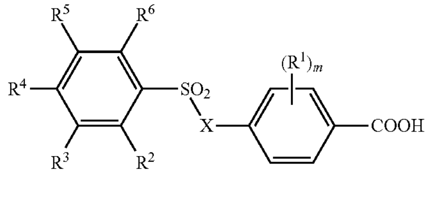

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, X, and m are each as defined herein.

In yet another embodiment, provided herein is a compound of Formula XI:

(XI)

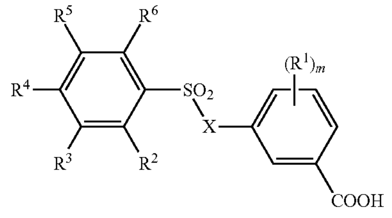

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, X, and m are each as defined herein.

In still another embodiment, provided herein is a compound of Formula XII:

(XII)

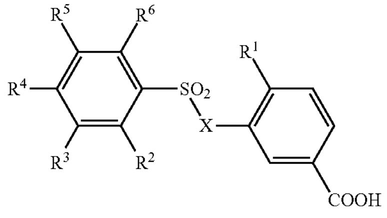

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, and X are each as defined herein.

In one embodiment, in any one of Formulae I to XII, each $R^1$ is independently (a) cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, $C_{1-6}$ alkoxy, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS$(O)_2R^{1a}$, —OS(O)N$R^{1b}R^{1c}$, —OS$(O)_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S$(O)_2R^{1d}$, —N$R^{1a}$S(O)N$R^{1b}R^{1c}$, —N$R^{1a}$S$(O)_2$N$R^{1b}R^{1c}$, —S(O)$R^{1a}$, —S$(O)_2R^{1a}$, —S(O)N$R^{1b}R^{1c}$, or —S$(O)_2$N$R^{1b}R^{1c}$;

$R^2$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS$(O)_2R^{1a}$, —OS(O)N$R^{1b}R^{1c}$, —OS$(O)_2$N$R^{1b}R^{1c}$, —N$R^{1b}R^{1c}$, —N$R^{1a}$C (O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(═NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^3$ is (a) cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)—$C_{1-6}$ alkyl, —C(O)OR$^{1a}$, —C(O)NHR$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(═NR$^{1d}$)R$^{1b}$R$^{1c}$, —NR$^{1a}$C(S)R$^{1d}$, —NR$^{1a}$C(S)OR$^{1d}$, —NR$^{1a}$C(S)R$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^4$ is hydrogen, deuterium, cyano, or fluoro; and m is an integer of 0, 1, 2, 3, or 4;

wherein each alkyl, alkenyl, alkynyl, cycloalkyl, aryl, aralkyl, heteroaryl, and heterocyclyl is independently and optionally substituted with one or more, in one embodiment, one, two, three, or four, substituents Q; and wherein $R^{1a}$, $R^{1b}$, $R^{1c}$, $R^{1d}$, X, Y, and Q are each as defined herein.

In another embodiment, in any one of Formulae I to XII, each $R^1$ is independently (a) cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, $C_{1-6}$ alkoxy, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(═NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^2$ and $R^4$ are each hydrogen;

$R^3$ is (a) cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)—$C_{1-6}$ alkyl, —C(O)OR$^{1a}$, —C(O)NHR$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(═NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^5$ and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(═NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; and m is an integer of 0, 1, 2, 3, or 4;

wherein each alkyl, alkenyl, alkynyl, cycloalkyl, aryl, aralkyl, heteroaryl, and heterocyclyl is independently and optionally substituted with one or more, in one embodiment, one, two, three, or four, substituents Q; and wherein $R^{1a}$, $R^{1b}$, $R^{1c}$, $R^{1d}$, X, Y, and Q are each as defined herein.

In yet another embodiment, in any one of Formulae I to XII, each $R^1$ is independently (a) cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, $C_{1-6}$ alkoxy, —OC(O)R$^{1a}$, —OC(O)OR$^{1a}$, —OC(O)NR$^{1b}$R$^{1c}$, —OC(O)SR$^{1a}$, —OC(═NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(═NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^2$ and $R^4$ are each hydrogen;

$R^3$ is nitro, $C_{1-6}$ alkyl, —OR$^{1a}$, or —NR$^{1a}$S(O)$_2$R$^{1d}$;

$R^5$ is hydrogen or —OR$^{1a}$;

$R^6$ is hydrogen, $C_{1-6}$ alkyl, or —OR$^{1a}$;

X or Y is —CH$_2$—; and m is an integer of 0, 1, 2, or 3;

wherein each alkyl, alkenyl, alkynyl, cycloalkyl, aryl, aralkyl, heteroaryl, and heterocyclyl is independently and optionally substituted with one or more, in one embodiment, one, two, three, or four, substituents Q; and wherein $R^{1a}$, $R^{1b}$, $R^{1c}$, $R^{1d}$, and Q are each as defined herein.

In yet another embodiment, in any one of Formulae I to XII, each $R^1$ is independently halo or $C_{1-6}$ alkyl;

$R^2$ and $R^4$ are each hydrogen;

$R^3$ is nitro, $C_{1-6}$ alkyl, $C_{1-6}$ alkoxy, or $C_{1-6}$ alkylsulfonamido;

$R^5$ is hydrogen or $C_{1-6}$ alkoxy;

$R^6$ is hydrogen, $C_{1-6}$ alkyl, or $C_{1-6}$ alkoxy;

X or Y is —CH$_2$—; and m is an integer of 0, 1, or 2;

wherein each alkyl, alkoxy, and alkylsulfonamido is independently and optionally substituted with one or more, in one embodiment, one, two, three, or four, substituents Q.

In yet another embodiment, in any one of Formulae I to XII, each $R^1$ is independently $C_{1-6}$ alkyl;

$R^2$ and $R^4$ are each hydrogen;

$R^3$ is nitro, $C_{1-6}$ alkyl, $C_{1-6}$ alkoxy, or $C_{1-6}$ alkylsulfonamido;

$R^5$ is hydrogen or $C_{1-6}$ alkoxy;

$R^6$ is hydrogen, $C_{1-6}$ alkyl, or $C_{1-6}$ alkoxy;

X or Y is —$CH_2$—; and m is an integer of 0, 1, or 2;

wherein each alkyl, alkoxy, and alkylsulfonamido is independently and optionally substituted with one or more, in one embodiment, one, two, three, or four, substituents Q.

In yet another embodiment, in any one of Formulae I to XII, $R^1$ is methyl or fluoro;

$R^2$ and $R^4$ are each hydrogen;

$R^3$ is nitro, trifluoromethyl, methoxy, or methylsulfonamido;

$R^5$ is hydrogen or methoxy;

$R^6$ is hydrogen, methyl, or methoxy;

X or Y is —$CH_2$—; and m is an integer of 0 or 1.

In still another embodiment, in any one of Formulae I to XII, $R^1$ is methyl;

$R^2$ and $R^4$ are each hydrogen;

$R^3$ is nitro, trifluoromethyl, methoxy, or methylsulfonamido;

$R^5$ is hydrogen or methoxy;

$R^6$ is hydrogen, methyl, or methoxy;

X or Y is —$CH_2$—; and m is an integer of 0 or 1.

In still another embodiment, in Formulae VII, $R^2$ is hydrogen or fluoro;

$R^3$ is —$OCH_2CH_3$, —$OCH_2CHF_2$, —$OCH_2CF_3$, —$OCH_3$, —$OCHF_2$, or —$OCF_3$;

$R^4$ is hydrogen, fluoro, —C(O)$OCH_3$, —C(O)O-t-butyl, —C(O)N$(CH_3)_2$, or —C(O)—N-piperidine;

$R^5$ is —$OCH_2CH_3$, —$OCH_2CHF_2$, —$OCH_2CF_3$, —$OCH_3$, —$OCHF_2$, or —$OCF_3$;

$R^6$ is hydrogen or fluoro;

X is —$SO_2$—;

Y is —NH—; and m is an integer of 0.

The groups, $R^1$, $R^2$, $R^3$, $R^4$, $R^5$, $R^6$, $R^A$, $R^X$, $R^Y$, E, G, J, L, M, Q, R, U, V, W, X, Y, and m, in formulae described herein, including Formulae A and I to XII, are further defined in the embodiments described herein. All combinations of the embodiments provided herein for such groups are within the scope of this disclosure.

In certain embodiments, $R^1$ is cyano. In certain embodiments, $R^1$ is halo. In certain embodiments, $R^1$ is fluoro, chloro, or bromo. In certain embodiments, $R^1$ is nitro. In certain embodiments, $R^1$ is $C_{1-6}$ alkyl, optionally substituted with one or more substituents Q. In certain embodiments, $R^1$ is methyl, optionally substituted with one or more substituents Q. In certain embodiments, $R^1$ is $C_{2-6}$ alkenyl, optionally substituted with one or more substituents Q. In certain embodiments, $R^1$ is $C_{2-6}$ alkynyl, optionally substituted with one or more substituents Q. In certain embodiments, $R^1$ is $C_{3-10}$ cycloalkyl, optionally substituted with one or more substituents Q. In certain embodiments, $R^1$ is $C_{6-14}$ aryl, optionally substituted with one or more substituents Q. In certain embodiments, $R^1$ is $C_{7-15}$ aralkyl, optionally substituted with one or more substituents Q. In certain embodiments, $R^1$ is benzyl, optionally substituted with one or more substituents Q. In certain embodiments, $R^1$ is heteroaryl, optionally substituted with one or more substituents Q. In certain embodiments, $R^1$ is heterocyclyl, optionally substituted with one or more substituents Q.

In certain embodiments, $R^1$ is —C(O)$R^{1a}$, wherein $R^{1a}$ is as defined herein. In certain embodiments, $R^1$ is —C(O)$OR^{1a}$, wherein $R^{1a}$ is as defined herein. In certain embodiments, $R^1$ is —C(O)$NR^{1b}R^{1c}$, wherein $R^{1b}$ and $R^{1c}$ are each as defined herein. In certain embodiments, $R^1$ is —C(O)$SR^{1a}$, wherein $R^{1a}$ is as defined herein. In certain embodiments, $R^1$ is —C($NR^{1a}$)$NR^{1b}R^{1c}$, wherein $R^{1a}$, $R^{1b}$, and $R^{1c}$ are each as defined herein. In certain embodiments, $R^1$ is —C(S)$R^{1a}$, wherein $R^{1a}$ is as defined herein. In certain embodiments, $R^1$ is —C(S)$OR^{1a}$, wherein $R^{1a}$ is as defined herein. In certain embodiments, $R^1$ is —C(S)$NR^{1b}R^{1c}$, wherein $R^{1b}$ and $R^{1c}$ are each as defined herein. In certain embodiments, $R^1$ is —$OR^{1a}$, wherein $R^{1a}$ is as defined herein. In certain embodiments, $R^1$ is —$OR^{1a}$, wherein $R^{1a}$ is $C_{1-6}$ alkyl, $C_{2-6}$ alkenyl, $C_{2-6}$ alkynyl, $C_{3-10}$ cycloalkyl, $C_{7-15}$ aralkyl, heteroaryl, or heterocyclyl, each optionally substituted with one or more substituents Q. In certain embodiments, $R^1$ is $C_{1-6}$ alkoxy, optionally substituted with one or more substituents Q. In certain embodiments, $R^1$ is —OC(O)$R^{1a}$, wherein $R^{1a}$ is as defined herein. In certain embodiments, $R^1$ is —OC(O)$OR^{1a}$, wherein $R^{1a}$ is as defined herein. In certain embodiments, $R^1$ is —OC(O)$NR^{1b}R^{1c}$, wherein $R^{1b}$ and $R^{1c}$ are each as defined herein. In certain embodiments, $R^1$ is —OC(O)$SR^{1a}$, wherein $R^{1a}$ is as defined herein. In certain embodiments, $R^1$ is —OC(=$NR^{1a}$)$NR^{1b}R^{1c}$, wherein $R^{1a}$, $R^{1b}$, and $R^{1c}$ are each as defined herein. In certain embodiments, $R^1$ is —OC(S)$R^{1a}$, wherein $R^{1a}$ is as defined herein. In certain embodiments, $R^1$ is —OC(S)$OR^{1a}$, wherein $R^{1a}$ is as defined herein. In certain embodiments, $R^1$ is —OC(S)$NR^{1b}R^{1c}$, wherein $R^{1b}$ and $R^{1c}$ are each as defined herein. In certain embodiments, $R^1$ is —OS(O)$R^{1a}$, wherein $R^{1a}$ is as defined herein. In certain embodiments, $R^1$ is —$OS(O)_2R^{1a}$, wherein $R^{1a}$ is as defined herein. In certain embodiments, $R^1$ is —OS(O)$NR^{1b}R^{1c}$, wherein $R^{1b}$ and $R^{1c}$ are each as defined herein. In certain embodiments, $R^1$ is —$OS(O)_2NR^{1b}R^{1c}$, wherein $R^{1b}$ and $R^{1c}$ are each as defined herein. In certain embodiments, $R^1$ is —$NR^{1b}R^{1c}$, wherein $R^{1b}$ and $R^{1c}$ are each as defined herein. In certain embodiments, $R^1$ is —$NR^{1a}$C(O)$R^{1d}$, wherein $R^{1a}$ and $R^{1d}$ are each as defined herein. In certain embodiments, $R^1$ is —$NR^{1a}$C(O)$OR^{1d}$, wherein $R^{1a}$ and $R^{1d}$ are each as defined herein. In certain embodiments, $R^1$ is —$NR^{1a}$C(O)$NR^{1b}R^{1c}$, wherein $R^{1a}$, $R^{1b}$, and $R^{1c}$ are each as defined herein. In certain embodiments, $R^1$ is —$NR^{1a}$C(O)$SR^{1d}$, wherein $R^{1a}$ and $R^{1d}$ are each as defined herein. In certain embodiments, $R^1$ is —$NR^{1a}$C(=$NR^{1d}$)$NR^{1b}R^{1c}$, wherein $R^{1a}$, $R^{1b}$, $R^{1c}$, and $R^{1d}$ are each as defined herein. In certain embodiments, $R^1$ is —$NR^{1a}$C(S)$R^{1d}$, wherein $R^{1a}$ and $R^{1d}$ are each as defined herein. In certain embodiments, $R^1$ is —$NR^{1a}$C(S)$OR^{1d}$, wherein $R^{1a}$ and $R^{1d}$ are each as defined herein. In certain embodiments, $R^1$ is —$NR^{1a}$C(S)$NR^{1b}R^{1c}$, wherein $R^{1a}$, $R^{1b}$, and $R^{1c}$ are each as defined herein. In certain embodiments, $R^1$ is —$NR^{1a}$S(O)$R^{1d}$, wherein $R^{1a}$ and $R^{1d}$ are each as defined herein. In certain embodiments, $R^1$ is —$NR^{1a}S(O)_2R^{1d}$, wherein $R^{1a}$ and $R^{1d}$ are each as defined herein. In certain embodiments, $R^1$ is —$NR^{1a}$S(O)$NR^{1b}R^{1c}$, wherein $R^{1a}$, $R^{1b}$, and $R^{1c}$ are each as defined herein. In certain embodiments, $R^1$ is —$NR^{1a}S(O)_2$ $NR^{1b}R^{1c}$, wherein $R^{1a}$, $R^{1b}$, and $R^{1c}$ are each as defined herein. In certain embodiments, $R^1$ is —S(O)$R^{1a}$, wherein $R^{1a}$ is as defined herein. In certain embodiments, $R^1$ is —$S(O)_2R^{1a}$, wherein $R^{1a}$ is as defined herein. In certain embodiments, $R^1$ is —S(O)$NR^{1b}R^{1c}$, wherein $R^{1b}$ and $R^{1c}$ are each as defined herein. In certain embodiments, $R^1$ is —$S(O)_2NR^{1b}R^{1c}$, wherein $R^{1b}$ and $R^{1c}$ are each as defined herein.

In certain embodiments, $R^2$ is hydrogen. In certain embodiments, $R^2$ is deuterium. In certain embodiments, $R^2$ is cyano. In certain embodiments, $R^2$ is halo. In certain embodiments, $R^2$ is fluoro, chloro, or bromo. In certain embodiments, $R^2$ is fluoro. In certain embodiments, $R^2$ is chloro. In certain embodiments, $R^2$ is nitro. In certain embodiments, $R^2$ is $C_{1-6}$ alkyl, optionally substituted with one or more substituents Q. In certain embodiments, $R^2$ is methyl, optionally substituted with one or more substituents Q. In certain embodiments, $R^2$ is $C_{2-6}$ alkenyl, optionally substituted with one or more substituents Q. In certain embodiments, $R^2$ is $C_{2-6}$ alkynyl, optionally substituted with one or more substituents Q. In certain embodiments, $R^2$ is $C_{3-10}$ cycloalkyl, optionally substituted with one or more substituents Q. In certain embodiments, $R^2$ is $C_{6-14}$ aryl, optionally substituted with one or more substituents Q. In certain embodiments, $R^2$ is $C_{7-15}$ aralkyl, optionally substituted with one or more substituents Q. In certain embodiments, $R^2$ is heteroaryl, optionally substituted with one or more substituents Q. In certain embodiments, $R^2$ is heterocyclyl, optionally substituted with one or more substituents Q.

In certain embodiments, $R^2$ is —C(O)$R^{1a}$, wherein $R^{1a}$ is as defined herein. In certain embodiments, $R^2$ is —C(O)$OR^{1a}$, wherein $R^{1a}$ is as defined herein. In certain embodiments, $R^2$ is —C(O)$NR^{1b}R^{1c}$, wherein $R^{1b}$ and $R^{1c}$ are each as defined herein. In certain embodiments, $R^2$ is —C(O)$SR^{1a}$, wherein $R^{1a}$ is as defined herein. In certain embodiments, $R^2$ is —C($NR^{1a}$)$NR^{1b}R^{1c}$, wherein $R^{1a}$, $R^{1b}$, and $R^{1c}$ are each as defined herein. In certain embodiments, $R^2$ is —C(S)$R^{1a}$, wherein $R^{1a}$ is as defined herein. In certain embodiments, $R^2$ is —C(S)$OR^{1a}$, wherein $R^{1a}$ is as defined herein. In certain embodiments, $R^2$ is —C(S)$NR^{1b}R^{1c}$, wherein $R^{1b}$ and $R^{1c}$ are each as defined herein. In certain embodiments, $R^2$ is —$OR^{1a}$, wherein $R^{1a}$ is as defined herein. In certain embodiments, $R^2$ is $C_{1-6}$ alkoxy, optionally substituted with one or more substituents Q. In certain embodiments, $R^2$ is methoxy, optionally substituted with one or more substituents Q. In certain embodiments, $R^2$ is —OC(O)$R^{1a}$, wherein $R^{1a}$ is as defined herein. In certain embodiments, $R^2$ is —OC(O)$OR^{1a}$, wherein $R^{1a}$ is as defined herein. In certain embodiments, $R^2$ is —OC(O)$NR^{1b}R^{1c}$, wherein $R^{1b}$ and $R^{1c}$ are each as defined herein. In certain embodiments, $R^2$ is —OC(O)$SR^{1a}$, wherein $R^{1a}$ is as defined herein. In certain embodiments, $R^2$ is —OC(=$NR^{1a}$)$NR^{1b}R^{1c}$, wherein $R^{1a}$, $R^{1b}$, and $R^{1c}$ are each as defined herein. In certain embodiments, $R^2$ is —OC(S)$R^{1a}$, wherein $R^{1a}$ is as defined herein. In certain embodiments, $R^2$ is —OC(S)$OR^{1a}$, wherein $R^{1a}$ is as defined herein. In certain embodiments, $R^2$ is —OC(S)$NR^{1b}R^{1c}$, wherein $R^{1b}$ and $R^{1c}$ are each as defined herein. In certain embodiments, $R^2$ is —OS(O)$R^{1a}$, wherein $R^{1a}$ is as defined herein. In certain embodiments, $R^2$ is —$OS(O)_2R^{1a}$, wherein $R^{1a}$ is as defined herein. In certain embodiments, $R^2$ is —OS(O)$NR^{1b}R^{1c}$, wherein $R^{1b}$ and $R^{1c}$ are each as defined herein. In certain embodiments, $R^2$ is —$OS(O)_2NR^{1b}R^{1c}$, wherein $R^{1b}$ and $R^{1c}$ are each as defined herein. In certain embodiments, $R^2$ is —$NR^{1b}R^{1c}$, wherein $R^{1b}$ and $R^{1c}$ are each as defined herein. In certain embodiments, $R^2$ is —$NR^{1a}$C(O)$R^{1d}$, wherein $R^{1a}$ and $R^{1d}$ are each as defined herein. In certain embodiments, $R^2$ is —$NR^{1a}$C(O)$OR^{1d}$, wherein $R^{1a}$ and $R^{1d}$ are each as defined herein. In certain embodiments, $R^2$ is —$NR^{1a}$C(O)$NR^{1b}R^{1c}$, wherein $R^{1a}$, $R^{1b}$, and $R^{1c}$ are each as defined herein. In certain embodiments, $R^2$ is —$NR^{1a}$C(O)$SR^{1d}$, wherein $R^{1a}$ and $R^{1d}$ are each as defined herein. In certain embodiments, $R^2$ is —$NR^{1a}$C(=$NR^{1d}$)$NR^{1b}R^{1c}$, wherein $R^{1a}$, $R^{1b}$, $R^{1c}$, and $R^{1d}$ are each as defined herein. In certain embodiments, $R^2$ is —$NR^{1a}$C(S)$R^{1d}$, wherein $R^{1a}$ and $R^{1d}$ are each as defined herein. In certain embodiments, $R^2$ is —$NR^{1a}$C(S)$OR^{1d}$, wherein $R^{1a}$ and $R^{1d}$ are each as defined herein. In certain embodiments, $R^2$ is —$NR^{1a}$C(S)$NR^{1b}R^{1c}$, wherein $R^{1a}$, $R^{1b}$, and $R^{1c}$ are each as defined herein. In certain embodiments, $R^2$ is —$NR^{1a}$S(O)$R^{1d}$, wherein $R^{1a}$ and $R^{1d}$ are each as defined herein. In certain embodiments, $R^2$ is —$NR^{1a}S(O)_2R^{1d}$, wherein $R^{1a}$ and $R^{1d}$ are each as defined herein. In certain embodiments, $R^2$ is —$NR^{1a}$S(O)$NR^{1b}R^{1c}$, wherein $R^{1a}$, $R^{1b}$, and $R^{1c}$ are each as defined herein. In certain embodiments, $R^2$ is —$NR^{1a}S(O)_2NR^{1b}R^{1c}$, wherein $R^{1a}$, $R^{1b}$, and $R^{1c}$ are each as defined herein. In certain embodiments, $R^2$ is —S(O)$R^{1a}$, wherein $R^{1a}$ is as defined herein. In certain embodiments, $R^2$ is —$S(O)_2R^{1a}$, wherein $R^{1a}$ is as defined herein. In certain embodiments, $R^2$ is —S(O)$NR^{1b}R^{1c}$, wherein $R^{1b}$ and $R^{1c}$ are each as defined herein. In certain embodiments, $R^2$ is —$S(O)_2NR^{1b}R^{1c}$, wherein $R^{1b}$ and $R^{1c}$ are each as defined herein.

In certain embodiments, $R^3$ is cyano. In certain embodiments, $R^3$ is halo. In certain embodiments, $R^3$ is fluoro, chloro, or bromo. In certain embodiments, $R^3$ is chloro. In certain embodiments, $R^3$ is nitro. In certain embodiments, $R^3$ is $C_{1-6}$ alkyl, optionally substituted with one or more substituents Q. In certain embodiments, $R^3$ is methyl, optionally substituted with one or more substituents Q. In certain embodiments, $R^3$ is monofluoromethyl, difluoromethyl, or trifluoromethyl. In certain embodiments, $R^3$ is trifluoromethyl. In certain embodiments, $R^3$ is $C_{2-6}$ alkenyl, optionally substituted with one or more substituents Q. In certain embodiments, $R^3$ is $C_{2-6}$ alkynyl, optionally substituted with one or more substituents Q. In certain embodiments, $R^3$ is $C_{3-10}$ cycloalkyl, optionally substituted with one or more substituents Q. In certain embodiments, $R^3$ is $C_{6-14}$ aryl, optionally substituted with one or more substituents Q. In certain embodiments, $R^3$ is $C_{7-15}$ aralkyl, optionally substituted with one or more substituents Q. In certain embodiments, $R^3$ is heteroaryl, optionally substituted with one or more substituents Q. In certain embodiments, $R^3$ is heterocyclyl, optionally substituted with one or more substituents Q.

In certain embodiments, $R^3$ is —C(O)$R^{1a}$, wherein $R^{1a}$ is as defined herein. In certain embodiments, $R^3$ is —C(O)$R^{1a}$, wherein $R^{1a}$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl, each optionally substituted with one or more substituents Q. In certain embodiments, $R^3$ is —C(O)$OR^{1a}$, wherein $R^{1a}$ is as defined herein. In certain embodiments, $R^3$ is —C(O)$NR^{1b}R^{1c}$, wherein $R^{1b}$ and $R^{1c}$ are each as defined herein. In certain embodiments, $R^3$ is —C(O)$NR^{1b}R^{1c}$, wherein $R^{1b}$ and $R^{1c}$ are each independently (i) hydrogen; or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents Q. In certain embodiments, $R^3$ is —C(O)$SR^{1a}$, wherein $R^{1a}$ is as defined herein. In certain embodiments, $R^3$ is —C($NR^{1a}$)$NR^{1b}R^{1c}$, wherein $R^{1a}$, $R^{1b}$, and $R^{1c}$ are each as defined herein. In certain embodiments, $R^3$ is —C(S)$R^{1a}$, wherein $R^{1a}$ is as defined herein. In certain embodiments, $R^3$ is —C(S)$OR^{1a}$, wherein $R^{1a}$ is as defined herein. In certain embodiments, $R^3$ is —C(S)$NR^{1b}R^{1c}$, wherein $R^{1b}$ and $R^{1c}$ are each as defined herein. In certain embodiments, $R^3$ is —$OR^{1a}$, wherein $R^{1a}$ is as defined herein. In certain embodiments, $R^3$ is —$OCH_2CH_3$, —$OCH_2CHF_2$, —$OCH_2CF_3$, —$OCH_3$, —$OCHF_2$, or —$OCF_3$. In certain embodiments, $R^3$ is $C_{1-6}$ alkoxy, optionally substituted with one or more substituents Q. In certain embodiments, $R^3$ is methoxy, optionally substituted with one or more substituents Q. In certain embodiments, $R^3$ is —OC(O)$R^{1a}$, wherein $R^{1a}$ is as defined herein. In certain embodiments, $R^3$ is —OC(O)$OR^{1a}$, wherein $R^{1a}$ is as defined herein. In certain embodiments, $R^3$ is —OC(O)$NR^{1b}R^{1c}$, wherein $R^{1b}$ and $R^{1c}$ are each as defined herein. In certain embodiments, $R^3$ is —OC(O)$SR^{1a}$, wherein $R^{1a}$ is as defined herein. In certain embodiments, $R^3$ is —OC(=$NR^{1a}$)$NR^{1b}R^{1c}$, wherein $R^{1a}$, $R^{1b}$, and $R^{1c}$ are each as defined herein. In certain embodiments, $R^3$ is —OC(S)$R^{1a}$, wherein $R^{1a}$ is as defined herein. In certain embodiments, $R^3$ is —OC(S)$OR^{1a}$, wherein $R^{1a}$ is as defined herein. In certain embodiments, $R^3$ is —OC(S)$NR^{1b}R^{1c}$, wherein $R^{1b}$ and $R^{1c}$ are each as defined herein. In certain embodiments, $R^3$ is —OS(O)$R^{1a}$, wherein $R^{1a}$ is as defined herein. In certain embodiments, $R^3$ is —$OS(O)_2R^{1a}$, wherein $R^{1a}$ is as defined herein. In certain embodiments, $R^3$ is —OS(O)$NR^{1b}R^{1c}$, wherein $R^{1b}$ and $R^{1c}$ are each as defined herein. In certain embodiments, $R^3$ is —$OS(O)_2NR^{1b}R^{1c}$, wherein $R^{1b}$ and $R^{1c}$ are each as defined herein. In certain embodiments, $R^3$ is —$NR^{1b}R^{1c}$, wherein $R^{1b}$ and $R^{1c}$ are each as defined herein. In certain embodiments, $R^3$ is —$NR^{1a}C(O)R^{1d}$, wherein $R^{1a}$ and $R^{1d}$ are each as defined herein. In certain embodiments, $R^3$ is —$NR^{1a}C(O)OR^{1d}$, wherein $R^{1a}$ and $R^{1d}$ are each as defined herein. In certain embodiments, $R^3$ is —$NR^{1a}C(O)NR^{1b}R^{1c}$, wherein $R^{1a}$, $R^{1b}$, and $R^{1c}$ are each as defined herein. In certain embodiments, $R^3$ is —$NR^{1a}C(O)SR^{1d}$, wherein $R^{1a}$ and $R^{1d}$ are each as defined herein. In certain embodiments, $R^3$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^3$ is —$NR^{1a}C(S)R^{1d}$, wherein $R^{1a}$ and $R^{1d}$ are each as defined herein. In certain embodiments, $R^3$ is —$NR^{1a}C(S)OR^{1d}$, wherein $R^{1a}$ and $R^{1d}$ are each as defined herein. In certain embodiments, $R^3$ is —$NR^{1a}C(S)NR^{1b}R^{1c}$, wherein $R^{1a}$, $R^{1b}$, and $R^{1c}$ are each as defined herein. In certain embodiments, $R^3$ is —$NR^{1a}S(O)R^{1d}$, wherein $R^{1a}$ and $R^{1d}$ are each as defined herein. In certain embodiments, $R^3$ is —$NR^{1a}S(O)_2R^{1d}$, wherein $R^{1a}$ and $R^{1d}$ are each as defined herein. In certain embodiments, $R^3$ is $C_{1-6}$ alkylsulfonamide, optionally substituted with one or more substituents Q. In certain embodiments, $R^3$ is —$NR^{1a}S(O)NR^{1b}R^{1c}$, wherein $R^{1a}$, $R^{1b}$, and $R^{1c}$ are each as defined herein. In certain embodiments, $R^3$ is —$NR^{1a}S(O)_2NR^{1b}R^{1c}$, wherein $R^{1a}$, $R^{1b}$, and $R^{1c}$ are each as defined herein. In certain embodiments, $R^3$ is —S(O)$R^{1a}$, wherein $R^{1a}$ is as defined herein. In certain embodiments, $R^3$ is —$S(O)_2R^{1a}$, wherein $R^{1a}$ is as defined herein. In certain embodiments, $R^3$ is —S(O)$NR^{1b}R^{1c}$, wherein $R^{1b}$ and $R^{1c}$ are each as defined herein. In certain embodiments, $R^3$ is —$S(O)_2NR^{1b}R^{1c}$, wherein $R^{1b}$ and $R^{1c}$ are each as defined herein.

In certain embodiments, $R^4$ is hydrogen. In certain embodiments, $R^4$ is deuterium. In certain embodiments, $R^4$ is cyano. In certain embodiments, $R^4$ is halo. In certain embodiments, $R^4$ is fluoro, chloro, or bromo. In certain embodiments, $R^4$ is fluoro. In certain embodiments, $R^4$ is chloro. In certain embodiments, $R^4$ is nitro. In certain embodiments, $R^4$ is $C_{1-6}$ alkyl, optionally substituted with one or more substituents Q. In certain embodiments, $R^4$ is methyl, optionally substituted with one or more substituents Q. In certain embodiments, $R^4$ is $C_{2-6}$ alkenyl, optionally substituted with one or more substituents Q. In certain embodiments, $R^4$ is $C_{2-6}$ alkynyl, optionally substituted with one or more substituents Q. In certain embodiments, $R^4$ is $C_{3-10}$ cycloalkyl, optionally substituted with one or more substituents Q. In certain embodiments, $R^4$ is $C_{6-14}$ aryl, optionally substituted with one or more substituents Q. In certain embodiments, $R^4$ is $C_{7-15}$ aralkyl, optionally substituted with one or more substituents Q. In certain embodiments, $R^4$ is heteroaryl, optionally substituted with one or more substituents Q. In certain embodiments, $R^4$ is heterocyclyl, optionally substituted with one or more substituents Q.

In certain embodiments, $R^4$ is —C(O)$R^{1a}$, wherein $R^{1a}$ is as defined herein. In certain embodiments, $R^4$ is —C(O)$OR^{1a}$, wherein $R^{1a}$ is as defined herein. In certain embodiments, $R^4$ is —C(O)$OCH_3$ or —C(O)O-t-butyl. In certain embodiments, $R^4$ is —C(O)$NR^{1b}R^{1c}$, wherein $R^{1b}$ and $R^{1c}$ are each as defined herein. In certain embodiments, $R^4$ is —C(O)$N(CH_3)_2$ or —C(O)—N-piperidine. In certain embodiments, $R^4$ is —C(O)$SR^{1a}$, wherein $R^{1a}$ is as defined herein. In certain embodiments, $R^4$ is —C($NR^{1a}$)$NR^{1b}R^{1c}$, wherein $R^{1a}$, $R^{1b}$, and $R^{1c}$ are each as defined herein. In certain embodiments, $R^4$ is —C(S)$R^{1a}$, wherein $R^{1a}$ is as defined herein. In certain embodiments, $R^4$ is —C(S)$OR^{1a}$, wherein $R^{1a}$ is as defined herein. In certain embodiments, $R^4$ is —C(S)$NR^{1b}R^{1c}$, wherein $R^{1b}$ and $R^{1c}$ are each as defined herein. In certain embodiments, $R^4$ is —$OR^{1a}$, wherein $R^{1a}$ is as defined herein. In certain embodiments, $R^4$ is $C_{1-6}$ alkoxy, optionally substituted with one or more substituents Q. In certain embodiments, $R^4$ is methoxy, optionally substituted with one or more substituents Q. In certain embodiments, $R^4$ is —OC(O)$R^{1a}$, wherein $R^{1a}$ is as defined herein. In certain embodiments, $R^4$ is —OC(O)$OR^{1a}$, wherein $R^{1a}$ is as defined herein. In certain embodiments, $R^4$ is —OC(O)$NR^{1b}R^{1c}$, wherein $R^{1b}$ and $R^{1c}$ are each as defined herein. In certain embodiments, $R^4$ is —OC(O)$SR^{1a}$, wherein $R^{1a}$ is as defined herein. In certain embodiments, $R^4$ is —OC(=$NR^{1a}$)$NR^{1b}R^{1c}$, wherein $R^{1a}$, $R^{1b}$, and $R^{1c}$ are each as defined herein. In certain embodiments, $R^4$ is —OC(S)$R^{1a}$, wherein $R^{1a}$ is as defined herein. In certain embodiments, $R^4$ is —OC(S)$OR^{1a}$, wherein $R^{1a}$ is as defined herein. In certain embodiments, $R^4$ is —OC(S)$NR^{1b}R^{1c}$, wherein $R^{1b}$ and $R^{1c}$ are each as defined herein. In certain embodiments, $R^4$ is —OS(O)$R^{1a}$, wherein $R^{1a}$ is as defined herein. In certain embodiments, $R^4$ is —$OS(O)_2R^{1a}$, wherein $R^{1a}$ is as defined herein. In certain embodiments, $R^4$ is —OS(O)$NR^{1b}R^{1c}$, wherein $R^{1b}$ and $R^{1c}$ are each as defined herein. In certain embodiments, $R^4$ is —$OS(O)_2NR^{1b}R^{1c}$, wherein $R^{1b}$ and $R^{1c}$ are each as defined herein. In certain embodiments, $R^4$ is —$NR^{1b}R^{1c}$, wherein $R^{1b}$ and $R^{1c}$ are each as defined herein. In certain embodiments, $R^4$ is —$NR^{1a}C(O)R^{1d}$, wherein $R^{1a}$ and $R^{1d}$ are each as defined herein. In certain embodiments, $R^4$ is —$NR^{1a}C(O)OR^{1d}$, wherein $R^{1a}$ and $R^{1d}$ are each as defined herein. In certain embodiments, $R^4$ is —$NR^{1a}C(O)NR^{1b}R^{1c}$, wherein $R^{1a}$, $R^{1b}$, and $R^{1c}$ are each as defined herein. In certain embodiments, $R^4$ is —$NR^{1a}C(O)SR^{1d}$, wherein $R^{1a}$ and $R^{1d}$ are each as defined herein. In certain embodiments, $R^4$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^4$ is —$NR^{1a}C(S)R^{1d}$, wherein $R^{1a}$ and $R^{1d}$ are each as defined herein. In certain embodiments, $R^4$ is —$NR^{1a}C(S)OR^{1d}$, wherein $R^{1a}$ and $R^{1d}$ are each as defined herein. In certain embodiments, $R^4$ is —$NR^{1a}C(S)NR^{1b}R^{1c}$, wherein $R^{1a}$, $R^{1b}$, and $R^{1c}$ are each as defined herein. In certain embodiments, $R^4$ is —$NR^{1a}S(O)R^{1d}$, wherein $R^{1a}$ and $R^{1d}$ are each as defined herein. In certain embodiments, $R^4$ is —$NR^{1a}S(O)_2R^{1d}$, wherein $R^{1a}$ and $R^{1d}$ are each as defined herein. In certain embodiments, $R^4$ is —$NR^{1a}S(O)NR^{1b}R^{1c}$, wherein $R^{1a}$, $R^{1b}$, and $R^{1c}$ are each as defined herein. In certain embodiments, $R^4$ is —$NR^{1a}S(O)_2NR^{1b}R^{1c}$, wherein $R^{1a}$, $R^{1b}$, and $R^{1c}$ are each as defined herein. In certain embodiments, $R^4$ is —$S(O)R^{1a}$, wherein $R^{1a}$ is as defined herein. In certain embodiments, $R^4$ is —$S(O)_2R^{1a}$, wherein $R^{1a}$ is as defined herein. In certain embodiments, $R^4$ is —$S(O)NR^{1b}R^{1c}$, wherein $R^{1b}$ and $R^{1c}$ are each as defined herein. In certain embodiments, $R^4$ is —$S(O)_2NR^{1b}R^{1c}$, wherein $R^{1b}$ and $R^{1c}$ are each as defined herein.

In certain embodiments, $R^5$ is hydrogen. In certain embodiments, $R^5$ is deuterium. In certain embodiments, $R^5$ is cyano. In certain embodiments, $R^5$ is halo. In certain embodiments, $R^5$ is fluoro, chloro, or bromo. In certain embodiments, $R^5$ is chloro. In certain embodiments, $R^5$ is nitro. In certain embodiments, $R^5$ is $C_{1-6}$ alkyl, optionally substituted with one or more substituents Q. In certain embodiments, $R^5$ is methyl, optionally substituted with one or more substituents Q. In certain embodiments, $R^5$ is $C_{2-6}$ alkenyl, optionally substituted with one or more substituents Q. In certain embodiments, $R^5$ is $C_{2-6}$ alkynyl, optionally substituted with one or more substituents Q. In certain embodiments, $R^5$ is $C_{3-10}$ cycloalkyl, optionally substituted with one or more substituents Q. In certain embodiments, $R^5$ is $C_{6-14}$ aryl, optionally substituted with one or more substituents Q. In certain embodiments, $R^5$ is $C_{7-15}$ aralkyl, optionally substituted with one or more substituents Q. In certain embodiments, $R^5$ is heteroaryl, optionally substituted with one or more substituents Q. In certain embodiments, $R^5$ is heterocyclyl, optionally substituted with one or more substituents Q.

In certain embodiments, $R^5$ is —$C(O)R^{1a}$, wherein $R^{1a}$ is as defined herein. In certain embodiments, $R^5$ is —$C(O)OR^{1a}$, wherein $R^{1a}$ is as defined herein. In certain embodiments, $R^5$ is —$C(O)NR^{1b}R^{1c}$, wherein $R^{1b}$ and $R^{1c}$ are each as defined herein. In certain embodiments, $R^5$ is —$C(O)SR^{1a}$, wherein $R^{1a}$ is as defined herein. In certain embodiments, $R^5$ is —$C(NR^{1a})NR^{1b}R^{1c}$, wherein $R^{1a}$, $R^{1b}$, and $R^{1c}$ are each as defined herein. In certain embodiments, $R^5$ is —$C(S)R^{1a}$, wherein $R^{1a}$ is as defined herein. In certain embodiments, $R^5$ is —$C(S)OR^{1a}$, wherein $R^{1a}$ is as defined herein. In certain embodiments, $R^5$ is —$C(S)NR^{1b}R^{1c}$, wherein $R^{1b}$ and $R^{1c}$ are each as defined herein. In certain embodiments, $R^5$ is —$OR^{1a}$, wherein $R^{1a}$ is as defined herein. In certain embodiments, $R^5$ is —$OCH_2CH_3$, —$OCH_2CHF_2$, —$OCH_2CF_3$, —$OCH_3$, —$OCHF_2$, or —$OCF_3$. In certain embodiments, $R^5$ is $C_{1-6}$ alkoxy, optionally substituted with one or more substituents Q. In certain embodiments, $R^5$ is methoxy, optionally substituted with one or more substituents Q. In certain embodiments, $R^5$ is —$OC(O)R^{1a}$, wherein $R^{1a}$ is as defined herein. In certain embodiments, $R^5$ is —$OC(O)OR^{1a}$, wherein $R^{1a}$ is as defined herein. In certain embodiments, $R^5$ is —$OC(O)NR^{1b}R^{1c}$, wherein $R^{1b}$ and $R^{1c}$ are each as defined herein. In certain embodiments, $R^5$ is —$OC(O)SR^{1a}$, wherein $R^{1a}$ is as defined herein. In certain embodiments, $R^5$ is —$OC(=NR^{1a})NR^{1b}R^{1c}$, wherein $R^{1a}$, $R^{1b}$, and $R^{1c}$ are each as defined herein. In certain embodiments, $R^5$ is —$OC(S)R^{1a}$, wherein $R^{1a}$ is as defined herein. In certain embodiments, $R^5$ is —$OC(S)OR^{1a}$, wherein $R^{1a}$ is as defined herein. In certain embodiments, $R^5$ is —$OC(S)NR^{1b}R^{1c}$, wherein $R^{1b}$ and $R^{1c}$ are each as defined herein. In certain embodiments, $R^5$ is —$OS(O)R^{1a}$, wherein $R^{1a}$ is as defined herein. In certain embodiments, $R^5$ is —$OS(O)_2R^{1a}$, wherein $R^{1a}$ is as defined herein. In certain embodiments, $R^5$ is —$OS(O)NR^{1b}R^{1c}$, wherein $R^{1b}$ and $R^{1c}$ are each as defined herein. In certain embodiments, $R^5$ is —$OS(O)_2NR^{1b}R^{1c}$, wherein $R^{1b}$ and $R^{1c}$ are each as defined herein. In certain embodiments, $R^5$ is —$NR^{1b}R^{1c}$, wherein $R^{1b}$ and $R^{1c}$ are each as defined herein. In certain embodiments, $R^5$ is —$NR^{1a}C(O)R^{1d}$, wherein $R^{1a}$ and $R^{1d}$ are each as defined herein. In certain embodiments, $R^5$ is —$NR^{1a}C(O)OR^{1d}$, wherein $R^{1a}$ and $R^{1d}$ are each as defined herein. In certain embodiments, $R^5$ is —$NR^{1a}C(O)NR^{1b}R^{1c}$, wherein $R^{1a}$, $R^{1b}$, and $R^{1c}$ are each as defined herein. In certain embodiments, $R^5$ is —$NR^{1a}C(O)SR^{1d}$, wherein $R^{1a}$ and $R^{1d}$ are each as defined herein. In certain embodiments, $R^5$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^5$ is —$NR^{1a}C(S)R^{1d}$, wherein $R^{1a}$ and $R^{1d}$ are each as defined herein. In certain embodiments, $R^5$ is —$NR^{1a}C(S)OR^{1d}$, wherein $R^{1a}$ and $R^{1d}$ are each as defined herein. In certain embodiments, $R^5$ is —$NR^{1a}C(S)NR^{1b}R^{1c}$, wherein $R^{1a}$, $R^{1b}$, and $R^{1c}$ are each as defined herein. In certain embodiments, $R^5$ is —$NR^{1a}S(O)R^{1d}$, wherein $R^{1a}$ and $R^{1d}$ are each as defined herein. In certain embodiments, $R^5$ is —$NR^{1a}S(O)_2R^{1d}$, wherein $R^{1a}$ and $R^{1d}$ are each as defined herein. In certain embodiments, $R^5$ is —$NR^{1a}S(O)NR^{1b}R^{1c}$, wherein $R^{1a}$, $R^{1b}$, and $R^{1c}$ are each as defined herein. In certain embodiments, $R^5$ is —$NR^{1a}S(O)_2NR^{1b}R^{1c}$, wherein $R^{1a}$, $R^{1b}$, and $R^{1c}$ are each as defined herein. In certain embodiments, $R^5$ is —$S(O)R^{1a}$, wherein $R^{1a}$ is as defined herein. In certain embodiments, $R^5$ is —$S(O)_2R^{1a}$, wherein $R^{1a}$ is as defined herein. In certain embodiments, $R^5$ is —$S(O)NR^{1b}R^{1c}$, wherein $R^{1b}$ and $R^{1c}$ are each as defined herein. In certain embodiments, $R^5$ is —$S(O)_2NR^{1b}R^{1c}$, wherein $R^{1b}$ and $R^{1c}$ are each as defined herein.

In certain embodiments, $R^6$ is hydrogen. In certain embodiments, $R^6$ is deuterium. In certain embodiments, $R^6$ is cyano. In certain embodiments, $R^6$ is halo. In certain embodiments, $R^6$ is fluoro, chloro, or bromo. In certain embodiments, $R^6$ is fluoro. In certain embodiments, $R^6$ is chloro. In certain embodiments, $R^6$ is nitro. In certain embodiments, $R^6$ is $C_{1-6}$ alkyl, optionally substituted with one or more substituents Q. In certain embodiments, $R^6$ is methyl, optionally substituted with one or more substituents Q. In certain embodiments, $R^6$ is $C_{2-6}$ alkenyl, optionally substituted with one or more substituents Q. In certain embodiments, $R^6$ is $C_{2-6}$ alkynyl, optionally substituted with one or more substituents Q. In certain embodiments, $R^6$ is $C_{3-10}$ cycloalkyl, optionally substituted with one or more substituents Q. In certain embodiments, $R^6$ is $C_{6-14}$ aryl, optionally substituted with one or more substituents Q. In certain embodiments, $R^6$ is $C_{7-15}$ aralkyl, optionally substituted with one or more substituents Q. In certain embodiments, $R^6$ is heteroaryl, optionally substituted with one or more substituents Q. In certain embodiments, $R^6$ is heterocyclyl, optionally substituted with one or more substituents Q.

In certain embodiments, $R^6$ is —$C(O)R^{1a}$, wherein $R^{1a}$ is as defined herein. In certain embodiments, $R^6$ is —$C(O)OR^{1a}$, wherein $R^{1a}$ is as defined herein. In certain embodiments, $R^6$ is —$C(O)NR^{1b}R^{1c}$, wherein $R^{1b}$ and $R^{1c}$ are each as defined herein. In certain embodiments, $R^6$ is —$C(O)SR^{1a}$, wherein $R^{1a}$ is as defined herein. In certain embodiments, $R^6$ is —$C(NR^{1a})NR^{1b}R^{1c}$, wherein $R^{1a}$, $R^{1b}$, and $R^{1c}$ are each as defined herein. In certain embodiments, $R^6$ is —$C(S)R^{1a}$, wherein $R^{1a}$ is as defined herein. In certain embodiments, $R^6$ is —$C(S)OR^{1a}$, wherein $R^{1a}$ is as defined herein. In certain embodiments, $R^6$ is —$C(S)NR^{1b}R^{1c}$, wherein $R^{1b}$ and $R^{1c}$ are each as defined herein. In certain embodiments, $R^6$ is —$OR^{1a}$, wherein $R^{1a}$ is as defined herein. In certain embodiments, $R^6$ is —OC(O)$R^{1a}$, wherein $R^{1a}$ is as defined herein. In certain embodiments, $R^6$ is —OC(O)O$R^{1a}$, wherein $R^{1a}$ is as defined herein. In certain embodiments, $R^6$ is —OC(O)N$R^{1b}R^{1c}$, wherein $R^{1b}$ and $R^{1c}$ are each as defined herein. In certain embodiments, $R^6$ is —OC(O)S$R^{1a}$, wherein $R^{1a}$ is as defined herein. In certain embodiments, $R^6$ is —OC(═N$R^{1a}$)N$R^{1b}R^{1c}$, wherein $R^{1a}$, $R^{1b}$, and $R^{1c}$ are each as defined herein. In certain embodiments, $R^6$ is —OC(S)$R^{1a}$, wherein $R^{1a}$ is as defined herein. In certain embodiments, $R^6$ is —OC(S)O$R^{1a}$, wherein $R^{1a}$ is as defined herein. In certain embodiments, $R^6$ is —OC(S)N$R^{1b}R^{1c}$, wherein $R^{1b}$ and $R^{1c}$ are each as defined herein. In certain embodiments, $R^6$ is —OS(O)$R^{1a}$, wherein $R^{1a}$ is as defined herein. In certain embodiments, $R^6$ is —OS$(O)_2R^{1a}$, wherein $R^{1a}$ is as defined herein. In certain embodiments, $R^6$ is —OS(O)N$R^{1b}R^{1c}$, wherein $R^{1b}$ and $R^{1c}$ are each as defined herein. In certain embodiments, $R^6$ is —OS$(O)_2$N$R^{1b}R^{1c}$, wherein $R^{1b}$ and $R^{1c}$ are each as defined herein. In certain embodiments, $R^6$ is —N$R^{1b}R^{1c}$, wherein $R^{1b}$ and $R^{1c}$ are each as defined herein. In certain embodiments, $R^6$ is —N$R^{1a}$C(O)$R^{1d}$, wherein $R^{1a}$ and $R^{1d}$ are each as defined herein. In certain embodiments, $R^6$ is —N$R^{1a}$C(O)O$R^{1d}$, wherein $R^{1a}$ and $R^{1d}$ are each as defined herein. In certain embodiments, $R^6$ is —N$R^{1a}$C(O)N$R^{1b}R^{1c}$, wherein $R^{1a}$, $R^{1b}$, and $R^{1c}$ are each as defined herein. In certain embodiments, $R^6$ is —N$R^{1a}$C(O)S$R^{1d}$, wherein $R^{1a}$ and $R^{1d}$ are each as defined herein. In certain embodiments, $R^6$ is —N$R^{1a}$C(═N$R^{1d}$)N$R^{1b}R^{1c}$, wherein $R^{1a}$, $R^{1b}$, $R^{1c}$, and $R^{1d}$ are each as defined herein. In certain embodiments, $R^6$ is —N$R^{1a}$C(S)$R^{1d}$, wherein $R^{1a}$ and $R^{1d}$ are each as defined herein. In certain embodiments, $R^6$ is —N$R^{1a}$C(S)O$R^{1d}$, wherein $R^{1a}$ and $R^{1d}$ are each as defined herein. In certain embodiments, $R^6$ is —N$R^{1a}$C(S)N$R^{1b}R^{1c}$, wherein $R^{1a}$, $R^{1b}$, and $R^{1c}$ are each as defined herein. In certain embodiments, $R^6$ is —N$R^{1a}$S(O)$R^{1d}$, wherein $R^{1a}$ and $R^{1d}$ are each as defined herein. In certain embodiments, $R^6$ is —N$R^{1a}$S$(O)_2R^{1d}$, wherein $R^{1a}$ and $R^{1d}$ are each as defined herein. In certain embodiments, $R^6$ is —N$R^{1a}$S(O)N$R^{1b}R^{1c}$, wherein $R^{1a}$, $R^{1b}$, and $R^{1c}$ are each as defined herein. In certain embodiments, $R^6$ is —N$R^{1a}$S$(O)_2$N$R^{1b}R^{1c}$, wherein $R^{1a}$, $R^{1b}$, and $R^{1c}$ are each as defined herein. In certain embodiments, $R^6$ is —S(O)$R^{1a}$, wherein $R^{1a}$ is as defined herein. In certain embodiments, $R^6$ is —S$(O)_2R^{1a}$, wherein $R^{1a}$ is as defined herein. In certain embodiments, $R^6$ is —S(O)N$R^{1b}R^{1c}$, wherein $R^{1b}$ and $R^{1c}$ are each as defined herein. In certain embodiments, $R^6$ is —S$(O)_2$N$R^{1b}R^{1c}$, wherein $R^{1b}$ and $R^{1c}$ are each as defined herein.

In certain embodiments, $R^A$ is hydrogen. In certain embodiments, $R^A$ is deuterium. In certain embodiments, $R^A$ is cyano. In certain embodiments, $R^A$ is halo. In certain embodiments, $R^A$ is fluoro, chloro, or bromo. In certain embodiments, $R^A$ is nitro. In certain embodiments, $R^A$ is $C_{1-6}$ alkyl, optionally substituted with one or more substituents Q. In certain embodiments, $R^A$ is methyl, optionally substituted with one or more substituents Q. In certain embodiments, $R^A$ is $C_{2-6}$ alkenyl, optionally substituted with one or more substituents Q. In certain embodiments, $R^A$ is $C_{2-6}$ alkynyl, optionally substituted with one or more substituents Q. In certain embodiments, $R^A$ is $C_{3-10}$ cycloalkyl, optionally substituted with one or more substituents Q. In certain embodiments, $R^A$ is $C_{6-14}$ aryl, optionally substituted with one or more substituents Q. In certain embodiments, $R^A$ is $C_{7-15}$ aralkyl, optionally substituted with one or more substituents Q. In certain embodiments, $R^A$ is benzyl, optionally substituted with one or more substituents Q. In certain embodiments, $R^A$ is heteroaryl, optionally substituted with one or more substituents Q. In certain embodiments, $R^A$ is heterocyclyl, optionally substituted with one or more substituents Q.

In certain embodiments, $R^A$ is —C(O)$R^{1a}$, wherein $R^{1a}$ is as defined herein. In certain embodiments, $R^A$ is —C(O)O$R^{1a}$, wherein $R^{1a}$ is as defined herein. In certain embodiments, $R^A$ is —C(O)N$R^{1b}R^{1c}$, wherein $R^{1b}$ and $R^{1c}$ are each as defined herein. In certain embodiments, $R^A$ is —C(O)S$R^{1a}$, wherein $R^{1a}$ is as defined herein. In certain embodiments, $R^A$ is —C(N$R^{1a}$)N$R^{1b}R^{1c}$, wherein $R^{1a}$, $R^{1b}$, and $R^{1c}$ are each as defined herein. In certain embodiments, $R^A$ is —C(S)$R^{1a}$, wherein $R^{1a}$ is as defined herein. In certain embodiments, $R^A$ is —C(S)O$R^{1a}$, wherein $R^{1a}$ is as defined herein. In certain embodiments, $R^A$ is —C(S)N$R^{1b}R^{1c}$, wherein $R^{1b}$ and $R^{1c}$ are each as defined herein. In certain embodiments, $R^A$ is —O$R^{1a}$, wherein $R^{1a}$ is as defined herein. In certain embodiments, $R^A$ is —O$R^{1a}$, wherein $R^{1a}$ is $C_{1-6}$ alkyl, $C_{2-6}$ alkenyl, $C_{2-6}$ alkynyl, $C_{3-10}$ cycloalkyl, $C_{7-15}$ aralkyl, heteroaryl, or heterocyclyl, each optionally substituted with one or more substituents Q. In certain embodiments, $R^A$ is $C_{1-6}$ alkoxy, optionally substituted with one or more substituents Q. In certain embodiments, $R^A$ is —OC(O)$R^{1a}$, wherein $R^{1a}$ is as defined herein. In certain embodiments, $R^A$ is —OC(O)O$R^{1a}$, wherein $R^{1a}$ is as defined herein. In certain embodiments, $R^A$ is —OC(O)N$R^{1b}R^{1c}$, wherein $R^{1b}$ and $R^{1c}$ are each as defined herein. In certain embodiments, $R^A$ is —OC(O)S$R^{1a}$, wherein $R^{1a}$ is as defined herein. In certain embodiments, $R^A$ is —OC(═N$R^{1a}$)N$R^{1b}R^{1c}$, wherein $R^{1a}$, $R^{1b}$, and $R^{1c}$ are each as defined herein. In certain embodiments, $R^A$ is —OC(S)$R^{1a}$, wherein $R^{1a}$ is as defined herein. In certain embodiments, $R^A$ is —OC(S)O$R^{1a}$, wherein $R^{1a}$ is as defined herein. In certain embodiments, $R^A$ is —OC(S)N$R^{1b}R^{1c}$, wherein $R^{1b}$ and $R^{1c}$ are each as defined herein. In certain embodiments, $R^A$ is —OS(O)$R^{1a}$, wherein $R^{1a}$ is as defined herein. In certain embodiments, $R^A$ is —OS$(O)_2R^{1a}$, wherein $R^{1a}$ is as defined herein. In certain embodiments, $R^A$ is —OS(O)N$R^{1b}R^{1c}$, wherein $R^{1b}$ and $R^{1c}$ are each as defined herein. In certain embodiments, $R^A$ is —OS$(O)_2$N$R^{1b}R^{1c}$, wherein $R^{1b}$ and $R^{1c}$ are each as defined herein. In certain embodiments, $R^A$ is —N$R^{1b}R^{1c}$, wherein $R^{1b}$ and $R^{1c}$ are each as defined herein. In certain embodiments, $R^A$ is —N$R^{1a}$C(O)$R^{1d}$, wherein $R^{1a}$ and $R^{1d}$ are each as defined herein. In certain embodiments, $R^A$ is —N$R^{1a}$C(O)O$R^{1d}$, wherein $R^{1a}$ and $R^{1d}$ are each as defined herein. In certain embodiments, $R^A$ is —N$R^{1a}$C(O)N$R^{1b}R^{1c}$, wherein $R^{1a}$, $R^{1b}$, and $R^{1c}$ are each as defined herein. In certain embodiments, $R^A$ is —N$R^{1a}$C(O)S$R^{1d}$, wherein $R^{1a}$ and $R^{1d}$ are each as defined herein. In certain embodiments, $R^A$ is —N$R^{1a}$C(═N$R^{1d}$)N$R^{1b}R^{1c}$, wherein $R^{1a}$, $R^{1b}$, $R^{1c}$, and $R^{1d}$ are each as defined herein. In certain embodiments, $R^A$ is —N$R^{1a}$C(S)$R^{1d}$, wherein $R^{1a}$ and $R^{1d}$ are each as defined herein. In certain embodiments, $R^A$ is —N$R^{1a}$C(S)O$R^{1d}$, wherein $R^{1a}$ and $R^{1d}$ are each as defined herein. In certain embodiments, $R^A$ is —N$R^{1a}$C(S)N$R^{1b}R^{1c}$, wherein $R^{1a}$, $R^{1b}$, and $R^{1c}$ are each as defined herein. In certain embodiments, $R^A$ is —N$R^{1a}$S(O)$R^{1d}$, wherein $R^{1a}$ and $R^{1d}$ are each as defined herein. In certain embodiments, $R^A$ is —N$R^{1a}$S$(O)_2R^{1d}$, wherein $R^{1a}$ and $R^{1d}$ are each as defined herein. In certain embodiments, $R^A$ is —N$R^{1a}$S(O)N$R^{1b}R^{1c}$, wherein $R^{1a}$, $R^{1b}$, and $R^{1c}$ are each as defined herein. In certain embodiments, $R^A$ is —N$R^{1a}$S$(O)_2$N$R^{1b}R^{1c}$, wherein $R^{1a}$, $R^{1b}$, and $R^{1c}$ are each as defined herein. In certain embodiments, $R^A$ is —S(O)$R^{1a}$, wherein $R^{1a}$ is as defined herein. In certain embodiments, $R^A$ is —S$(O)_2R^{1a}$, wherein $R^{1a}$ is as defined herein. In certain embodiments, $R^A$ is —S(O)N$R^{1b}R^{1c}$, wherein $R^{1b}$ and $R^{1c}$ are each as defined herein. In certain embodiments, $R^A$ is —$S(O)_2NR^{1b}R^{1c}$, wherein $R^{1b}$ and $R^{1c}$ are each as defined herein.

In certain embodiments, $R^X$ is hydrogen. In certain embodiments, $R^X$ is deuterium. In certain embodiments, $R^X$ is cyano. In certain embodiments, $R^X$ is halo. In certain embodiments, $R^X$ is nitro. In certain embodiments, $R^X$ is $C_{1-6}$ alkyl, optionally substituted with one or more substituents Q. In certain embodiments, $R^X$ is methyl, optionally substituted with one or more substituents Q. In certain embodiments, $R^X$ is $C_{2-6}$ alkenyl, optionally substituted with one or more substituents Q. In certain embodiments, $R^X$ is $C_{2-6}$ alkynyl, optionally substituted with one or more substituents Q. In certain embodiments, $R^X$ is $C_{3-10}$ cycloalkyl, optionally substituted with one or more substituents Q. In certain embodiments, $R^X$ is $C_{6-14}$ aryl, optionally substituted with one or more substituents Q. In certain embodiments, $R^X$ is $C_{7-15}$ aralkyl, optionally substituted with one or more substituents Q. In certain embodiments, $R^X$ is heteroaryl, optionally substituted with one or more substituents Q. In certain embodiments, $R^X$ is heterocyclyl, optionally substituted with one or more substituents Q.

In certain embodiments, $R^X$ is —$C(O)R^{1a}$, wherein $R^{1a}$ is as defined herein. In certain embodiments, $R^X$ is —$C(O)OR^{1a}$, wherein $R^{1a}$ is as defined herein. In certain embodiments, $R^X$ is —$C(O)NR^{1b}R^{1c}$, wherein $R^{1b}$ and $R^{1c}$ are each as defined herein. In certain embodiments, $R^X$ is —$C(O)SR^{1a}$, wherein $R^{1a}$ is as defined herein. In certain embodiments, $R^X$ is —$C(NR^{1a})NR^{1b}R^{1c}$, wherein $R^{1a}$, $R^{1b}$, and $R^{1c}$ are each as defined herein. In certain embodiments, $R^X$ is —$C(S)R^{1a}$, wherein $R^{1a}$ is as defined herein. In certain embodiments, $R^X$ is —$C(S)OR^{1a}$, wherein $R^{1a}$ is as defined herein. In certain embodiments, $R^X$ is —$C(S)NR^{1b}R^{1c}$, wherein $R^{1b}$ and $R^{1c}$ are each as defined herein. In certain embodiments, $R^X$ is —$OR^{1a}$, wherein $R^{1a}$ is as defined herein. In certain embodiments, $R^X$ is —$OC(O)R^{1a}$, wherein $R^{1a}$ is as defined herein. In certain embodiments, $R^X$ is —$OC(O)OR^{1a}$, wherein $R^{1a}$ is as defined herein. In certain embodiments, $R^X$ is —$OC(O)NR^{1b}R^{1c}$, wherein $R^{1b}$ and $R^{1c}$ are each as defined herein. In certain embodiments, $R^X$ is —$OC(O)SR^{1a}$, wherein $R^{1a}$ is as defined herein. In certain embodiments, $R^X$ is —$OC(=NR^{1a})NR^{1b}R^{1c}$, wherein $R^{1a}$, $R^{1b}$, and $R^{1c}$ are each as defined herein. In certain embodiments, $R^X$ is —$OC(S)R^{1a}$, wherein $R^{1a}$ is as defined herein. In certain embodiments, $R^X$ is —$OC(S)OR^{1a}$, wherein $R^{1a}$ is as defined herein. In certain embodiments, $R^X$ is —$OC(S)NR^{1b}R^{1c}$, wherein $R^{1b}$ and $R^{1c}$ are each as defined herein. In certain embodiments, $R^X$ is —$OS(O)R^{1a}$, wherein $R^{1a}$ is as defined herein. In certain embodiments, $R^X$ is —$OS(O)_2R^{1a}$, wherein $R^{1a}$ is as defined herein. In certain embodiments, $R^X$ is —$OS(O)NR^{1b}R^{1c}$, wherein $R^{1b}$ and $R^{1c}$ are each as defined herein. In certain embodiments, $R^X$ is —$OS(O)_2NR^{1b}R^{1c}$, wherein $R^{1b}$ and $R^{1c}$ are each as defined herein. In certain embodiments, $R^X$ is —$NR^{1b}R^{1c}$, wherein $R^{1b}$ and $R^{1c}$ are each as defined herein. In certain embodiments, $R^X$ is —$NR^{1a}C(O)R^{1d}$, wherein $R^{1a}$ and $R^{1d}$ are each as defined herein. In certain embodiments, $R^X$ is —$NR^{1a}C(O)OR^{1d}$, wherein $R^{1a}$ and $R^{1d}$ are each as defined herein. In certain embodiments, $R^X$ is —$NR^{1a}C(O)NR^{1b}R^{1c}$, wherein $R^{1a}$, $R^{1b}$, and $R^{1c}$ are each as defined herein. In certain embodiments, $R^X$ is —$NR^{1a}C(O)SR^{1d}$, wherein $R^{1a}$ and $R^{1d}$ are each as defined herein. In certain embodiments, $R^X$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^X$ is —$NR^{1a}C(S)R^{1d}$, wherein $R^{1a}$ and $R^{1d}$ are each as defined herein. In certain embodiments, $R^X$ is —$NR^{1a}C(S)OR^{1d}$, wherein $R^{1a}$ and $R^{1d}$ are each as defined herein. In certain embodiments, $R^X$ is —$NR^{1a}C(S)NR^{1b}R^{1c}$, wherein $R^{1a}$, $R^{1b}$, and $R^{1c}$ are each as defined herein. In certain embodiments, $R^X$ is —$NR^{1a}S(O)R^{1d}$, wherein $R^{1a}$ and $R^{1d}$ are each as defined herein. In certain embodiments, $R^X$ is —$NR^{1a}S(O)_2R^{1d}$, wherein $R^{1a}$ and $R^{1d}$ are each as defined herein. In certain embodiments, $R^X$ is —$NR^{1a}S(O)NR^{1b}R^{1c}$, wherein $R^{1a}$, $R^{1b}$, and $R^{1c}$ are each as defined herein. In certain embodiments, $R^X$ is —$NR^{1a}S(O)_2NR^{1b}R^{1c}$, wherein $R^{1a}$, $R^{1b}$, and $R^{1c}$ are each as defined herein. In certain embodiments, $R^X$ is —$S(O)R^{1a}$, wherein $R^{1a}$ is as defined herein. In certain embodiments, $R^X$ is —$S(O)_2R^{1a}$, wherein $R^{1a}$ is as defined herein. In certain embodiments, $R^X$ is —$S(O)NR^{1b}R^{1c}$, wherein $R^{1b}$ and $R^{1c}$ are each as defined herein. In certain embodiments, $R^X$ is —$S(O)_2NR^{1b}R^{1c}$, wherein $R^{1b}$ and $R^{1c}$ are each as defined herein.

In certain embodiments, $R^Y$ is hydrogen. In certain embodiments, $R^Y$ is deuterium. In certain embodiments, $R^Y$ is cyano. In certain embodiments, $R^Y$ is halo. In certain embodiments, $R^Y$ is nitro. In certain embodiments, $R^Y$ is $C_{1-6}$ alkyl, optionally substituted with one or more substituents Q. In certain embodiments, $R^Y$ is methyl, optionally substituted with one or more substituents Q. In certain embodiments, $R^Y$ is $C_{2-6}$ alkenyl, optionally substituted with one or more substituents Q. In certain embodiments, $R^Y$ is $C_{2-6}$ alkynyl, optionally substituted with one or more substituents Q. In certain embodiments, $R^Y$ is $C_{3-10}$ cycloalkyl, optionally substituted with one or more substituents Q. In certain embodiments, $R^Y$ is $C_{6-14}$ aryl, optionally substituted with one or more substituents Q. In certain embodiments, $R^Y$ is $C_{7-15}$ aralkyl, optionally substituted with one or more substituents Q. In certain embodiments, $R^Y$ is heteroaryl, optionally substituted with one or more substituents Q. In certain embodiments, $R^Y$ is heterocyclyl, optionally substituted with one or more substituents Q.

In certain embodiments, $R^Y$ is —$C(O)R^{1a}$, wherein $R^{1a}$ is as defined herein. In certain embodiments, $R^Y$ is —$C(O)OR^{1a}$, wherein $R^{1a}$ is as defined herein. In certain embodiments, $R^Y$ is —$C(O)NR^{1b}R^{1c}$, wherein $R^{1b}$ and $R^{1c}$ are each as defined herein. In certain embodiments, $R^Y$ is —$C(O)SR^{1a}$, wherein $R^{1a}$ is as defined herein. In certain embodiments, $R^Y$ is —$C(NR^{1a})NR^{1b}R^{1c}$, wherein $R^{1a}$, $R^{1b}$, and $R^{1c}$ are each as defined herein. In certain embodiments, $R^Y$ is —$C(S)R^{1a}$, wherein $R^{1a}$ is as defined herein. In certain embodiments, $R^Y$ is —$C(S)OR^{1a}$, wherein $R^{1a}$ is as defined herein. In certain embodiments, $R^Y$ is —$C(S)NR^{1b}R^{1c}$, wherein $R^{1b}$ and $R^{1c}$ are each as defined herein. In certain embodiments, $R^Y$ is —$OR^{1a}$, wherein $R^{1a}$ is as defined herein. In certain embodiments, $R^Y$ is —$OC(O)R^{1a}$, wherein $R^{1a}$ is as defined herein. In certain embodiments, $R^Y$ is —$OC(O)OR^{1a}$, wherein $R^{1a}$ is as defined herein. In certain embodiments, $R^Y$ is —$OC(O)NR^{1b}R^{1c}$, wherein $R^{1b}$ and $R^{1c}$ are each as defined herein. In certain embodiments, $R^Y$ is —$OC(O)SR^{1a}$, wherein $R^{1a}$ is as defined herein. In certain embodiments, $R^Y$ is —$OC(=NR^{1a})NR^{1b}R^{1c}$, wherein $R^{1a}$, $R^{1b}$, and $R^{1c}$ are each as defined herein. In certain embodiments, $R^Y$ is —$OC(S)R^{1a}$, wherein $R^{1a}$ is as defined herein. In certain embodiments, $R^Y$ is —$OC(S)OR^{1a}$, wherein $R^{1a}$ is as defined herein. In certain embodiments, $R^Y$ is —$OC(S)NR^{1b}R^{1c}$, wherein $R^{1b}$ and $R^{1c}$ are each as defined herein. In certain embodiments, R is —$OS(O)R^{1a}$, wherein $R^{1a}$ is as defined herein. In certain embodiments, $R^Y$ is —$OS(O)_2R^{1a}$, wherein $R^{1a}$ is as defined herein. In certain embodiments, $R^Y$ is —$OS(O)NR^{1b}R^{1c}$, wherein $R^{1b}$ and $R^{1c}$ are each as defined herein. In certain embodiments, $R^Y$ is —$OS(O)_2NR^{1b}R^{1c}$, wherein $R^{1b}$ and $R^{1c}$ are each as defined herein. In certain embodiments, $R^Y$ is —$NR^{1b}R^{1c}$, wherein $R^{1b}$ and $R^{1c}$ are each as defined herein. In certain embodiments, $R^Y$ is —$NR^{1a}C(O)R^{1d}$, wherein $R^{1a}$ and $R^{1d}$ are each as defined herein. In certain embodiments, $R^Y$ is —$NR^{1a}C(O)OR^{1d}$, wherein $R^{1a}$ and $R^{1d}$ are each as defined herein. In certain embodiments, $R^Y$ is —$NR^{1a}C(O)NR^{1b}R^{1c}$, wherein $R^{1a}$, $R^{1b}$, and $R^{1c}$ are each as defined herein. In certain embodiments, $R^Y$ is —$NR^{1a}C(O)SR^{1d}$, wherein $R^{1a}$ and $R^{1d}$ are each as defined herein. In certain embodiments, $R^Y$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^Y$ is —$NR^{1a}C(S)R^{1d}$, wherein $R^{1a}$ and $R^{1d}$ are each as defined herein. In certain embodiments, $R^Y$ is —$NR^{1a}C(S)OR^{1d}$, wherein $R^{1a}$ and $R^{1d}$ are each as defined herein. In certain embodiments, $R^Y$ is —$NR^{1a}C(S)NR^{1b}R^{1c}$, wherein $R^{1a}$, $R^{1b}$, and $R^{1c}$ are each as defined herein. In certain embodiments, $R^Y$ is —$NR^{1a}S(O)R^{1d}$, wherein $R^{1a}$ and $R^{1d}$ are each as defined herein. In certain embodiments, $R^Y$ is —$NR^{1a}S(O)_2R^{1d}$, wherein $R^{1a}$ and $R^{1d}$ are each as defined herein. In certain embodiments, $R^Y$ is —$NR^{1a}S(O)NR^{1b}R^{1c}$, wherein $R^{1a}$, $R^{1b}$, and $R^{1c}$ are each as defined herein. In certain embodiments, $R^Y$ is —$NR^{1a}S(O)_2NR^{1b}R^{1c}$, wherein $R^{1a}$, $R^{1b}$, and $R^{1c}$ are each as defined herein. In certain embodiments, $R^Y$ is —$S(O)R^{1a}$, wherein $R^{1a}$ is as defined herein. In certain embodiments, $R^Y$ is —$S(O)_2R^{1a}$, wherein $R^{1a}$ is as defined herein. In certain embodiments, $R^Y$ is —$S(O)NR^{1b}R^{1c}$, wherein $R^{1b}$ and $R^{1c}$ are each as defined herein. In certain embodiments, $R^Y$ is —$S(O)_2NR^{1b}R^{1c}$, wherein $R^{1b}$ and $R^{1c}$ are each as defined herein.

In certain embodiments, m is 0. In certain embodiments, m is 1. In certain embodiments, m is 2. In certain embodiments, m is 3. In certain embodiments, m is 4.

In certain embodiments, E is a bond. In certain embodiments, E is —O—. In certain embodiments, E is —S—. In certain embodiments, E is —N═. In certain embodiments, E is —$N(R^A)$—, wherein $R^A$ is as defined herein. In certain embodiments, E is —N(H)—. In certain embodiments, E is —$C(R^A)$—, wherein $R^A$ is as defined herein. In certain embodiments, E is —C(H)—.

In certain embodiments, G is —O—. In certain embodiments, G is —S—. In certain embodiments, G is —N═. In certain embodiments, G is —$N(R^A)$—, wherein $R^A$ is as defined herein. In certain embodiments, G is —N(H)—. In certain embodiments, G is —$C(R^A)$—, wherein $R^A$ is as defined herein. In certain embodiments, G is —C(H)—.

In certain embodiments, J is —O—. In certain embodiments, J is —S—. In certain embodiments, J is —N═. In certain embodiments, J is —$N(R^A)$—, wherein $R^A$ is as defined herein. In certain embodiments, J is —N(H)—. In certain embodiments, J is —$C(R^A)$—, wherein $R^A$ is as defined herein. In certain embodiments, J is —C(H)—.

In certain embodiments, L is —O—. In certain embodiments, L is —S—. In certain embodiments, L is —N═. In certain embodiments, L is —$N(R^A)$—, wherein $R^A$ is as defined herein. In certain embodiments, L is —N(H)—. In certain embodiments, L is —$C(R^A)$—, wherein $R^A$ is as defined herein. In certain embodiments, L is —C(H)—.

In certain embodiments, M is —O—. In certain embodiments, M is —S—. In certain embodiments, M is —N═. In certain embodiments, M is —$N(R^A)$—, wherein $R^A$ is as defined herein. In certain embodiments, M is —N(H)—. In certain embodiments, M is —$C(R^A)$—, wherein $R^A$ is as defined herein. In certain embodiments, M is —C(H)—.

In certain embodiments, Q is a bond. In certain embodiments, Q is —O—. In certain embodiments, Q is —S—. In certain embodiments, Q is —N═. In certain embodiments, Q is —$N(R^A)$—, wherein $R^A$ is as defined herein. In certain embodiments, Q is —N(H)—. In certain embodiments, Q is —$C(R^A)$—, wherein $R^A$ is as defined herein. In certain embodiments, Q is —C(H)—.

In certain embodiments, R is —O—. In certain embodiments, R is —S—. In certain embodiments, R is —N═. In certain embodiments, R is —$N(R^A)$—, wherein $R^A$ is as defined herein. In certain embodiments, R is —N(H)—. In certain embodiments, R is —$C(R^A)$—, wherein $R^A$ is as defined herein. In certain embodiments, R is —C(H)—.

In certain embodiments, U is —O—. In certain embodiments, U is —S—. In certain embodiments, U is —N═. In certain embodiments, U is —$N(R^A)$—, wherein $R^A$ is as defined herein. In certain embodiments, U is —N(H)—. In certain embodiments, U is —$C(R^A)$—, wherein $R^A$ is as defined herein. In certain embodiments, U is —C(H)—.

In certain embodiments, V is —O—. In certain embodiments, V is —S—. In certain embodiments, V is —N═. In certain embodiments, V is —$N(R^A)$—, wherein $R^A$ is as defined herein. In certain embodiments, V is —N(H)—. In certain embodiments, V is —$C(R^A)$—, wherein $R^A$ is as defined herein. In certain embodiments, V is —C(H)—.

In certain embodiments, W is —O—. In certain embodiments, W is —S—. In certain embodiments, W is —N═. In certain embodiments, W is —$N(R^A)$—, wherein $R^A$ is as defined herein. In certain embodiments, W is —N(H)—. In certain embodiments, W is —$C(R^A)$—, wherein $R^A$ is as defined herein. In certain embodiments, W is —C(H)—.

In certain embodiments, X is —$SO_2$—. In certain embodiments, X is —$CR^XR^X$—, wherein $R^X$ and $R^Y$ are each as defined herein. In certain embodiments, X is —$CH_2$—.

In certain embodiments, Y is —$SO_2$—. In certain embodiments, Y is —$CR^XR^X$—, wherein $R^X$ and $R^Y$ are each as defined herein. In certain embodiments, Y is —$CH_2$—. In certain embodiments, Y is —$N(R^A)$—, wherein $R^A$ is as defined herein. In certain embodiments, Y is —NH—.

In one embodiment, provided herein is:

3-((2-methyl-5-(trifluoromethyl)benzyl)sulfonyl)benzoic acid (A1);

3-((3,5-dimethoxybenzyl)sulfonyl)benzoic acid (A2);

3-(N-(4-fluoro-3,5-bis(2,2,2-trifluoroethoxy)phenyl)sulfamoyl)benzoic acid (A3);

3-(N-(2,6-difluoro-3,5-bis(2,2,2-trifluoroethoxy)phenyl)sulfamoyl)benzoic acid (A4);

3-(N-(2,4,6-trifluoro-3,5-bis(2,2,2-trifluoroethoxy)phenyl)sulfamoyl)benzoic acid (A5);

3-(N-(3,5-bis(difluoromethoxy)phenyl)sulfamoyl)benzoic acid (A6);

3-(N-(3,5-bis(difluoromethoxy)-4-fluorophenyl)sulfamoyl)benzoic acid (A7);

3-(N-(3,5-bis(difluoromethoxy)-2,6-difluorophenyl)sulfamoyl)benzoic acid (A8);

3-(N-(3,5-bis(difluoromethoxy)-2,4,6-trifluorophenyl)sulfamoyl)benzoic acid (A9);

3-(N-(3,5-bis(2,2-difluoroethoxy)phenyl)sulfamoyl)benzoic acid (A10);

3-(N-(3,5-bis(2,2-difluoroethoxy)-4-fluorophenyl)sulfamoyl)benzoic acid (A11);

3-(N-(3,5-bis(2,2-difluoroethoxy)-2,6-difluorophenyl)sulfamoyl)benzoic acid (A12);

3-(N-(3,5-bis(2,2-difluoroethoxy)-2,4,6-trifluorophenyl)sulfamoyl)benzoic acid (A13);

3-(N-(2,6-difluoro-3,5-dimethoxyphenyl)sulfamoyl)benzoic acid (A14);

3-(N-(2,4,6-trifluoro-3,5-dimethoxyphenyl)sulfamoyl)benzoic acid (A15);

3-(N-(4-fluoro-3,5-dimethoxyphenyl)sulfamoyl)benzoic acid (A16);

3-(N-(2,4,6-trifluoro-3-methoxy-5-(trifluoromethoxy)phenyl)sulfamoyl)benzoic acid (A17);

3-(N-(3-ethoxy-2,4,6-trifluoro-5-methoxyphenyl)sulfamoyl)benzoic acid (A18);

3-(N-(2,6-difluoro-3,5-dimethoxy-4-(methoxycarbonyl) phenyl)sulfamoyl)benzoic acid (A19);

3-(N-(4-(tert-butoxycarbonyl)-2,6-difluoro-3,5-dimethoxyphenyl)sulfamoyl)benzoic acid (A20);

3-(N-(4-(dimethylcarbamoyl)-2,6-difluoro-3,5-dimethoxyphenyl)sulfamoyl)benzoic acid (A21); or 3-(N-(2,6-difluoro-3,5-dimethoxy-4-(piperidine-1-carbonyl)phenyl)sulfamoyl)benzoic acid (A22);

or a tautomer, a mixture of two or more tautomers, or an isotopic variant thereof, or a pharmaceutically acceptable salt, solvate, hydrate, or prodrug thereof.

In certain embodiments, a compound provided herein is deuterium-enriched. In certain embodiments, a compound provided herein is carbon-13 enriched. In certain embodiments, a compound provided herein is carbon-14 enriched. In certain embodiments, a compound provided herein contains one or more less prevalent isotopes for other elements, including, but not limited to, $^{15}N$ for nitrogen; $^{17}O$ or $^{18}O$ for oxygen, and $^{33}S$, $^{34}S$, or $^{36}S$ for sulfur.

In certain embodiments, a compound provided herein has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6410 for deuterium and 90 for carbon-13.

In certain embodiments, a compound provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, a compound provided herein has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of a compound provided herein, as specified as isotopically enriched, has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as isotopically enriched, have isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of a compound provided herein is no less than the natural abundance of the isotope specified.

In certain embodiments, at least one of the atoms of a compound provided herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as deuterium-enriched, have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of a compound provided herein, as specified as $^{13}C$-enriched, has carbon-13 enrichment of no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as $^{13}C$-enriched, have carbon-13 enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, a compound provided herein is isolated or purified. In certain embodiments, a compound provided herein has a purity of at least about 50%, at least about 70%, at least about 80%, at least about 90%, at least about 95%, at least about 98%, at least about 99%, or at least about 99.5% by weight.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

A compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; Wiley-VCH and VHCA, Zurich, 2011. In certain embodiments, a pharmaceutically acceptable salt of a compound provided herein is a hydrate.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid. In certain embodiments, the compounds provided herein are hydrochloride salts.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of a compound, for example, of Formula A and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In certain embodiments, the compounds provided herein attenuate (e.g., partially attenuates) an amyloid β activity. In one embodiment, the compounds provided herein attenuate an amyloid β activity by at least about 10%. In another embodiment, the compounds provided herein attenuate an amyloid β activity by at least about 20%. In yet another embodiment, the compounds provided herein attenuate an amyloid β activity by at least about 30%. In yet another embodiment, the compounds provided herein attenuate an amyloid β activity at least about 40%. In yet another embodiment, the compounds provided herein attenuate an amyloid β activity by at least about 50%. In yet another embodiment, the compounds provided herein attenuate an amyloid β activity by at least about 60%. In yet another embodiment, the compounds provided herein attenuate an amyloid β activity by at least about 70%. In yet another embodiment, the compounds provided herein attenuate an amyloid β activity by at least about 80%. In yet another embodiment, the compounds provided herein attenuate an amyloid β activity by at least about 90%. In yet another embodiment, the compounds provided herein attenuate an amyloid β activity by at least about 95%. In yet another embodiment, the compounds provided herein attenuate (e.g., partially attenuate) an amyloid β activity by at least about 15% to about 65%. In still another embodiment, the compounds provided herein attenuate (e.g., partially attenuate) an amyloid β activity by at least about 30% to about 65%.

In certain embodiments, the attenuation of an amyloid β activity is assessed by methods known to one of skill in the art. In certain embodiments, the attenuation of an amyloid β activity is relative to the amyloid β activity in the presence of stimulation without any of the compounds described herein.

A non-limiting example of an amyloid β activity is amyloid β-induced or -mediated signaling. Thus, in certain embodiments, the compounds provided herein attenuate (e.g., partially attenuates) amyloid β-induced signaling. Another non-limiting example of amyloid β-induced signaling is interacting with (including blocking) receptors, including, but not limited to, glucose transporters, NMDAR, AMPAR, and acetylcholine receptors, activation of inflammatory signaling pathways, and the activation of one or more kinases, including, but not limited to, GSK-3, CDK5, PKC, PKA, and Erk1/2. Activities can include blocking ion channels, disruption of calcium homeostasis, mitochondrial oxidative stress, impaired energy metabolism, abnormal glucose regulation, and/or neuronal cell death.

In certain embodiments, the compounds described herein attenuate (e.g., partially attenuates) a tau protein activity. In one embodiment, the compounds provided herein attenuate a tau protein activity by at least about 10%. In another embodiment, the compounds provided herein attenuate a tau protein activity by at least about 20%. In yet another embodiment, the compounds provided herein attenuate a tau protein activity by at least about 30%. In yet another embodiment, the compounds provided herein attenuate a tau protein activity at least about 40%. In yet another embodiment, the compounds provided herein attenuate a tau protein activity by at least about 50%. In yet another embodiment, the compounds provided herein attenuate a tau protein activity by at least about 60%. In yet another embodiment, the compounds provided herein attenuate a tau protein activity by at least about 70%. In yet another embodiment, the compounds provided herein attenuate a tau protein activity by at least about 80%. In yet another embodiment, the compounds provided herein attenuate a tau protein activity by at least about 90%. In yet another embodiment, the compounds provided herein attenuate a tau protein activity by at least about 95%. In yet another embodiment, the compounds provided herein attenuate (e.g., partially attenuate) a tau protein by at least about 15% to about 65%. In still another embodiment, the compounds provided herein attenuate (e.g., partially attenuate) a tau protein by at least about 30% to about 65%.

In certain embodiments, the attenuation of a tau protein activity is assessed by methods known to one of skill in the art. In certain embodiments, the attenuation of a tau protein activity is relative to the tau protein activity without any of the compounds described herein.

A non-limiting example of a tau protein activity is a tau protein-induced or -mediated signaling. Thus, in certain embodiments, the compound provided herein attenuates (e.g., partially attenuates) tau protein-induced signaling. Non-limiting examples of a tau protein activity include interacting with tubulin to stabilize microtubules, formation of helical and/or straight filaments, activation of inflammatory signaling pathways and impaired insulin signaling in the brain.

Method of Synthesis

The compounds provided herein can be prepared, isolated, or obtained by any method known to one of ordinary skill in the art. In certain embodiments, a compound of Formula V is synthesized as shown in Scheme I, wherein $L^R$ is a leaving group (e.g., chloro, bromo, or iodo); and $R^1$, $R^2$, $R^3$, $R^4$, $R^5$, $R^6$, Y, and m are each as defined herein. Compound 1 is coupled with compound 2 in the presence of a base (e.g., potassium hydroxide or sodium carbonate) to form compound 3, which is then oxidized with an oxidizing agent (e.g., dihydrogen peroxide) to form a compound of Formula V.

Pharmaceutical Compositions

In one embodiment, provided herein is a pharmaceutical composition comprising a compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and a pharmaceutically acceptable excipient.

Scheme I

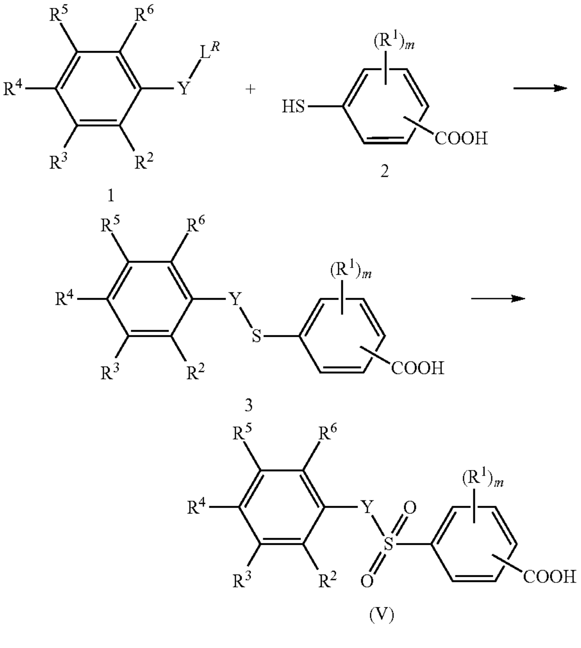

In one embodiment, the pharmaceutical composition provided herein is formulated in a dosage form for oral administration, which comprises a compound provided herein, e.g., a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

In another embodiment, a pharmaceutical composition provided herein is formulated in a dosage form for parenteral administration, which comprises a compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and a pharmaceutically acceptable excipient. In one embodiment, a pharmaceutical composition provided herein is formulated in a dosage form for intravenous administration. In another embodiment, a pharmaceutical composition provided herein is formulated in a dosage form for intramuscular administration. In yet another embodiment, a pharmaceutical composition provided herein is formulated in a dosage form for subcutaneous administration.

In yet another embodiment, a pharmaceutical composition provided herein is formulated in a dosage form for topical administration, which comprise a compound provided herein, e.g., a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

The compound provided herein may be administered alone, or in combination with one or more other compounds provided herein. The pharmaceutical compositions that comprise a compound provided herein, e.g., a compound of Formula A, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology,* 2nd Edition, Rathbone et al., Eds., Marcel Dekker, Inc.: New York, N.Y., 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; algins; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers;

hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method for treating, ameliorating, or preventing a disorder, disease, or condition in a subject, comprising administering to the subject a therapeutically effective amount of a compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In another embodiment, provided herein is a method for treating, ameliorating, or preventing one or more symptoms of a disorder, disease, or condition in a subject, comprising administering to the subject a pharmaceutical composition provided herein, e.g., a pharmaceutical composition comprising a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

In certain embodiments, the disorder, disease, or condition is a neurological disease. In certain embodiments, the disorder, disease, or condition is a neurodegenerative disease. In certain embodiments, the disorder, disease, or condition is an ocular disorder. In certain embodiments, the disorder, disease, or condition is Downs syndrome.

In certain embodiments, the disorder, disease, or condition is Parkinson's disease (PD), Alzheimer's disease (AD), traumatic brain injury (TBI), amyotrophic lateral sclerosis (ALS), multiple sclerosis (MS), or dementia. In certain embodiments, the disorder, disease, or condition is Parkinson's disease. In certain embodiments, the disorder, disease, or condition is traumatic brain injury. In certain embodiments, the disorder, disease, or condition is amyotrophic lateral sclerosis. In certain embodiments, the disorder, disease, or condition is multiple sclerosis. In certain embodiments, the disorder, disease, or condition is dementia. In certain embodiments, the disorder, disease, or condition is frontotemporal dementia.

In certain embodiments, the disorder, disease, or condition is a disorder, disease, or condition mediated by a tau protein. In certain embodiments, the disorder, disease, or condition mediated by a tau protein is tauopathy. In certain embodiments, the disorder, disease, or condition mediated by a tau protein is Alzheimer's disease.

In certain embodiments, the disorder, disease, or condition is Alzheimer's disease. In certain embodiments, the Alzheimer's disease is Stage 1 AD (no impairment). In certain embodiments, the Alzheimer's disease is Stage 2 AD (very mild decline). In certain embodiments, the Alzheimer's disease is Stage 3 AD (mild decline). In certain embodiments, the Alzheimer's disease is Stage 4 AD (moderate decline). In certain embodiments, the Alzheimer's disease is Stage 5 AD (moderately severe decline). In certain embodiments, the Alzheimer's disease is Stage 6 AD (severe decline). In certain embodiments, the Alzheimer's disease is Stage 7 AD (very severe decline).

The methods provided herein encompass treating a subject regardless of patient's age, although some diseases or disorders are more common in certain age groups.

Depending on the disease to be treated and the subject's condition, a compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Also provided herein is administration of the compounds or pharmaceutical compositions provided herein in a depot formulation, in which the active ingredient is released over a predefined time period. A compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can be formulated, alone or together, in suitable dosage unit with pharmaceutically acceptable excipients, carriers, adjuvants and vehicles, appropriate for each route of administration.

In one embodiment, a compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered orally. In another embodiment, a compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered parenterally. In yet another embodiment, a compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered intravenously. In yet another embodiment, a compound provided herein, e.g., a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered intramuscularly. In yet another embodiment, a compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered subcutaneously. In still another embodiment, a compound provided herein, e.g., a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered topically.

A compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can be delivered as a single dose such as, e.g., a single bolus injection, or oral tablets or pills; or over time such as, e.g., continuous infusion over time or divided bolus doses over time. The compound provided herein can be administered repetitively if necessary, for example, until the subject experiences stable disease or regression, or until the subject experiences disease progression or unacceptable toxicity. Stable disease or lack thereof is determined by methods known in the art such as evaluation of subject's symptoms and physical examination.

A compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound provided herein, e.g., a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administration for one to six days per week, administration in cycles (e.g., daily administration for two to eight consecutive weeks, then a rest period with no administration for up to one week), or administration on alternate days.

In certain embodiments, a compound provided herein, e.g., a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

In certain embodiments, the therapeutically effective amount is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

It will be understood, however, that the specific dose level and frequency of dosage for any particular subject can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In certain embodiments, the subject is a mammal. In certain embodiments, the subject is a human.

A compound provided herein, e.g., a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can also be combined or used in combination with other therapeutic agents useful in the treatment and/or prevention of a disorder, disease, or condition described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of a compound provided herein, e.g., a compound of Formula A, or an enantiomer, a mixture of enantiomers, or a mixture of diastereomers thereof, or a pharmaceutically acceptable salt, solvate, or prodrug thereof, is independent of the route of administration of a second therapy. In one embodiment, a compound provided herein, e.g., a compound of Formula A, or an enantiomer, a mixture of enantiomers, or a mixture of diastereomers thereof; or a pharmaceutically acceptable salt, solvate, or prodrug thereof, is administered orally. In another embodiment, a compound provided herein, e.g., a compound of Formula A, or an enantiomer, a mixture of enantiomers, or a mixture of diastereomers thereof, or a pharmaceutically acceptable salt, solvate, or prodrug thereof, is administered intravenously. Thus, in accordance with these embodiments, a compound provided herein, e.g., a compound of Formula A, or an enantiomer, a mixture of enantiomers, or a mixture of diastereomers thereof, or a pharmaceutically acceptable salt, solvate, or prodrug thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a compound provided herein, e.g., a compound of Formula A, or an enantiomer, a mixture of enantiomers, or a mixture of diastereomers thereof, or a pharmaceutically acceptable salt, solvate, or prodrug thereof, and a second therapy are administered by the same mode of administration, orally or by IV. In another embodiment, a compound provided herein, e.g., a compound of Formula A, including an enantiomer, a mixture of enantiomers, or a mixture of diastereomers thereof, or a pharmaceutically acceptable salt, solvate, or prodrug thereof, is administered by one mode of administration, e.g., by IV, whereas the second agent is administered by another mode of administration, e.g., orally.

In certain embodiments, each method provided herein may independently, further comprise the step of administering a second therapeutic agent.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, e.g., a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of an active ingredient.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

In one embodiment, provided herein is a method for inhibiting the production of amyloid β in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the method provided herein is for inhibiting the total production of amyloid β in a subject.

In another embodiment, provided herein is a method for attenuating the amyloid β level in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the method provided herein is for attenuating the total amyloid β level in a subject.

In yet another embodiment, provided herein is a method for attenuating amyloid β-induced signaling pathway in a subject or a cell, comprising administering to the subject or a cella therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the method provided herein is for attenuating the total amyloid β level in a subject.

In yet another embodiment, provided herein is a method of inhibiting the production of amyloid β in a cell, comprising contacting the cell with an effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the method provided herein is for inhibiting the total production of amyloid β in a cell.

In one embodiment, the amyloid β is amyloid β36, amyloid β37, amyloid β38, amyloid β39, amyloid β40, amyloid β41, amyloid β42, amyloid β43, amyloid β44, amyloid β 45, amyloid β46, amyloid β47, amyloid β48, amyloid β49, amyloid β50, amyloid β51, or amyloid β52, or a combination thereof. In another embodiment, the amyloid β is amyloid β40. In yet another embodiment, the amyloid β is amyloid β42.

In one embodiment, provided herein is a method of inhibiting the production of a tau protein in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the method provided herein is for inhibiting the total production of tau proteins, including phosphorylated tau proteins, in a subject.

In another embodiment, provided herein is a method of attenuating the tau protein level in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the method provided herein is for attenuating the total tau protein level in a subject.

In yet another embodiment, provided herein is a method of inhibiting the production of a tau protein in a cell, comprising contacting the cell with an effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the method provided herein is for inhibiting the total production of tau proteins, including phosphorylated tau proteins, in a cell.

In one embodiment, the tau protein is a phosphorylated tau protein. In another embodiment, the tau protein is a hyperphosphorylated tau protein. In yet another embodiment, the tau protein is a human tau protein. In still another embodiment, the tau protein is human isoform 0N3R, 0N4R, 1N3R, 1N4R, 2N3R, or 2N4R.

In one embodiment, provided herein is a method of inhibiting the production of a phosphorylated tau protein in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In another embodiment, provided herein is a method of attenuating the phosphorylated tau protein level in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a method of inhibiting the production of a phosphorylated tau protein in a cell, comprising contacting the cell with an effective amount of a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In one embodiment, provided herein is a method of inhibiting the production of a hyperphosphorylated tau protein in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is a method of attenuating the hyperphosphorylated tau protein level in a subject, comprising administering to the subject a therapeutically effective amount of a compound of Formula A, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a method of inhibiting the production of a hyperphosphorylated tau protein in a cell, comprising contacting the cell with an effective amount of a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In still another embodiment, provided herein is a method of attenuating the tau protein-induced signaling in a subject or a cell, comprising contacting the subject or cell with an effective amount of a compound of Formula A, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry.

Example 1

Preparation of 3-((2-methyl-5-(trifluoromethyl)benzyl)sulfonyl)benzoic acid A1

A1

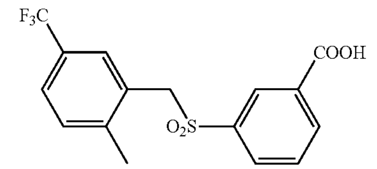

Compound A1 was synthesized as shown in Scheme 1 below.

Scheme 1

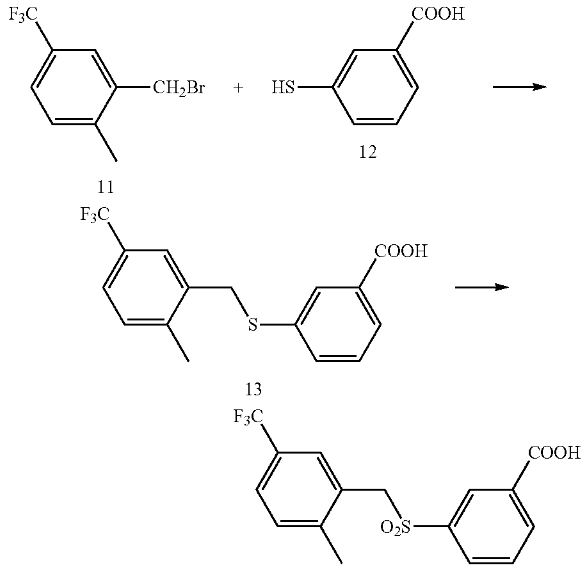

11 12 13 A1

Compound 13. A mixture of 2-(bromomethyl)-1-methyl-4-(trifluoromethyl)-benzene 11 (2.97 mmol), 3-mercaptobenzoic acid 12 (2.7 mmol), and potassium hydroxide (5.94 mmol) in ethanol (8 mL) and water (1 mL) was stirred under a nitrogen until all materials dissolved. After refluxed and stirred vigorously for 18 h, the reaction mixture was diluted with $H_2O$ (5 mL) and acidified with 1M HCl to pH~1. The resulting solids were collected, washed with water, and dried in vacuo to yield compound 13, which was used directly without further purification.

Compound A1. To a solution of compound 13 (0.306 mmol) in acetic acid (3.5 mL) at 70° C. was added $H_2O_2$ (30%, 0.09 mL, 0.918 mmol) dropwise. After stirred at 70° C. for 1.5 h, a second batch of $H_2O_2$ (30%, 0.05 mL) was added. After stirred for additional 1.5 h, the reaction was complete as determined by HPLC. The reaction mixture was then cooled to room temperature, added to ice-water (8.5 mL), and stirred for 5 min. The resulting solids were collected and dried at 35° C. to yield compound A1, a $^1H$ NMR of which is shown in FIG. 1.

Example 2

Preparation of 3-((3,5-dimethoxybenzyl)sulfonyl)benzoic acid A2

A2

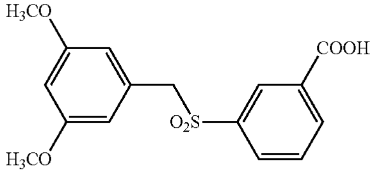

Compound A2 was synthesized as shown in Scheme 2 below.

Scheme 2

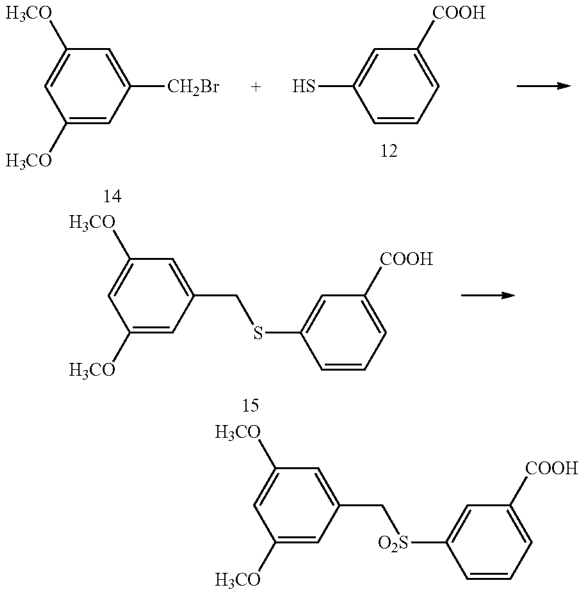

12 14 15 A2

Compound 15. A mixture of 1-(bromomethyl)-3,5-dimethoxybenzene 14 (21.6 mmol), 3-mercaptobenzoic acid 12 (19.7 mmol), and KOH (43.3 mmol) in EtOH (25 mL) and $H_2O$ (5 mL) was stirred and refluxed under nitrogen for 1 h. The reaction mixture was then cooled to room temperature and treated with water (2 mL) and 1M HCl (~20 mL) to bring pH 1. The resulting solids were collected and washed with ethanol/water (1:1). The filtrate was filtered again to yield a second batch of solids, which were washed with water. The two batches of solids were combined, dissolved in 1M NaOH (100 mL), and extracted with MTBE. The aqueous solution was acidified with 3M HCl to pH 1 and extracted with DCM twice. Combined organics were washed with $H_2O$, dried over anhydrous sodium sulfate, and concentrated in vacuo to yield compound 15 (5 g), which was used directly in the next step without further purification.

Figure 2:
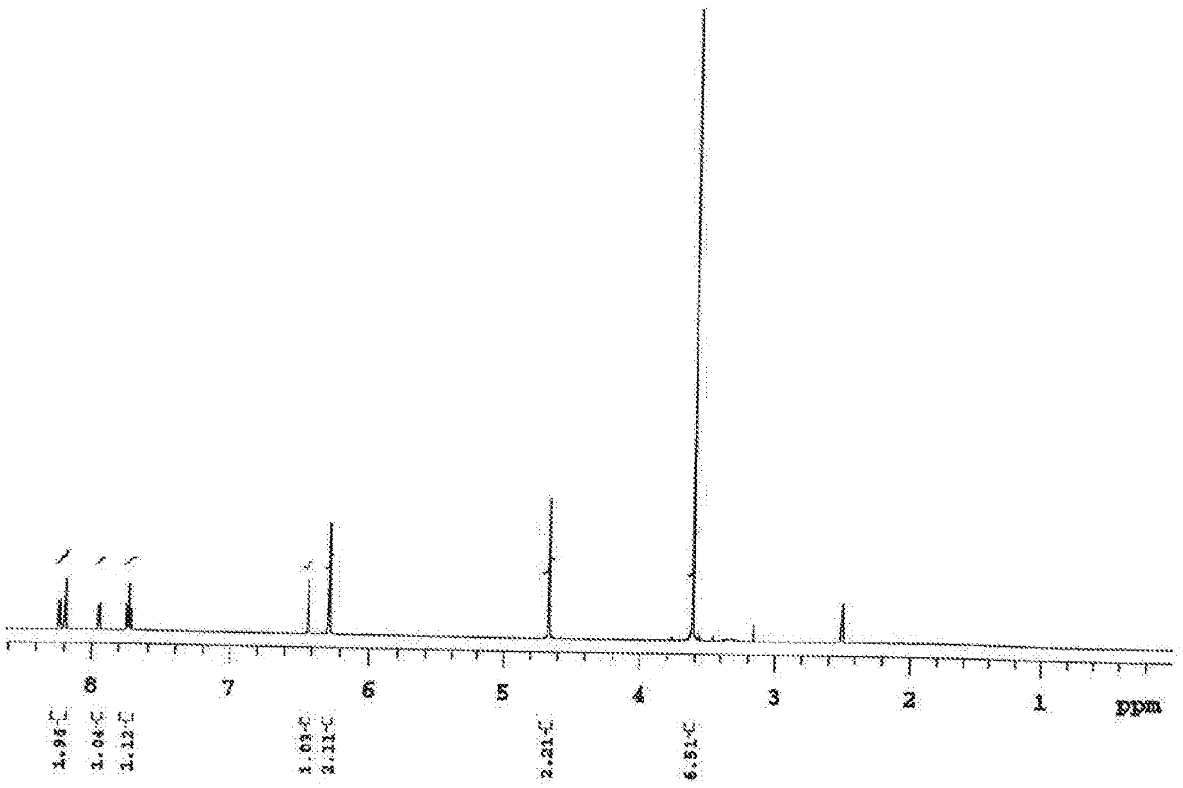
FIG. 2 shows a $^1H$ NMR spectrum of compound A2.

Compound A2. To a solution of compound 15 (16.4 mmol) in acetic acid (25 mL) was added $H_2O_2$ (30%, 82.1 mmoles). The reaction was then stirred at 70° C. and the reaction was by HPLC. After compound 15 and the sulfoxide formed were consumed, the reaction mixture was cooled to room temperature and diluted with water. The resulting solids were collected and washed with water. The solids were then dissolved in aqueous $NaHCO_3$. The aqueous solution was extracted with MTBE and then acidified to pH 1 with 3M HCl. The solids were collected. The filtrate was extracted with DCM. Combined organics were washed with brine and concentrated to yield a second batch of solids. Combined solids were triturated with 10% methanol/DCM over a weekend, washed with 10% methanol/DCM, and dried to yield crude compound A2 (about 2 grams). The crude compound was heated to reflux in chloroform, filtered, and dried in a vacuum oven and aired under reduced pressure. The crude compound was then dissolved in boiling methanol (90 mL), followed by the addition of acetonitrile dropwise until the solution was clear. The solution was cooled to 25° C. and then to −25° C. The solids were collected and washed with cold methanol to yield compound A2 (2 g, 98% pure), a $^{1}$H NMR of which is shown in FIG. 2. MS (ESI) m/z: calcd for $C_{16}H_{17}O_6S$ $[M+H]^+$: 337.1, found: 337.1.

Example B1

Attenuating the Amyloid β40 Level

Figure 3:
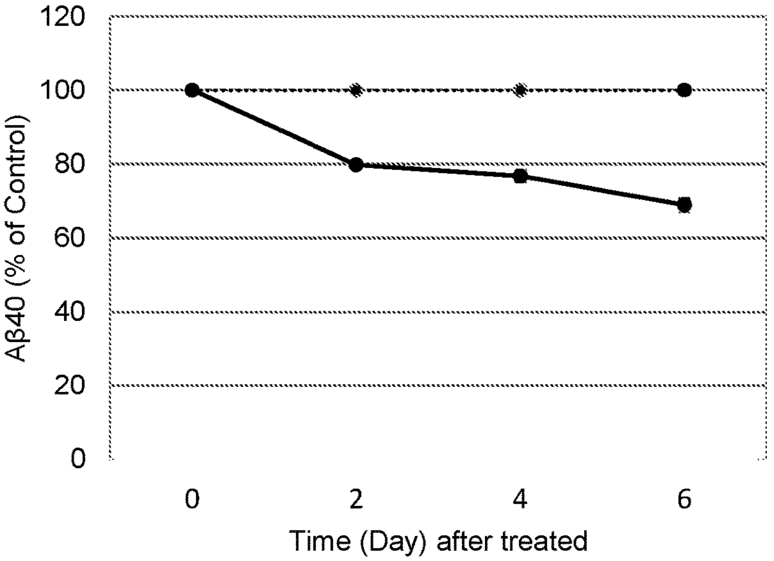
FIG. 3 shows the effect of compound A2 on the level of amyloid β40 (Aβ40) in neurons after 24 h daily treatment, wherein the solid line is for compound A2 treatment and the dotted line is for PBS control.

Induced pluripotent stem cells from a familial Alzheimer's disease patient carrying a duplication of the amyloid precursor protein gene were differentiated to neurons using standard protocols. Israel et al., *Nature* 2012, 482, 216-220. Neural precursor cells were plated on 24-well plates and differentiated to neurons over three weeks. There was an exponential increase in the levels of Aß secreted in these cells starting on Day 4 in culture. The culture medium from each well was collected at Day 6 for Aß40 analysis and replaced with a medium containing a test compound (10 μM) or a phosphate buffered saline (PBS) solution. After 24 h, the medium from each well was collected and the effect of the test compound on the Aß level over 24 h was determined using a commercially available ELISA kit. As shown in FIG. 3, compound A2 reduced Aß40 in this in vitro AD model relative to untreated cells (PBS) by 20% within 24 h and continued to decrease each day, giving a decrease of greater than 30% by Day 6 of treatment.

Example B2

Reduction of Aß40 in CSF of Sprague Dawley Rats after Single Dose Intravenous and Oral Administration of Compound A1

Figure 4:
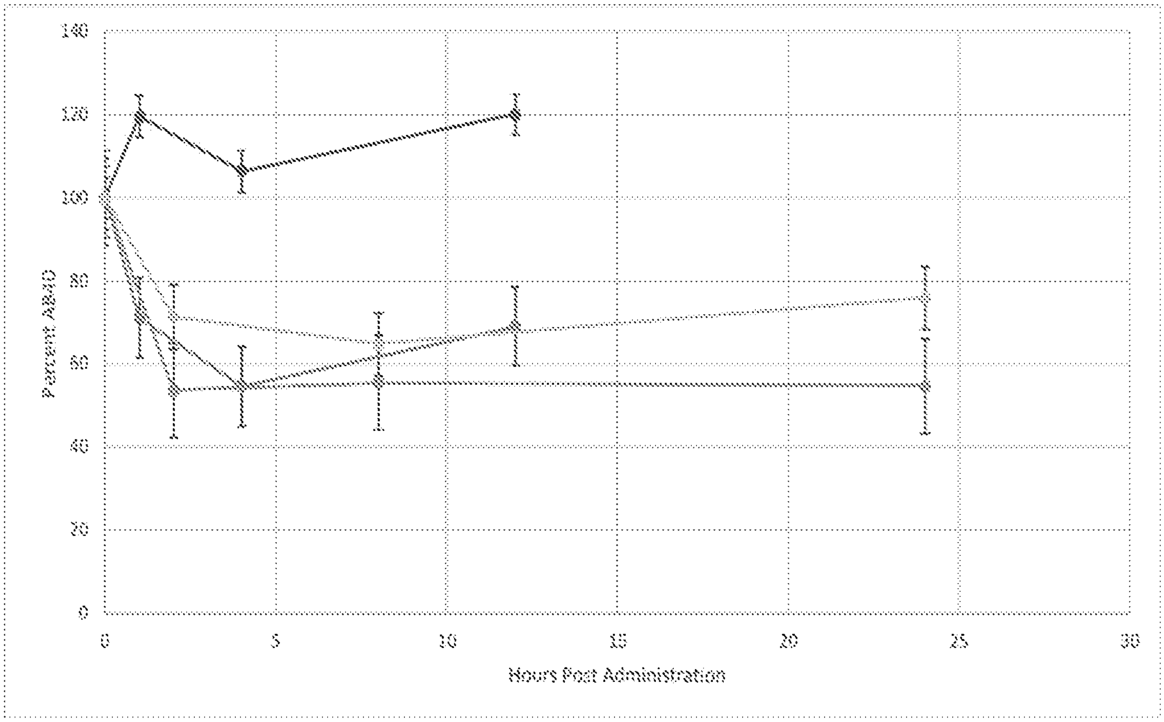
FIG. 4 shows the effect of compound A1 on the level of amyloid β42 (Aβ40) in CSF of Sprague-Dawley rats after a single oral dose treatment.
Figure 5:
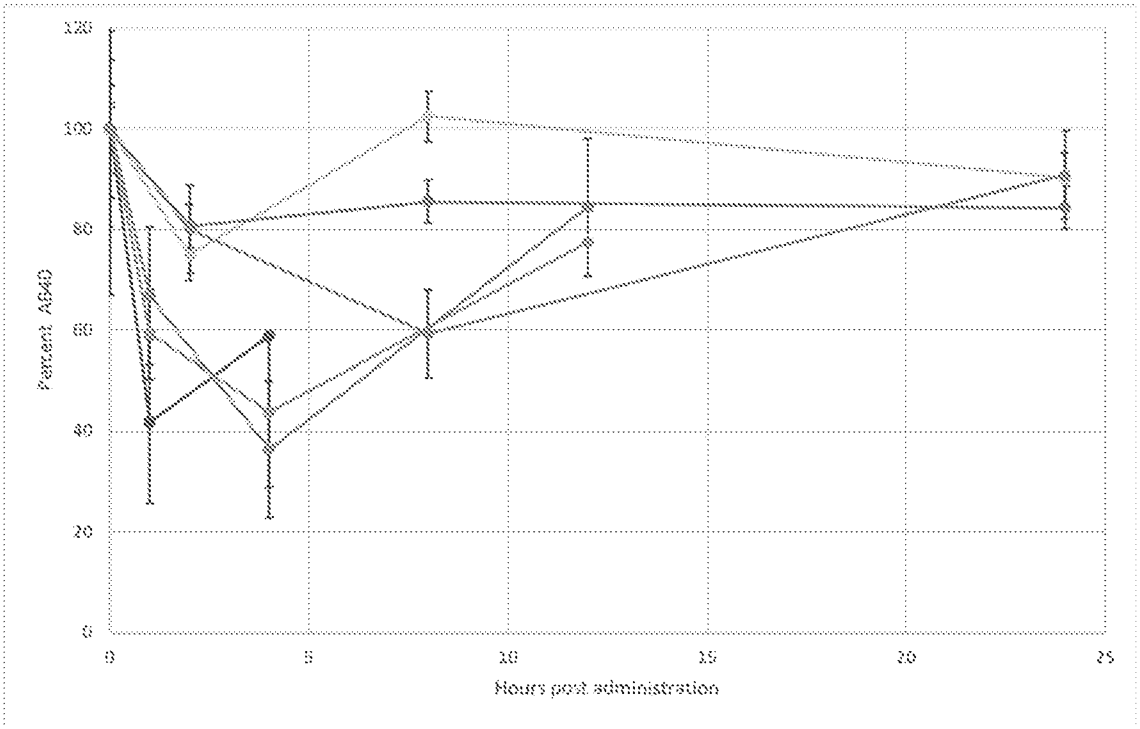
FIG. 5 shows the effect of compound A1 on the level of amyloid β42 (Aβ40) in CSF of Sprague-Dawley rats after a single intravenous treatment.

This non-GLP study had two groups that received compound A1 by intravenous (IV) and oral (PO) administration with 3-6 male rats in each group. Rats received an IV dose of compound A1 at 1 mg/kg. Rats received a PO dose of compound A1 at 10 mg/kg. Plasma samples were collected pre-dose, 0.167 (10 min), 0.5, 1, 2, 4, 6, 8, 12, and 24 h post-dose. CSF samples were collected pre-dose, 0.5, 1, 2, 4, 8, 12, and 24 hours post-dose. As shown in FIG. 4, oral administration of compound A1 decreased A840 in CSF of treated males by up to 50% by 2 h post administration and levels remained lower than starting levels for up to 24 h. As shown in FIG. 5, intravenous administration of compound A1 reduced A840 in CSF of treated rats by 20-60% by 4 h post administration.

Example 3

Preparation of 3-(N-(4-fluoro-3,5-bis(2,2,2-trifluoroethoxy)phenyl)sulfamoyl)benzoic acid A3

A3

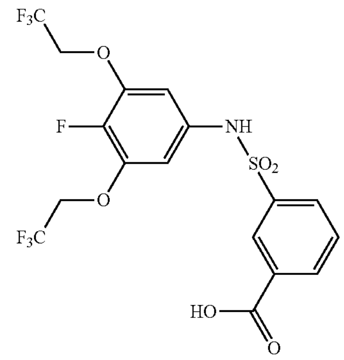

Compound A3 is synthesized as shown in Scheme 3 below.

Scheme 3

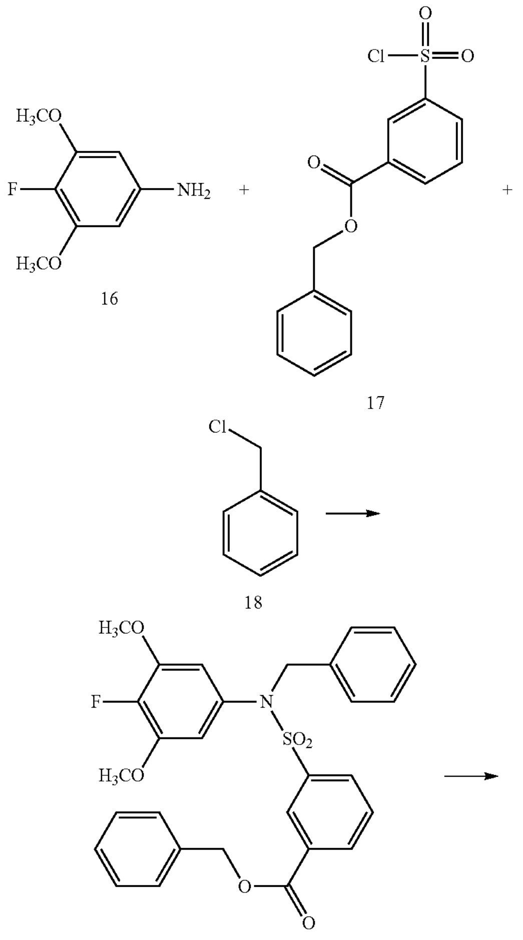

16

17

18

19

-continued

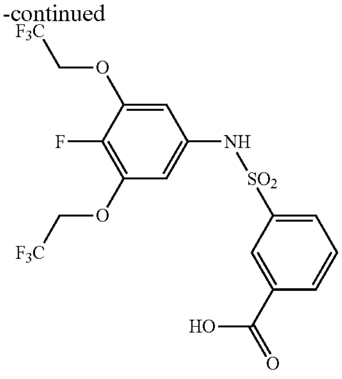

A3

Compound 17. To a solution of 3-(chlorosulfonyl) benzoyl chloride (1.5 g) in tetrahydrofuran (12 mL) are added benzyl alcohol (712 mg) and pyridine (370 mg) at room temperature, and the mixture is stirred for 1 hr. The reaction mixture is diluted with water, and extracted with ethyl acetate. The separated aqueous layer is extracted again with ethyl acetate. The combined organic layer is washed with saturated brine, dried over anhydrous magnesium sulfate, and concentrated under reduced pressure. The residue is purified by silica gel column chromatography (eluent: hexane-ethyl acetate is from 19:1 to 6:1) to give Compound 17 as a colorless oil (yield 1.70 g, 87%).

Compound 19. The reaction of Compounds 16 and 17 is carried out using known methods in the art, for example the methods described in U.S. Pat. No. 5,929,097. To a solution of the resulting intermediate in DMF, NaH is added. The resulting mixture is stirred for several minutes and Compound 18 is then added. The mixture is heated to 80-84° C. with stirring for a period of time under $N_2$. The motion is then cooled to room temperature, diluted with ether, washed with water and brine, dried over $MgSO_4$ and concentrated in vacuo. The residue is triturated with EtOAc to afford Compound 19.

Compound A3. The methoxyl groups in Compound 19 are demethylated in the presence of $BBr_3$ using known methods in the art. Abdel-Halim et al., *J. Med. Chem.* 2014, 57, 6513-6530; Blondet et al., *Tetrahedron Letters* 1994, 35, 2911-2912. The reaction between the two —OH groups on the phenyl ring of the resulting intermediate and $CF_3CH_2OSO_2CF_3$ is carried out using known methods in art, for example the methods described in the International Patent Publication WO2015/186056. The O-benzyl and N-benzyl groups are removed by Stirring in ethanol under 1 atmosphere hydrogen gas at 25° C. in the presence of palladium on charcoal for 18 hours to yield Compound A3.

Example 4

Preparation of 3-(N-(2,6-difluoro-3,5-bis(2,2,2-trifluoroethoxy)phenyl)sulfamoyl)benzoic acid A4

A4

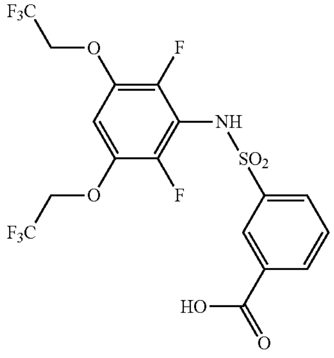

Compound A4 is synthesized as shown in Scheme 4 below.

Scheme 4

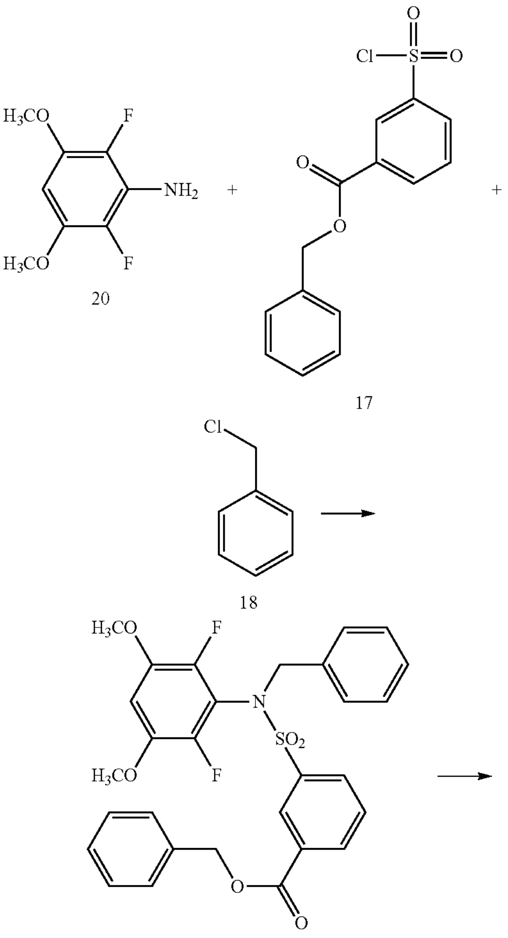

20

17

18

21

-continued

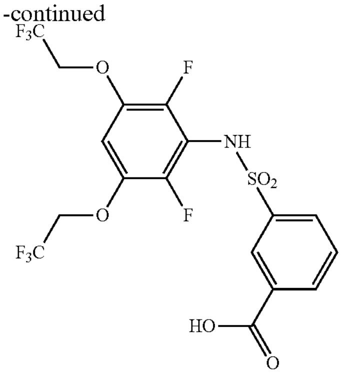

A4

Compound 21. The reaction of Compounds 20 and 17 is carried out using known methods in the art, for example the methods described in U.S. Pat. No. 5,929,097. To a solution of the resulting intermediate in DMF, NaH is added. The resulting mixture is stirred for several minutes and Compound 18 is then added. The mixture is heated to 80-84 degree with stirring for a period of time under $N_2$. The motion is then cooled to room temperature, diluted with ether, washed with water and brine, dried over $MgSO_4$ and concentrated in vacuo. The residue is triturated with EtOAc to afford Compound 21.

Compound A4. The methoxyl groups in Compound 21 are demethylated in the presence of $BBr_3$ using known methods in the art. Abdel-Halim et al., *J. Med. Chem.* 2014, 57, 6513-6530; Blondet et al., *Tetrahedron Letters* 1994, 35, 2911-2912. The reaction between the two —OH groups on the phenyl ring of the resulting intermediate and $CF_3CH_2OSO_2CF_3$ is carried out using known methods in art, for example the methods described in the International Patent Publication WO2015/186056. The O-benzyl and N-benzyl groups are removed by Stirring in ethanol under 1 atmosphere hydrogen gas at 25° C. in the presence of palladium on charcoal for 18 hours to yield Compound A4.

Example 5

Preparation of 3-(N-(2,4,6-trifluoro-3,5-bis(2,2,2-trifluoroethoxy)phenyl)sulfamoyl)benzoic acid A5

A5

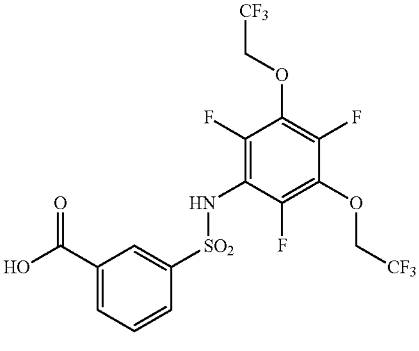

Compound A5 is synthesized as shown in Scheme 5 below.

Scheme 5

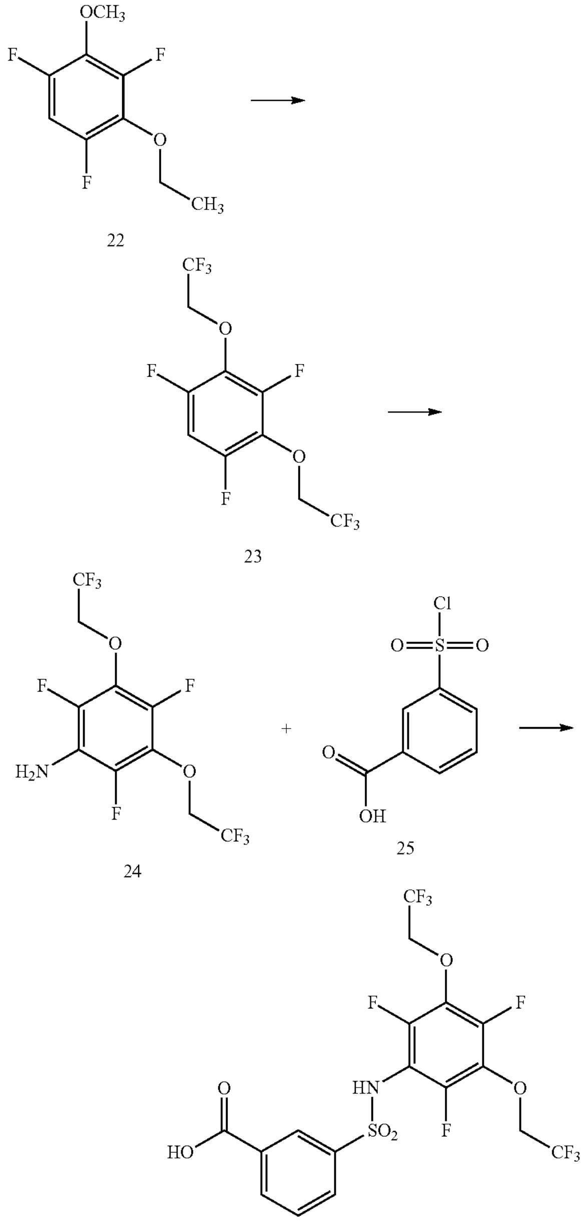

22

23

24

25

A5

Compound 23. The methoxyl and ethoxyl groups in Compound 22 are dealkylated in the presence of $BBr_3$ using known methods in the art. Abdel-Halim et al., *J. Med. Chem.* 2014, 57, 6513-6530. The reaction between the two —OH groups on the phenyl ring of the resulting intermediate and $CF_3CH_2OSO_2CF_3$ is carried out using known methods in art to afford Compound 23, for example, the methods described in the International Patent Publication WO2015/186056.

Compound 24. Compound 23 is treated with 1.1 equivalents of lithium diisopropylamide (LDA) at −78° C. in anhydrous THE under an inert atmosphere for 4 hours to replace the 6-hydrogen with lithium. Excess dry carbon dioxide is added, and the mixture is stirred and allowed to warm to 25° C. The reaction mixture is neutralized with dilute HCl and the THF is removed in vacuo and additional water is added. The precipitated 2,4,6-trifluorobenzoic acid intermediate is isolated by filtration, washed with water, and dried under vacuum. Optionally, this intermediate is purified by crystallization or silica gel chromatography. The resulting intermediate is treated with 1.1 equivalents of diphenylphosphoryl azide to afford a 2,4,6-trifluorobenzoyl azide intermediate. The azide intermediate is not isolated, but is heated in the presence of water to convert it to Compound 24, which is purified by crystallization or silica gel chromatography.

Compound A5. A round-bottom flask (RBF) with stir-bar and septum is charged with Compound 2, dichloromethane, and pyridine. To the solution cooled in an ice bath is added portion-wise Compound 25 over several minutes. The resultant solution is stirred for a period of time to completion as monitored by HPLC. The mixture is partitioned with water. The organic phase is washed with 1M HCl, and brine, then dried over phase separation paper, and diluted with hexanes. The resultant precipitate is filtered, rinsed with hexanes, and dried to give Compound A5. The product is purified by recrystallization from THF, Me-THF or DCM after washing with water and brine.

Example 6

Preparation of 3-(N-(3,5-bis(difluoromethoxy)phenyl)sulfamoyl)benzoic acid A6

A6

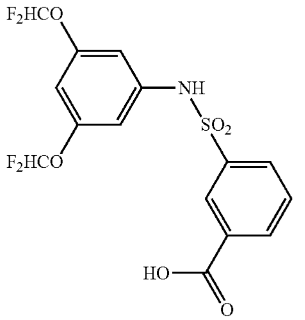

Compound A6 is synthesized as shown in Scheme 6 below.

Scheme 6

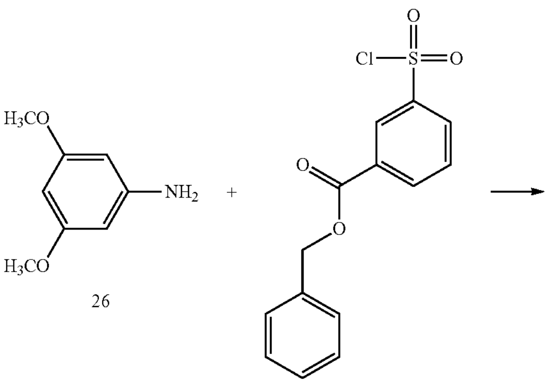

26

17

-continued

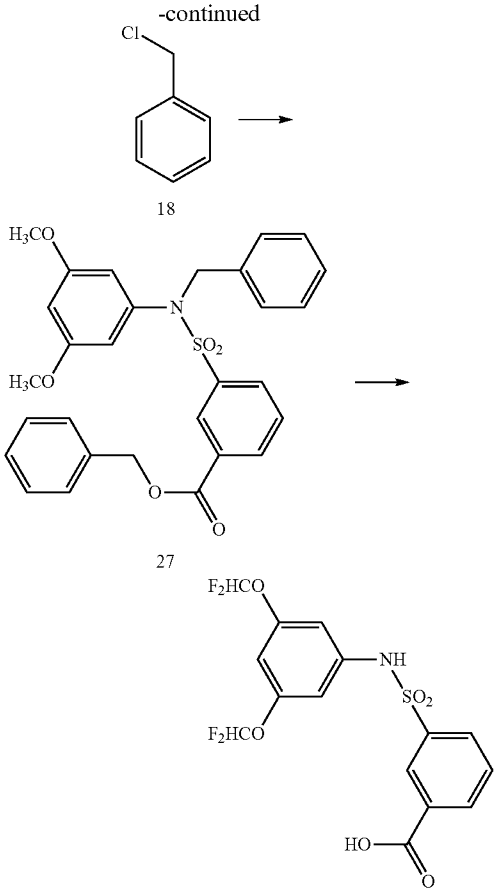

18

27

A6

Compound 27. The reaction of Compounds 26 and 17 is carried out using known methods in the art, for example the methods described in U.S. Pat. No. 5,929,097. To a solution of the resulting intermediate in DMF, NaH is added. The resulting mixture is stirred for several minutes and Compound 18 is then added. The mixture is heated to 80-84° C. with stirring for a period of time under $N_2$. The motion is then cooled to room temperature, diluted with ether, washed with water and brine, dried over $MgSO_4$ and concentrated in vacuo. The residue is triturated with EtOAc to afford Compound 27.

Compound A6. The methoxyl groups in Compound 27 are demethylated in the presence of $BBr_3$ using known methods in the art. Abdel-Halim et al., *J. Med. Chem.* 2014, 57, 6513-6530; Blondet et al., *Tetrahedron Letters* 1994, 35, 2911-2912. The reaction between the two —OH groups on the phenyl ring of the resulting intermediate and $BrCF_2CO_2Na$ is carried out using known methods in art, for example the methods described in the International Patent Publication WO2015/186056. The O-benzyl and N-benzyl groups are removed by Stirring in ethanol under 1 atmosphere hydrogen gas at 25° C. in the presence of palladium on charcoal for 18 hours to yield Compound A6.

Example 7

Preparation of 3-(N-(3,5-bis(difluoromethoxy)-4-fluorophenyl)sulfamoyl)benzoic acid A7

A7

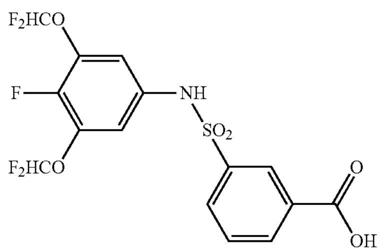

Compound A7 is synthesized as shown in Scheme 7 below.

Scheme 7

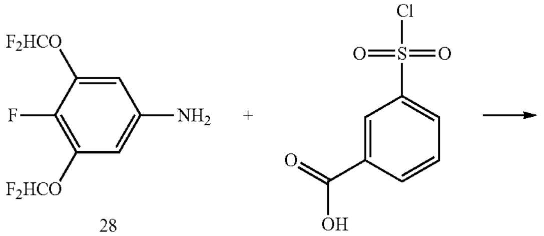

28

25

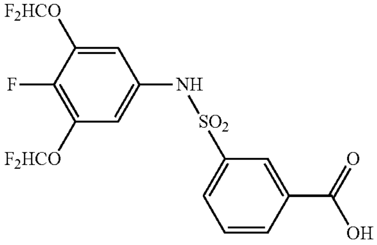

A7

Compound A7. A RBF with stir-bar and septum is charged with Compound 28, dichloromethane, and pyridine. To the solution cooled in an ice bath is added portion-wise Compound 25 over several minutes. The resultant solution is stirred 1 hr to completion as monitored by HPLC. The mixture is partitioned with water. The organic phase is washed with 1M HCl, and brine, then dried over phase separation paper, and diluted with hexanes. The resultant precipitate is filtered, rinsed with hexanes, and dried to give Compound A7. The product is purified by recrystallization from THF, Me-THF or DCM after washing with water and brine.

Example 8

Preparation of 3-(N-(3,5-bis(difluoromethoxy)-2,6-difluorophenyl)sulfamoyl)benzoic acid A8

A8

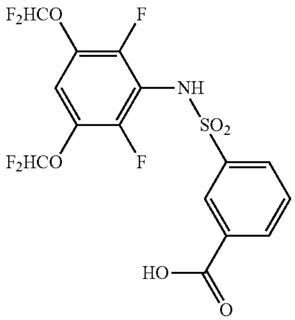

Compound A8 is synthesized as shown in Scheme 8 below.

Scheme 8

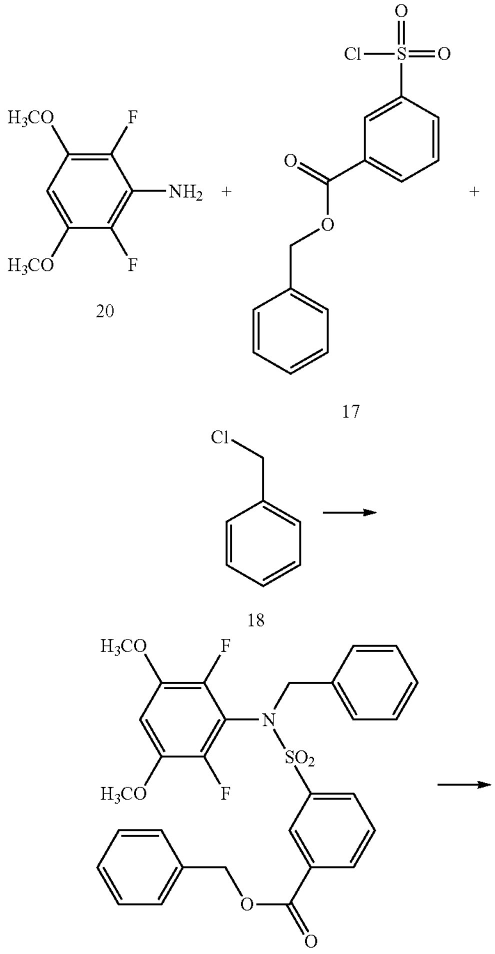

20

17

18

21

-continued

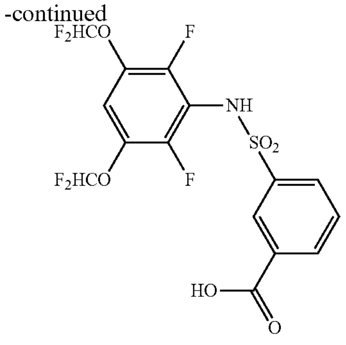

A8

Compound 21. Compound 21 is synthesized using the method as described in Example 4.

Compound A8. The methoxyl groups in Compound 21 are demethylated in the presence of $BBr_3$ using known methods in the art. Abdel-Halim et al., *J. Med. Chem.* 2014, 57, 6513-6530; Blondet et al., *Tetrahedron Letters* 1994, 35, 2911-2912. The reaction between the two —OH groups on the phenyl ring of the resulting intermediate and $BrCF_2CO_2Na$ is carried out using known methods in art, for example the methods described in the International Patent Publication WO2015/186056. The O-benzyl and N-benzyl groups are removed by stirring in ethanol under 1 atmosphere hydrogen gas at 25° C. in the presence of palladium on charcoal for 18 hours to yield Compound A8.

Example 9

Preparation of 3-(N-(3,5-bis(difluoromethoxy)-2,4,6-trifluorophenyl)sulfamoyl)benzoic acid A9

A9

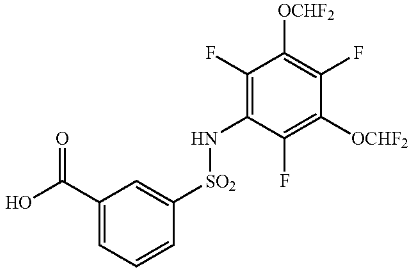

Compound A9 is synthesized as shown in Scheme 9 below.

Scheme 9

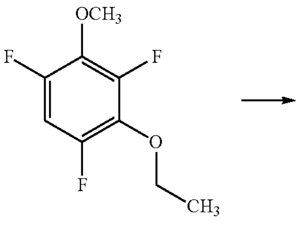

22

-continued

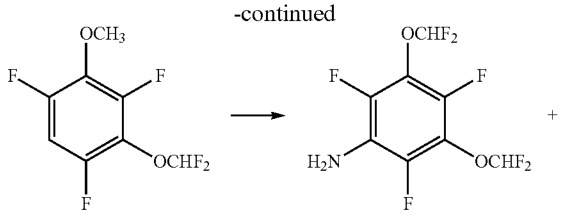

29 30

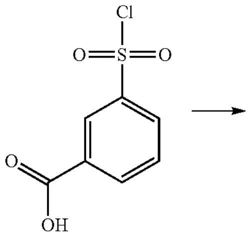

25

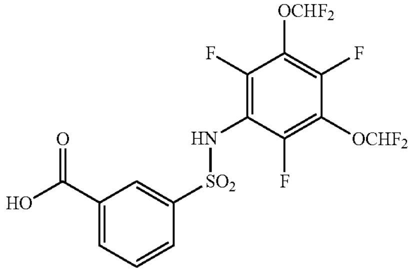

A9

Compound 29. The methoxyl and ethoxyl groups in Compound 22 are dealkylated in the presence of $BBr_3$ using known methods in the art. Abdel-Halim et al., *J. Med. Chem.* 2014, 57, 6513-6530. The reaction between the two hydroxyl groups on the phenyl ring of the resulting intermediate and $BrCF_2CO_2Na$ is carried out using known methods in art to afford Compound 29, for example the methods described in the International Patent Publication WO2015/186056.

Compound 30. Compound 29 is treated with 1.1 equivalents of lithium diisopropylamide (LDA) at −78° C. in anhydrous THE under an inert atmosphere for 4 hours to replace the 6-hydrogen with lithium. Excess dry carbon dioxide is added, and the mixture is stirred and allowed to warm to 25° C. The reaction mixture is neutralized with dilute HCl and the THF is removed in vacuo and additional water is added. The precipitated 2,4,6-trifluorobenzoic acid intermediate is isolated by filtration, washed with water, and dried under vacuum. Optionally, this intermediate is purified by crystallization or silica gel chromatography. The resulting intermediate is treated with 1.1 equivalents of diphenylphosphoryl azide to afford a 2,4,6-trifluorobenzoyl azide intermediate. The azide intermediate is not isolated, but is heated in the presence of water to convert it to Compound 30, which is purified by crystallization or silica gel chromatography.

Compound A9. A RBF with stir-bar and septum is charged with Compound 30, dichloromethane, and pyridine. To the solution cooled in an ice bath is added portion-wise Compound 25 over several minutes. The resultant solution was stirred for a period of time to completion as monitored by HPLC. The mixture is partitioned with water. The organic phase was washed with 1M HCl, and brine, then dried over phase separation paper, and diluted with hexanes. The resultant precipitate is filtered, rinsed with hexanes, and dried to give Compound A9. The product is purified by recrystallization from THF, Me-THF or DCM after washing with water and brine.

Example 10

Preparation of 3-(N-(3,5-bis(2,2-difluoroethoxy) phenyl)sulfamoyl)benzoic acid A10

A10

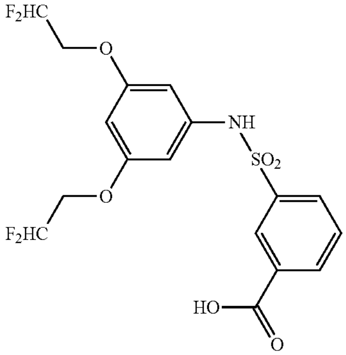

Compound A10 was synthesized as shown in Scheme 10 below.

Scheme 10

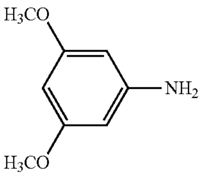

26

+

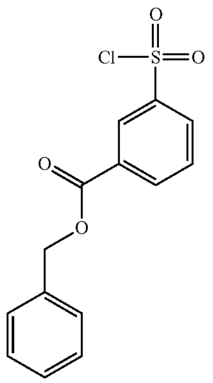

17

+

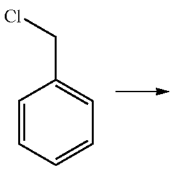

18

-continued

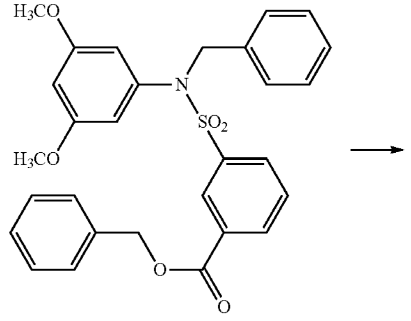

27

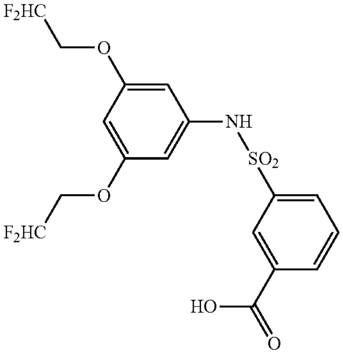

A10

Compound 27. The reaction of Compounds 26 and 17 is carried out using known methods in the art, for example the methods described in U.S. Pat. No. 5,929,097. To a solution of the resulting intermediate in DMF, NaH is added. The resulting mixture is stirred for several minutes and Compound 18 is then added. The mixture is heated to 80-84 degree with stirring for a period of time under $N_2$. The motion is then cooled to room temperature, diluted with ether, washed with water and brine, dried over $MgSO_4$ and concentrated in vacuo. The residue is triturated with EtOAc to afford Compound 27.

Compound A10. The methoxyl groups in Compound 27 are demethylated in the presence of $BBr_3$ using known methods in the art. Abdel-Halim et al., *J. Med. Chem.* 2014, 57, 6513-6530; Blondet et al., *Tetrahedron Letters* 1994, 35, 2911-2912. The reaction between the two —OH groups on the phenyl ring of the resulting intermediate and $CHF_2CH_2OSO_2CF_3$ is carried out using known methods in art, for example the methods described in the International Patent Publication WO2015/186056. The O-benzyl and N-benzyl groups are removed by Stirring in ethanol under 1 atmosphere hydrogen gas at 25° C. in the presence of palladium on charcoal for 18 hours to yield Compound A10.

Example 11

Preparation of 3-(N-(3,5-bis(2,2-difluoroethoxy)-4-fluorophenyl)sulfamoyl)benzoic acid A11

A11

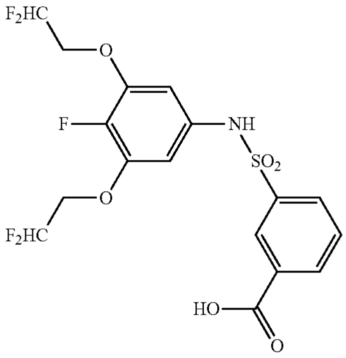

Compound A11 is synthesized as shown in Scheme 11 below.

Scheme 11

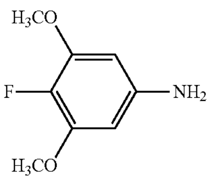

16

+

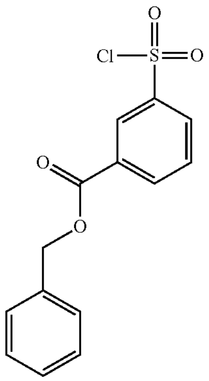

17

+

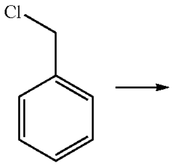

18

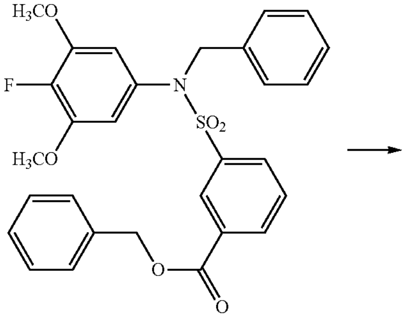

19

-continued

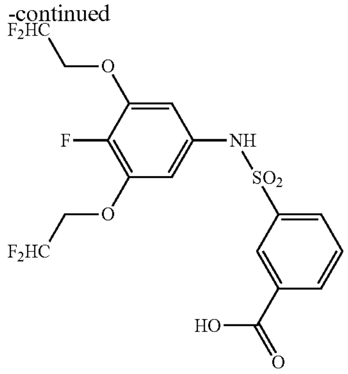

A11

Compound 19. Compound 19 is synthesized using the method as described in Example 3.

Compound A11. The methoxyl groups in Compound 19 are demethylated in the presence of $BBr_3$ using known methods in the art. Abdel-Halim et al., *J. Med. Chem.* 2014, 57, 6513-6530; Blondet et al., *Tetrahedron Letters* 1994, 35, 2911-2912. The reaction between the two —OH groups on the phenyl ring of the resulting intermediate and $CHF_2CH_2OSO_2CF_3$ is carried out using known methods in art, for example the methods described in the International Patent Publication WO2015/186056. The O-benzyl and N-benzyl groups are removed by Stirring in ethanol under 1 atmosphere hydrogen gas at 25° C. in the presence of palladium on charcoal for 18 hours to yield Compound A11.

Example 12

Preparation of 3-(N-(3,5-bis(2,2-difluoroethoxy)-2,6-difluorophenyl)sulfamoyl)benzoic acid A12

A12

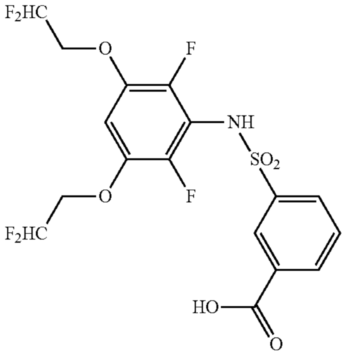

Compound A12 is synthesized as shown in Scheme 12 below.

Scheme 12

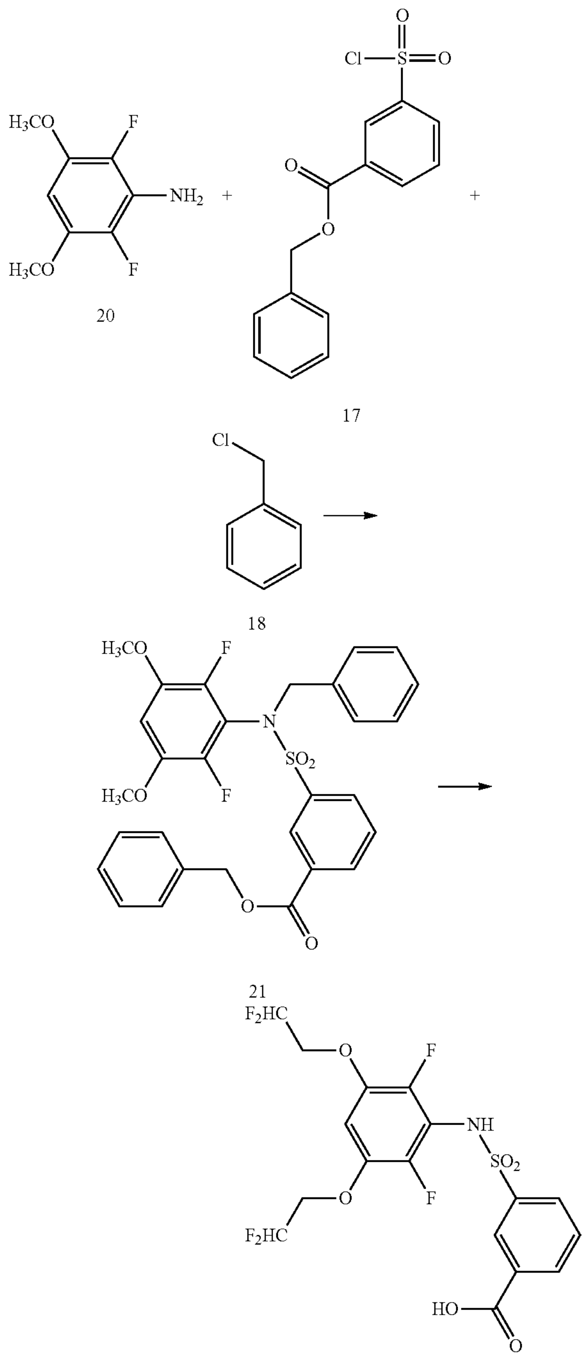

20

17

18

21

A12

Compound 21. Compound 21 is synthesized using the method as described in Example 4.

Compound A12. The methoxyl groups in Compound 21 are demethylated in the presence of $BBr_3$ using known methods in the art. Abdel-Halim et al., *J. Med. Chem.* 2014, 57, 6513-6530; Blondet et al., *Tetrahedron Letters* 1994, 35, 2911-2912. The reaction between the two —OH groups on the phenyl ring of the resulting intermediate and $CHF_2CH_2OSO_2CF_3$ is carried out using known methods in art, for example the methods described in the International Patent Publication WO2015/186056. The O-benzyl and N-benzyl groups are removed by Stirring in ethanol under 1 atmosphere hydrogen gas at 25° C. in the presence of palladium on charcoal for 18 hours to yield Compound A12.

Example 13

Preparation of 3-(N-(3,5-bis(2,2-difluoroethoxy)-2,4,6-trifluorophenyl)sulfamoyl)benzoic acid A13

A13

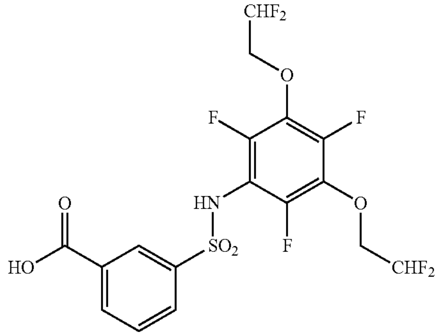

Compound A13 is synthesized as shown in Scheme 13 below.

Scheme 13

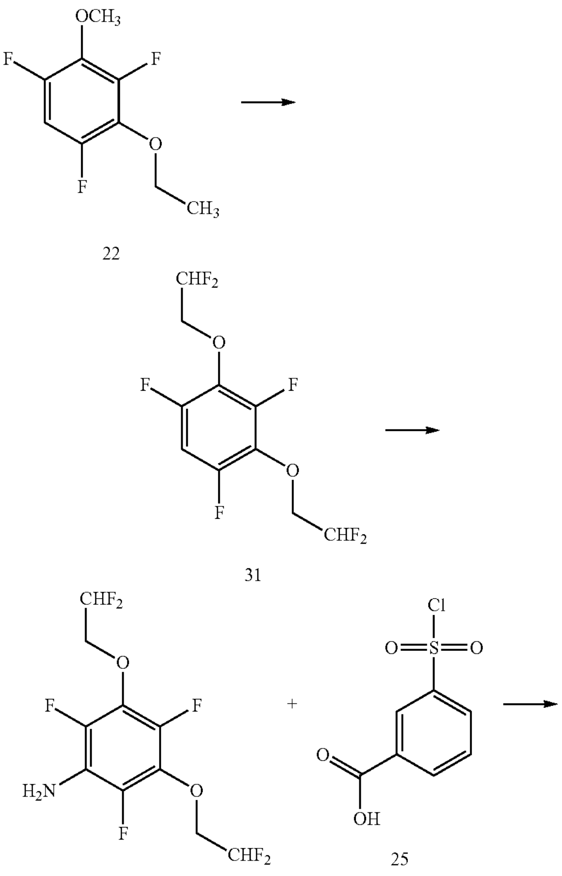

22

31

32

25

-continued

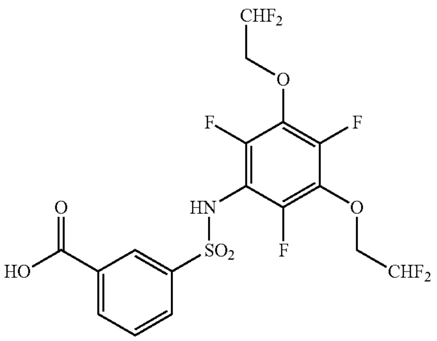

A13

Compound 31. The methoxyl and ethoxyl groups in Compound 22 are dealkylated in the presence of $BBr_3$ using known methods in the art. Abdel-Halim et al., *J. Med. Chem.* 2014, 57, 6513-6530. The reaction between the two hydroxyl groups on the phenyl ring of the resulting intermediate and $CHF_2CH_2OSO_2CF_3$ is carried out using known methods in art to afford Compound 31, for example the methods described in the International Patent Publication WO2015/186056.

Compound 32. Compound 31 is treated with 1.1 equivalents of lithium diisopropylamide (LDA) at −78° C. in anhydrous THE under an inert atmosphere for 4 hours to replace the 6-hydrogen with lithium. Excess dry carbon dioxide is added, and the mixture is stirred and allowed to warm to 25° C. The reaction mixture is neutralized with dilute HCl and the THF is removed in vacuo and additional water is added. The precipitated 2,4,6-trifluorobenzoic acid intermediate is isolated by filtration, washed with water, and dried under vacuum. Optionally, this intermediate is purified by crystallization or silica gel chromatography. The resulting intermediate is treated with 1.1 equivalents of diphenylphosphoryl azide to afford a 2,4,6-trifluorobenzoyl azide intermediate. The azide is not isolated, but is heated in the presence of water to convert it to Compound 32, which is purified by crystallization or silica gel chromatography.

Compound A13. A RBF with stir-bar and septum is charged with Compound 32, dichloromethane, and pyridine. To the solution cooled in an ice bath is added portion-wise Compound 25 over several minutes. The resultant solution is stirred for a period of time to completion as monitored by HPLC. The mixture was partitioned with water. The organic phase was washed with 1M HCl, and brine, then dried over phase separation paper, and diluted with hexanes. The resultant precipitate was filtered, rinsed with hexanes, and dried to give Compound A13. The product is purified by recrystallization from THF, Me-THF or DCM after washing with water and brine.

Example 14

Preparation of 3-(N-(2,6-difluoro-3,5-dimethoxyphenyl)sulfamoyl)benzoic acid A14

A14

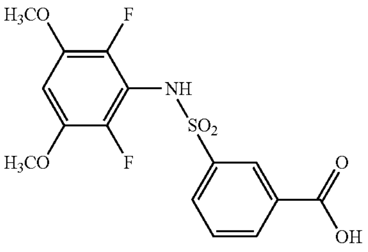

Compound A14 is synthesized as shown in Scheme 14 below.

Scheme 14

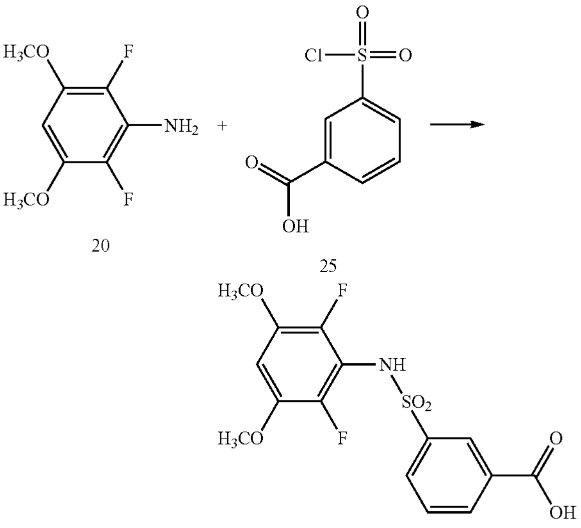

A14

Compound A14. A RBF with stir-bar and septum is charged with Compound 20, dichloromethane, and pyridine. To the solution cooled in an ice bath is added portion-wise Compound 25 over several minutes. The resultant solution is stirred 1 hr to completion as monitored by HPLC. The mixture is partitioned with water. The organic phase is washed with 1M HCl, and brine, then dried over phase separation paper, and diluted with hexanes. The resultant precipitate is filtered, rinsed with hexanes, and dried to give Compound A14. The product is purified by recrystallization from THF, Me-THF or DCM after washing with water and brine.

Example 15

Preparation of 3-(N-(2,4,6-trifluoro-3,5-dimethoxyphenyl)sulfamoyl)benzoic acid A15

A15

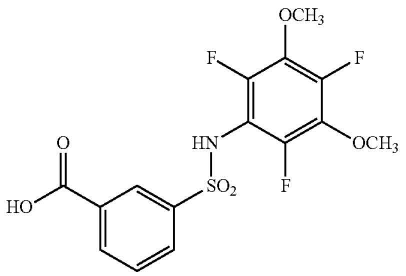

Compound A15 is synthesized as shown in Scheme 15 below.

Scheme 15

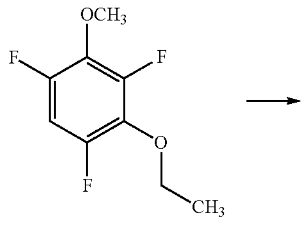

22

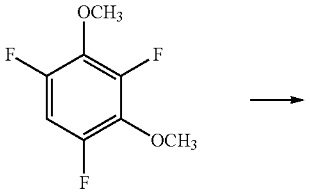

33

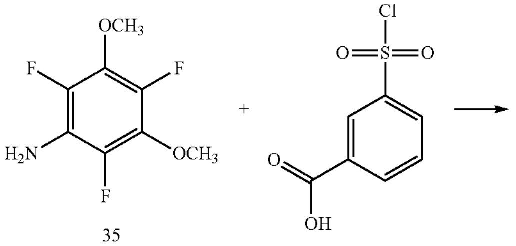

35

25

-continued

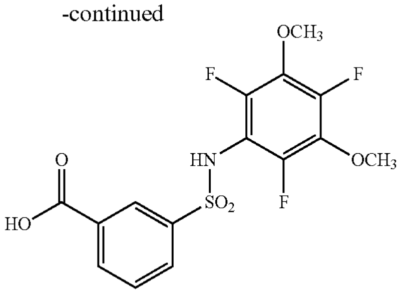

A15

Compound 33. The methoxyl and ethoxyl groups in Compound 22 are dealkylated in the presence of $BBr_3$ using known methods in the art. Abdel-Halim et al., *J. Med. Chem.* 2014, 57, 6513-6530. The reaction between the two hydroxyl groups on the phenyl ring of the resulting intermediate and $CH_3I$ is carried out using known methods in art to afford Compound 33, for example the methods described in the International Patent Publication WO2015/186056.

Compound 35. Compound 33 is treated with 1.1 equivalents of lithium diisopropylamide (LDA) at −78° C. in anhydrous THF under an inert atmosphere for 4 hours to replace the 6-hydrogen with lithium. Excess dry carbon dioxide is added, and the mixture is stirred and allowed to warm to 25° C. The reaction mixture is neutralized with dilute HCl and the THF is removed in vacuo and additional water is added. The precipitated 2,4,6-trifluorobenzoic acid intermediate is isolated by filtration, washed with water, and dried under vacuum. Optionally, this intermediate is purified by crystallization or silica gel chromatography. The resulting intermediate is treated with 1.1 equivalents of diphenylphosphoryl azide to afford a 2,4,6-trifluorobenzoyl azide intermediate. The azide intermediate is not isolated, but is heated in the presence of water to convert it to Compound 35, which is purified by crystallization or silica gel chromatography.

Compound A15. A RBF with stir-bar and septum is charged with Compound 35, dichloromethane, and pyridine. To the solution cooled in an ice bath is added portion-wise Compound 25 over several minutes. The resultant solution was stirred for a period of time to completion as monitored by HPLC. The mixture was partitioned with water. The organic phase was washed with 1M HCl, and brine, then dried over phase separation paper, and diluted with hexanes. The resultant precipitate was filtered, rinsed with hexanes, and dried to give Compound A15. The product is purified by recrystallization from THF, Me-THF or DCM after washing with water and brine.

Example 16

Preparation of 3-(N-(4-fluoro-3,5-dimethoxyphenyl) sulfamoyl)benzoic acid A16

A16

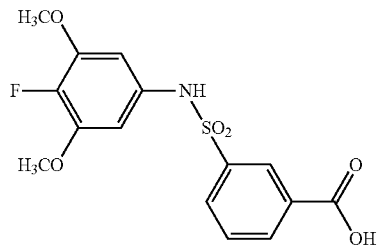

Compound A16 is synthesized as shown in Scheme 16 below.

Scheme 16

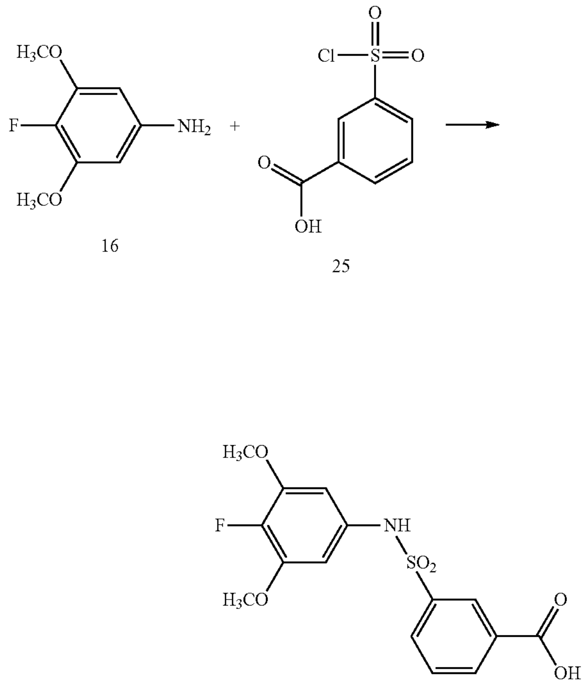

16

25

A16

Compound A16. A RBF with stir-bar and septum is charged with Compound 16, dichloromethane, and pyridine. To the solution cooled in an ice bath is added portion-wise Compound 25 over several minutes. The resultant solution is stirred 1 hr to completion as monitored by HPLC. The mixture is partitioned with water. The organic phase is washed with 1M HCl, and brine, then dried over phase separation paper, and diluted with hexanes. The resultant precipitate is filtered, rinsed with hexanes, and dried to give Compound A16. The product is purified by recrystallization from THF, Me-THF or DCM after washing with water and brine.

Example 17

Preparation of 3-(N-(2,4,6-trifluoro-3-methoxy-5-(trifluoromethoxy)phenyl)sulfamoyl)benzoic acid A17

A17

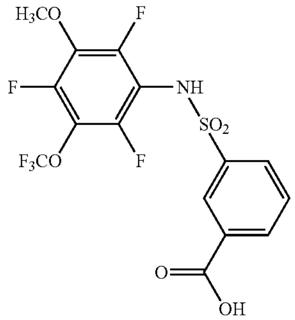

Compound A17 is synthesized as shown in Scheme 17 below.

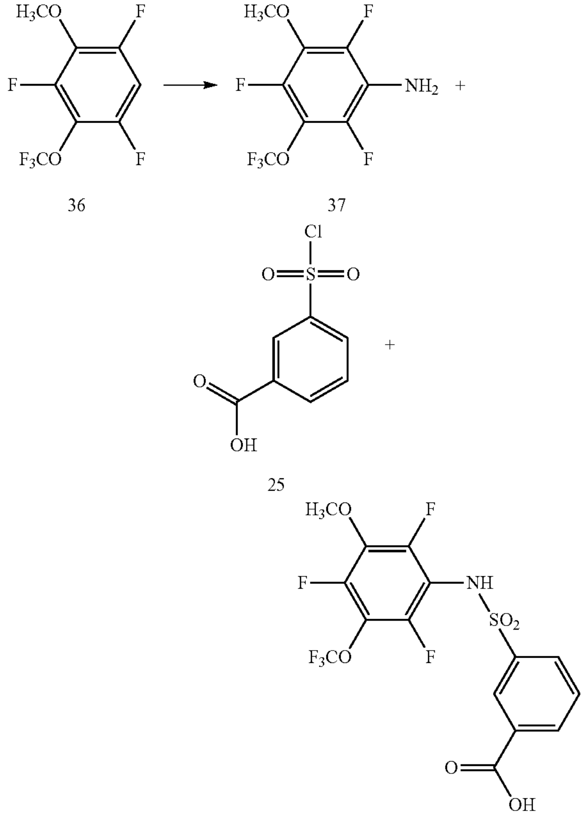

36

37

25

A17

Compound 37. Compound 36 is treated with 1.1 equivalents of lithium diisopropylamide (LDA) at −78° C. in anhydrous THE under an inert atmosphere for 4 hours to replace the 6-hydrogen with lithium. Excess dry carbon dioxide is added, and the mixture is stirred and allowed to warm to 25° C. The reaction mixture is neutralized with dilute HCl and the THF is removed in vacuo and additional water is added. The precipitated 2,4,6-trifluorobenzoic acid intermediate is isolated by filtration, washed with water, and dried under vacuum. Optionally, this intermediate is purified by crystallization or silica gel chromatography. The resulting intermediate is treated with 1.1 equivalents of diphenylphosphoryl azide to afford a 2,4,6-trifluorobenzoyl azide intermediate. The azide intermediate is not isolated, but is heated in the presence of water to convert it to Compound 37, which is purified by crystallization or silica gel chromatography.

Compound A17. A RBF with stir-bar and septum is charged with Compound 37, dichloromethane, and pyridine. To the solution cooled in an ice bath is added portion-wise Compound 25 over several minutes. The resultant solution was stirred for a period of time to completion as monitored by HPLC. The mixture was partitioned with water. The organic phase was washed with 1M HCl, and brine, then dried over phase separation paper, and diluted with hexanes. The resultant precipitate was filtered, rinsed with hexanes, and dried to give Compound A17. The product is purified by recrystallization from THF, Me-THF or DCM after washing with water and brine.

Example 18

Preparation of 3-(N-(3-ethoxy-2,4,6-trifluoro-5-methoxyphenyl)sulfamoyl)benzoic acid A18

A18

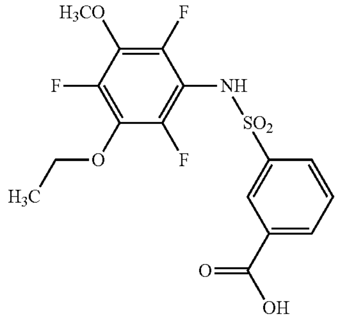

Compound A18 is synthesized as shown in Scheme 18 below.

Scheme 18

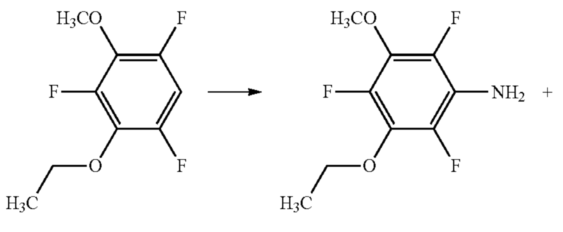

38

39

-continued

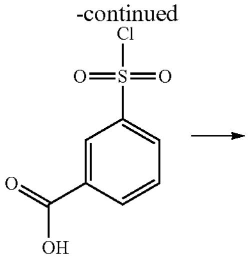

25

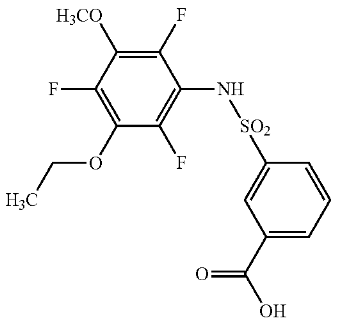

A18

Compound 39. Compound 38 is treated with 1.1 equivalents of lithium diisopropylamide (LDA) at −78° C. in anhydrous THE under an inert atmosphere for 4 hours to replace the 6-hydrogen with lithium. Excess dry carbon dioxide is added, and the mixture is stirred and allowed to warm to 25° C. The reaction mixture is neutralized with dilute HCl and the THF is removed in vacuo and additional water is added. The precipitated 2,4,6-trifluorobenzoic acid intermediate is isolated by filtration, washed with water, and dried under vacuum. Optionally, this intermediate is purified by crystallization or silica gel chromatography. The resulting intermediate is treated with 1.1 equivalents of diphenylphosphoryl azide to afford a 2,4,6-trifluorobenzoyl azide intermediate. The azide intermediate is not isolated, but is heated in the presence of water to convert it to Compound 39, which is purified by crystallization or silica gel chromatography.

Compound A18. A RBF with stir-bar and septum is charged with Compound 39, dichloromethane, and pyridine. To the solution cooled in an ice bath is added portion-wise Compound 25 over several minutes. The resultant solution was stirred for a period of time to completion as monitored by HPLC. The mixture was partitioned with water. The organic phase was washed with 1M HCl, and brine, then dried over phase separation paper, and diluted with hexanes. The resultant precipitate was filtered, rinsed with hexanes, and dried to give Compound A18. The product is purified by recrystallization from THF, Me-THF or DCM after washing with water and brine.

Example 19

Preparation of 3-(N-(2,6-difluoro-3,5-dimethoxy-4-(methoxycarbonyl)phenyl)sulfamoyl)benzoic acid A19

A19

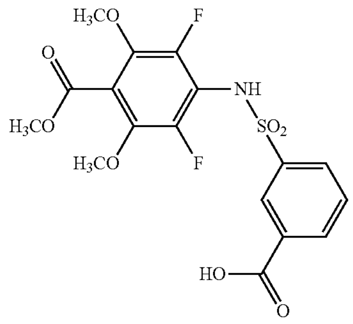

Compound A19 is synthesized as shown in Scheme 19 below.

Scheme 19

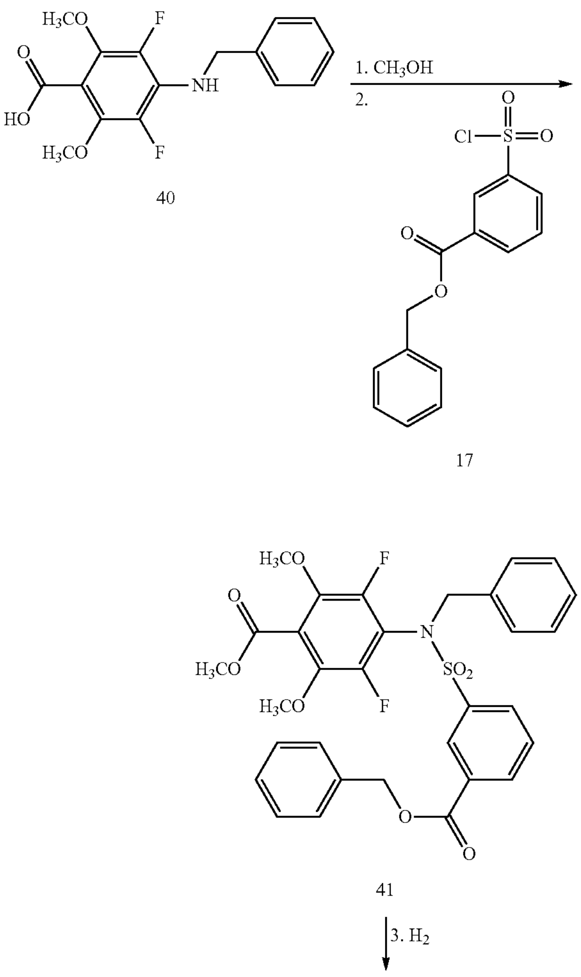

40

17

41

-continued

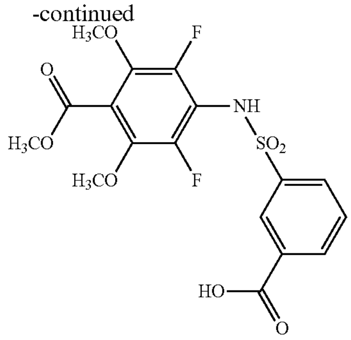

A19

Compound 41. Step 1. To a solution of Compound 40, add 1.1 equivalents of di-isopropyl carbodiimide, followed by 2 equivalents of DIPEA, 0.1 equivalent of 4-dimethylamino-pyridine, and 10 equivalents of dry methanol to form the amine methyl ester derivative of Compound 40 (not shown). Alternately, without limitation, the amine methyl ester derivative of Compound 40 can be prepared as follows: to a solution of Compound 40, 1 equivalent of oxalyl chloride is added, followed by 2 equivalents of DIPEA and 10 equivalents of dry methanol. Step 2: The amine methyl ester derivative of Compound 40 is dissolved in dichloroethane with exclusion of moisture, 2 equivalents of pyridine is added and the solution is cooled to 0° C. With this temperature being maintained, a solution of sulfonyl chloride 17 in dichloroethane is instilled. It is stirred for 30 more minutes at 0° C. and 5 more hours at room temperature. The suspension is shaken out three times with 2N hydrochloric acid and twice with water, the organic phase is dried on sodium sulfate, filtered, concentrated by evaporation and the residue is chromatographed on silica gel 60 (Merck) with ethyl acetate/hexane. The fractions, concentrated by evaporation, of corresponding polarity yield Sulfonamide 41. Step 3: Compound 41 is stirred in ethanol under 1 atmosphere hydrogen gas at 25° C. in the presence of palladium on charcoal for 18 hours to remove benzyl groups. The resulting compound A19 is purified by recrystallization from THF, Me-THF or DCM after washing with water and brine. Optionally, a salt of A19 can be recrystallized instead of the free acid form of A19.

Example 20

Preparation of 3-(N-(4-(tert-butoxycarbonyl)-2,6-difluoro-3,5-dimethoxyphenyl)sulfamoyl)benzoic acid A20

A20

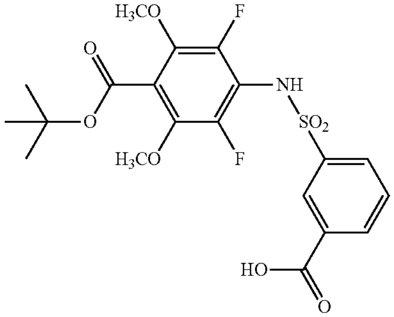

Compound A20 is synthesized as shown in Scheme 20 below.

Scheme 20

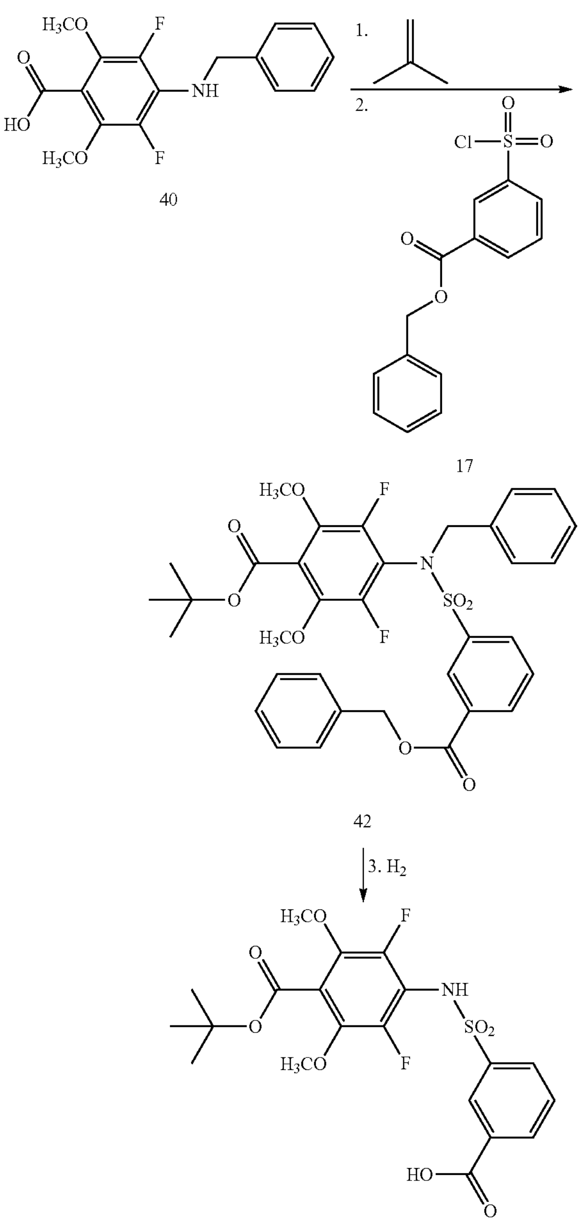

40 17 42

A20

Compound 42. Step 1. To a solution of Compound 40 is added 10 mole percent TFA. Isobutene is bubbled in at 25° C. until conversion to the t-butyl ester is complete by TLC. Step 2: The t-butyl ester derivative of Compound 40 is dissolved in dichloroethane with exclusion of moisture, 2 equivalents of pyridine is added and the solution is cooled to 0° C. With this temperature being maintained, a solution of sulfonyl chloride 17 in dichloroethane is instilled. It is stirred for 30 more minutes at 0° C. and 5 more hours at room temperature. The suspension is shaken out three times with 2N hydrochloric acid and twice with water, the organic phase is dried on sodium sulfate, filtered, concentrated by evaporation and the residue is chromatographed on silica gel 60 (Merck) with ethyl acetate/hexane. The fractions, concentrated by evaporation, of corresponding polarity yield Sulfonamide 42. Step 3: Compound 42 is stirred in ethanol under 1 atmosphere hydrogen gas at 25° C. in the presence of palladium on charcoal for 18 hours to remove benzyl groups. The resulting compound A20 is purified by recrystallization from THF, Me-THF or DCM after washing with water and brine. Optionally, a salt of A20 can be recrystallized instead of the free acid form of A20.

Example 21

Preparation of 3-(N-(4-(dimethylcarbamoyl)-2,6-difluoro-3,5-dimethoxyphenyl)sulfamoyl)benzoic acid A21

A21

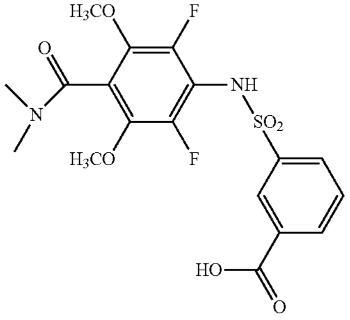

Compound A21 is synthesized as shown in Scheme 21 below.

Scheme 21

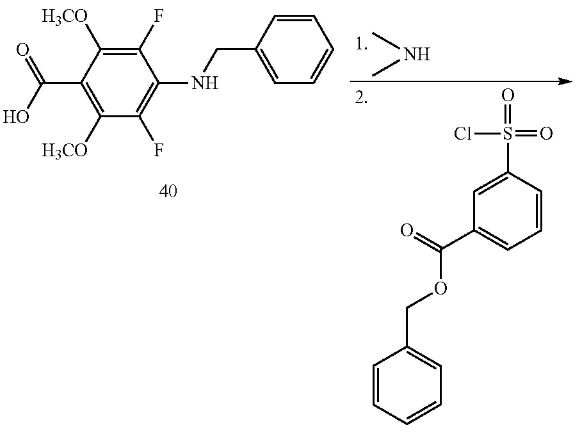

40

17

-continued

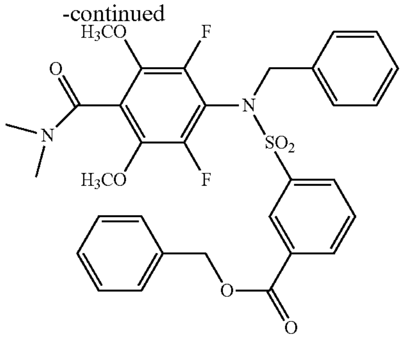

43

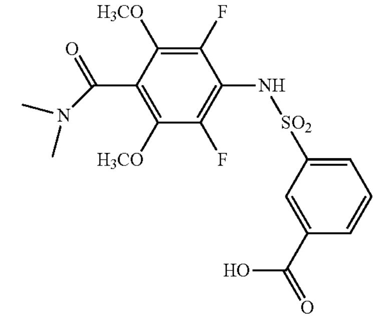

A21

Step 1: A solution of dimethylamine (20 mmol) and Compound 40 (20 mmol) in dry DCM (250 mL) is stirred at 0° C. under nitrogen, and 1-Ethyl-3-(3-dimethylaminopropyl)carbodiimide (EDCI, 40 mmol) is added portion wise. The mixture is stirred for 1 hour at 0° C. then 1 hour at room temperature. After addition of DCM (250 mL), the organic layer is washed with water, 10% citric acid, water, brine, dried ($MgSO_4$), filtered and concentrated. Silica gel chromatography using hexane/EtOAc or crystallization is optionally used to purify the dimethylamide of Compound 40, or it is used "as is" to synthesize Compound 43. Step 2: Compound 43. To a solution of the dimethylamide of Compound 40, pyridine is added and the solution is cooled to 0° C. With this temperature being maintained, a solution of Compound 17 in dichloroethane is instilled. It is stirred for 30 more minutes at 0° C. and 5 more hours at room temperature. The suspension is shaken out three times with 2N hydrochloric acid and twice with water, the organic phase is dried on sodium sulfate, filtered, concentrated by evaporation and the residue is chromatographed on silica gel 60 (Merck) with ethyl acetate/hexane. The fractions, concentrated by evaporation, of corresponding polarity yield Compound 43. Compound A21. Step 3: Compound 43 is stirred in ethanol under 1 atmosphere hydrogen gas at 25° C. in the presence of palladium on charcoal for 18 hours to remove benzyl groups. Compound A21 is purified by recrystallization from THF, Me-THF or DCM after washing with water and brine. Optionally, a salt can be recrystallized instead of the free acid form of A21.

Example 22

Preparation of 3-(N-(2,6-difluoro-3,5-dimethoxy-4-(piperidine-1-carbonyl)phenyl)sulfamoyl)benzoic acid A22

A22

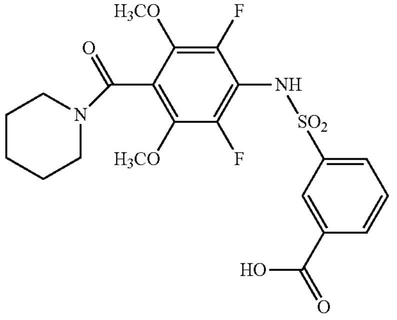

Compound A22 is synthesized as shown in Scheme 22 below.

Scheme 22

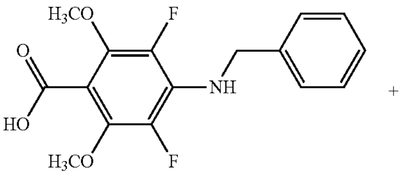

40

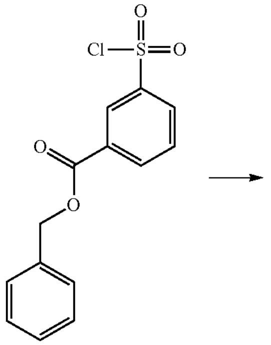

17

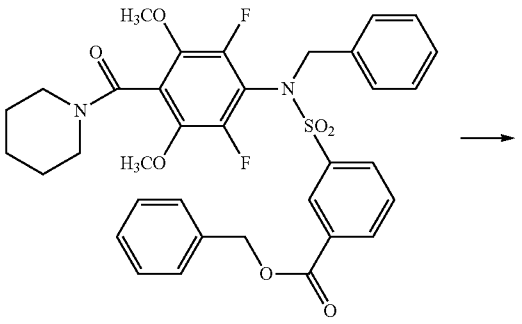

44

-continued

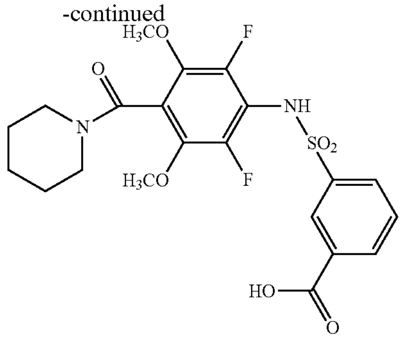

A22

Compound 44. Step 1: A solution of piperidine (20 mmol) and Compound 40 (20 mmol) in dry DCM (250 mL) is stirred at 0° C. under nitrogen, and EDCI (40 mmol) is added portion wise. The mixture is stirred for 1 hour at 0° C. then 1 hour at room temperature. After addition of DCM (250 mL), the organic layer is washed with water, 10% citric acid, water, brine, dried ($MgSO_4$), filtered and concentrated. Silica gel chromatography using hexane/EtOAc or crystallization is optionally used to purify the piperidine amide of Compound 40, or it is used "as is" to synthesize Compound 44. Step 2: Compound 44. To a solution of the dimethylamide of Compound 40, pyridine is added and the solution is cooled to 0° C. With this temperature being maintained, a solution of Compound 17 in dichloroethane is instilled. It is stirred for 30 more minutes at 0° C. and 5 more hours at room temperature. The suspension is shaken out three times with 2N hydrochloric acid and twice with water, the organic phase is dried on sodium sulfate, filtered, concentrated by evaporation and the residue is chromatographed on silica gel 60 (Merck) with ethyl acetate/hexane. The fractions, concentrated by evaporation, of corresponding polarity yield Compound 44. Step 3: Compound A22. Compound 44 is stirred in ethanol under 1 atmosphere hydrogen gas at 25° C. in the presence of palladium on charcoal for 18 hours to remove benzyl groups. The resulting crude compound A22 is purified by recrystallization from THF, Me-THF or DCM after washing with water and brine. Optionally, a salt can be recrystallized instead of the free acid form of A21.

The examples set forth above are provided to give those of ordinary skill in the art with a complete disclosure and description of how to make and use the claimed embodiments, and are not intended to limit the scope of what is disclosed herein. Modifications understood to persons of skill in the art may include, without limitation, changes in type of solvent, reaction temperature, reaction time, number of equivalents of reagents, chromatographic solvents and media, and methods of purification. Crystallographic purification methods may optionally be used instead of chromatographic purification solvents. All publications, patents, and patent applications cited in this specification are incorporated herein by reference as if each such publication, patent or patent application were specifically and individually indicated to be incorporated herein by reference.

What is claimed is:

1. A method of inhibiting the production of amyloid β in a subject in need thereof, the method comprising administering to said subject an effective amount of a compound chosen from compounds of Formula I(a) and pharmaceutically acceptable salts thereof:

I(a)

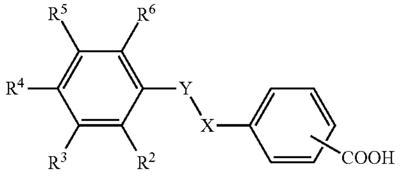

wherein, in Formula I(a):

X is $—SO_2—$;

Y is $—CH_2—$ or —NH—;

$R^3$ and $R^5$ are independently chosen from hydrogen, $—NR^{1a}S(O)_2R^{1d}$, $—C(R^4)—$, optionally substituted $C_{1-6}$ alkyl, and optionally substituted $C_{1-6}$ alkoxy, with the proviso that if $R^3$ or $R^5$ is optionally substituted $C_{1-6}$ alkyl or optionally substituted $C_{1-6}$ alkoxy, the substituent(s) are fluoro;

$R^A$ is $—S(O)_2R^{1a}$; and $R^{1a}$, $R^{1d}$, $R^2$, $R^4$, and $R^6$ are independently chosen from hydrogen and $C_{1-6}$ alkyl.

2. The method of claim 1, wherein the amyloid β is amyloid β40 or amyloid β42.

3. The method according to claim 1, wherein:

Y is $—CH_2—$;

$R^2$, $R^4$, and $R^6$ are independently chosen from hydrogen and methyl; and one of $R^3$ and $R^5$ is substituted $C_{1-6}$ alkyl.

4. The method according to claim 1, wherein:

Y is $—CH_2—$;

$R^2$, $R^4$, and $R^6$ are independently chosen from hydrogen and methyl; and one of $R^3$ and $R^5$ is trifluoromethyl.

5. The method according to claim 1, wherein:

Y is $—CH_2—$;

$R^2$, $R^4$, and $R^6$ are independently chosen from hydrogen and methyl; and $R^3$ and $R^5$ are $C_{1-6}$ alkoxy.

6. The method according to claim 1, wherein:

Y is $—CH_2—$;

$R^2$, $R^4$, and $R^6$ are independently chosen from hydrogen and methyl; and $R^3$ and $R^5$ are methoxy.

7. The method according to claim 1, wherein:

Y is —NH—;

$R^2$, $R^4$, and $R^6$ are independently chosen from hydrogen and methyl; and one of $R^3$ and $R^5$ is substituted $C_{1-6}$ alkyl.

8. The method according to claim 1, wherein:

Y is —NH—;

$R^2$, $R^4$, and $R^6$ are independently chosen from hydrogen and methyl; and one of $R^3$ and $R^5$ is trifluoromethyl.

9. The method according to claim 1, wherein:

Y is —NH—;

$R^2$, $R^4$, and $R^6$ are independently chosen from hydrogen and methyl; and $R^3$ and $R^5$ are $C_{1-6}$ alkoxy.

10. The method according to claim 1, wherein:

Y is —NH—;

$R^2$, $R^4$, and $R^6$ are independently chosen from hydrogen and methyl; and $R^3$ and $R^5$ are methoxy.

11. The method according to claim 1, wherein:

Y is —NH—;

$R^2$ is $—NR^{1a}S(O)_2R^{1d}$; and $R^2$, $R^3$, $R^4$, $R^5$, and $R^6$ are hydrogen.

12. The method according to claim 1, comprising administering a composition comprising a compound of Formula I(a) and at least one pharmaceutically acceptable excipient to said subject.

13. A method of inhibiting the production of amyloid β in a cell, the method comprising contacting said cell with an effective amount of a compound chosen from compounds of Formula I(a) and pharmaceutically acceptable salts thereof:

I(a)

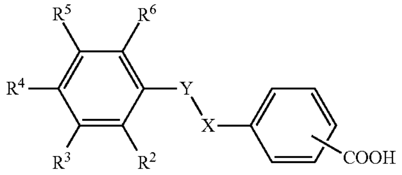

wherein, in Formula I(a):

X is —$SO_2$—;

Y is —$CH_2$— or —NH—;

$R^3$ and $R^5$ are independently chosen from hydrogen, —$NR^{1a}S(O)_2R^{1d}$, —$C(R^A)$—, optionally substituted $C_{1-6}$ alkyl, and optionally substituted $C_{1-6}$ alkoxy, with the proviso that if $R^3$ or $R^5$ is optionally substituted $C_{1-6}$ alkyl or optionally substituted $C_{1-6}$ alkoxy, the substituent(s) are fluoro;

$R^A$ is —$S(O)_2R^{1a}$; and $R^{1a}$, $R^{1d}$, $R^2$, $R^4$, and $R^6$ are independently chosen from hydrogen and $C_{1-6}$ alkyl.

14. The method of claim 13, wherein the amyloid β is amyloid β36, amyloid β37, amyloid β38, amyloid β39, amyloid β40, amyloid β41, amyloid β42, amyloid β 43, amyloid β44, amyloid β45, amyloid β46, amyloid β47, amyloid β48, amyloid β49, amyloid β50, amyloid β51, amyloid β52, or a combination of two or more thereof.

15. The method according to claim 13, wherein:

Y is —$CH_2$—;

$R^2$, $R^4$, and $R^6$ are independently chosen from hydrogen and methyl; and one of $R^3$ and $R^5$ is substituted $C_{1-6}$ alkyl.

16. The method according to claim 13, wherein:

Y is —$CH_2$—;

$R^2$, $R^4$, and $R^6$ are independently chosen from hydrogen and methyl; and one of $R^3$ and $R^5$ is trifluoromethyl.

17. The method according to claim 13, wherein:

Y is —$CH_2$—;

$R^2$, $R^4$, and $R^6$ are independently chosen from hydrogen and methyl; and $R^3$ and $R^5$ are $C_{1-6}$ alkoxy.

18. The method according to claim 13, wherein:

Y is —$CH_2$—;

$R^2$, $R^4$, and $R^6$ are independently chosen from hydrogen and methyl; and $R^3$ and $R^5$ are methoxy.

19. The method according to claim 13, wherein:

Y is —NH—;

$R^2$, $R^4$, and $R^6$ are independently chosen from hydrogen and methyl; and one of $R^3$ and $R^5$ is substituted $C_{1-6}$ alkyl.

20. The method according to claim 13, wherein:

Y is —NH—;

$R^2$, $R^4$, and $R^6$ are independently chosen from hydrogen and methyl; and one of $R^3$ and $R^5$ is trifluoromethyl.

21. The method according to claim 13, wherein:

Y is —NH—;

$R^2$, $R^4$, and $R^6$ are independently chosen from hydrogen and methyl; and $R^3$ and $R^5$ are $C_{1-6}$ alkoxy.

22. The method according to claim 13, wherein:

Y is —NH—;

$R^2$, $R^4$, and $R^6$ are independently chosen from hydrogen and methyl; and $R^3$ and $R^5$ are methoxy.

23. The method according to claim 13, wherein:

Y is —NH—;

$R^2$ is —$NR^{1a}S(O)_2R^{1d}$; and $R^2$, $R^3$, $R^4$, $R^5$, and $R^6$ are hydrogen.

* * * * *